US009416391B2

(12) United States Patent
Martinho et al.

(10) Patent No.: US 9,416,391 B2
(45) Date of Patent: Aug. 16, 2016

(54) **METHOD FOR IDENTIFYING CANCER DRUG CANDIDATES IN *DROSOPHILA***

(71) Applicant: Thelial Technologies S.A., Lisbon (PT)

(72) Inventors: Rui Gonçalo Viegas Russo da Conceição Martinho, Lisbon (PT); Virginia Mylena de Oliveira Marques, Corroios (PT); Richard John Hampson, Lisbon (PT)

(73) Assignee: Thelial Technologies S.A., Lisbon (PT)

( * ) Notice: Subject to any disclaimer, the term of this patent is extended or adjusted under 35 U.S.C. 154(b) by 0 days.

(21) Appl. No.: 13/679,341

(22) Filed: Nov. 16, 2012

(65) Prior Publication Data

US 2013/0136694 A1    May 30, 2013

Related U.S. Application Data

(60) Provisional application No. 61/561,560, filed on Nov. 18, 2011.

(51) Int. Cl.
| | | |
|---|---|---|
| *C12N 15/00* | (2006.01) | |
| *C12Q 1/00* | (2006.01) | |
| *C12Q 1/02* | (2006.01) | |
| *G01N 33/50* | (2006.01) | |

(52) U.S. Cl.
CPC ............ *C12Q 1/025* (2013.01); *G01N 33/5085* (2013.01)

(58) Field of Classification Search
CPC .. C12Q 1/025; C12Q 1/6897; A01K 67/0339; G01N 33/5085
See application file for complete search history.

(56) References Cited

U.S. PATENT DOCUMENTS

| | | |
|---|---|---|
| 6,316,690 B1 | 11/2001 | Fogarty |
| 6,489,127 B1 | 12/2002 | Duyk et al. |
| 6,548,733 B2 | 4/2003 | Hafen |
| 6,552,181 B1 | 4/2003 | Dean et al. |
| 6,579,701 B1 | 6/2003 | Keegan et al. |
| 7,312,041 B2 | 12/2007 | Lu et al. |
| 7,317,086 B2 | 1/2008 | Dean et al. |
| 7,595,151 B2 | 9/2009 | Lu et al. |
| 7,642,400 B2 | 1/2010 | Fields et al. |
| 7,695,899 B2 | 4/2010 | Su et al. |
| 2004/0224349 A1 | 11/2004 | Alexander et al. |
| 2006/0010505 A1 | 1/2006 | Baranski et al. |
| 2006/0156421 A1 | 7/2006 | Cagan et al. |
| 2008/0124702 A1 | 5/2008 | Lu et al. |

FOREIGN PATENT DOCUMENTS

| | | |
|---|---|---|
| WO | WO 2005/112978 | 12/2005 |
| WO | WO 2013/073979 | 5/2013 |

OTHER PUBLICATIONS

Tsen C., et al. A *Drosophila* Model to Identify Polyamine-Drug Conjugates That Target the Polyamine Transporter in an Intact Epithelium. J. Med. Chem. 2008, 51, 324-330.*
Leduc CJ. Cancer Therapeutics in *Drosophila melanogaster*: A Closer Look at the ErbB Family of Receptor Tyrosine Kinases. WPI, Project Report, 2007, 1-35.*
Perrimon N, et al. Applications of High-Throughput RNA Interference Screens to Problems in Cell and Developmental Biology. Genetics 175: 7-16, Jan. 2007.*
Warner SJ, et al. The Cdc42/Par6/aPKC polarity complex regulates apoptosis-induced compensatory proliferation in epithelia. Curr Biol. Apr. 27, 2010;20(8):677-86.*
Brock R, et al. Rapid characterization of green fluorescent protein fusion proteins on the molecular and cellular level by fluorescence correlation microscopy. Proc. Natl. Acad. Sci. USA vol. 96, pp. 10123-10128, Aug. 1999.*
Huynh JR, et al. Bazooka and PAR-6 are required with PAR-1 for the maintenance of oocyte fate in *Drosophila*. Current Biology 2001, 11:901-906.*
Petronczki M, et al. DmPAR-6 directs epithelial polarity and asymmetric cell division of neuroblasts in *Drosophila*. Nature Cell Biology, January 2001, 3:43-49.*
Venken et al Recombineering-mediated tagging of *Drosophila* genomic constructs for in vivo localization and acute protein inactivation. Nucleic Acids Res. Oct. 2008;36(18):1-9.*
Prasad et al., A protocol for culturing *Drosophila melanogaster* stage 9 egg chambers for live imaging. Nature Protocols, 2:2467-2473 (2007).*
Theurkauf et al., Reorganization of the cytoskeleton during *Drosophila oogenesis*: implications for axis specification and intercellular transport. Development 115, 923-936 (1992).*
Pokrywka et al., Microtubules Are a General Component of mRNA Localization Systems in *Drosophila oocytes*. Developmental Biology, 167, 363-370 (1995).*
Becalska et al., Lighting up mRNA localization in *Drosophila oogenesis*. Development, 136.2493•2503 (2009).*
Royer et al., Epithelial cell polarity: a major gatekeeper against cancer? Cell Death and Differentiation (2011) 18, 1470-1477.*

(Continued)

*Primary Examiner* — Kevin Hill
*Assistant Examiner* — Arthur S Leonard
(74) *Attorney, Agent, or Firm* — Gary J. Gershik; Cooper & Dunham LLP

(57) ABSTRACT

A process for preparing information that identifies a compound as capable of perturbing the epithelium in a *D. melanogaster* comprising the steps of: i) obtaining a *D. melanogaster* which is genetically unmodified except that the *D. melanogaster* optionally comprises at least one nucleotide sequence encoding a reporter polypeptide operably linked to a promoter of an endogenous protein; ii) contacting the *D. melanogaster* with the compound; and iii) determining whether there is a difference between the epithelium of the *D. melanogaster* of ii) and the epithelium of a corresponding *D. melanogaster* not contacted with the compound, wherein the presence of a difference between the epithelium of the *D. melanogaster* contacted with the compound and the epithelium of a corresponding *D. melanogaster* not contacted with the compound identifies the compound as a compound that is capable of perturbing the epithelium in a *D. melanogaster*.

12 Claims, No Drawings

(56) References Cited

OTHER PUBLICATIONS

International Search Report, issued Apr. 3, 2013 in connection with PCT International Patent Application No. PCT/PT2012/000046.

Anuradha et al (2008) "*Drosophila*-based in vivo assay for the validation of inhibitors of the epidermal growth factor receptor/Ras pathway" Journal of Biosciences (Bangalore), 33(5):731-742.

Giacomotto et al (2010) "High-Throughput screening in small animal models, where are we?" British Journal of Pharmacology, 160(2):204-216.

Gladstone et al (2011) "Chemical genetics and drug screening in cancer models" Journal of Genetics and Genomics, 39(10):497-504.

Basteck and St Jonston (2008) "*Drosophila oogenesis*" Current Biology 18(23):R1082-R1087.

Bleicher et al. (2003) "Hit and Lead Generation: Beyond High-Throughput Screening" Nature Reviews 2, 369-378.

Das and Cagan, (2010) "*Drosophila* as a Novel Therapeutic Discovery Tool for Thyroid Cancer" Thyroid 20(7):689-695.

Brumby and Richardson, (2005) "Using *Drosophila melanogaster* to Map Human Cancer Pathways" Nature Reviews Cancer 5, 626-639.

GenBank Accession No. NM_133010, (2000) Adams et al.

Hampson and Wyatt, (2011) "Whole Organism Based Techniques and Approaches in Early State Oncology Drug Discovery—Patents and Trends" Recent Patents on Endocrine, Metabolic & Immune Drug Discovery 5(3):1-9.

Horne-Badovinac and Bilder, (2005) "Mass Transit: Epithelial Morphogenesis in the *Drosophila* Egg Chamber" Developmental Dynamics 232:559-574.

Janssens et al., (2006) "The Wnt-dependent signaling pathways as target in oncology drug discovery" Investigational New Drugs 24:263-280.

Johnston, (2002) "The Art and Design of Genetic Screens: *Drosophila melanogaster*" Nature Reviews Genetics 3, 176-188.

Keseru and Makara, (2006) "Hit discovery and hit-to-lead approaches" Drug Discovery today 11(15/16):741-748.

Pandey and Nichols, (2011) "Human Disease Models in *Drosophila melanogaster* and the Role of the Fly in Therapeutic Drug Discovery" Pharmacological Reviews 63:411-436.

Petronczki and Knoblich, (2001) "DmPAR-6 directs epithelial polarity and asymmetric cell division of neuroblasts in *Drosophila*" Nature Cell Biology 3, 43-49.

Tepass, (1997) "Epithelial differentiation in *Drosophila*" BioEssays 19(8):673-682.

Tickoo and Russell, (2002) "*Drosophila melanogaster* as a model system for drug discovery and pathway screening" Current Opinion in Pharmacology 2:555-560.

Wirtz-Peitz et al., (2008) "Linking Cell Cycle to Asymmetric Division: Aurora-A Phosphorylates the Par Complex Co Regulate Numb Localization" Cell 135, 161-173.

Medros Technology website, available at: www.medrospharma.com/Technology.html, accessed Jan. 8, 2013.

Exelixis website, available at: www.exelixis,com, accessed Jan. 8, 2013.

The Genetics Company website, available at www.the-genetics.com, accessed Jan. 8, 2013.

Summit plc website, available at www.summitplc.com, accessed Jan. 8, 2013.

Phylonix website, available at www.phylonix.com, accessed Jan. 8, 2013.

PerkinElmer website, available at www.perkinelmer.com/Sitemap, accessed Jan. 8, 2013.

Scottish Biomedical website, available at www.scottish-biomedical.com, accessed Jan. 8, 2013.

Apr. 30, 2014 Office Action, issued in connection with Canadian Patent Application No. 2,796,520.

Knoblich, J.A., Asymmetric cell division: recent developments and their implications for tumour biology, Nat Rev Mol Cell Biol., 11(12), pp. 849-860, Dec. 2010.

Fields, A.P., Targeting the oncogenic protein Cinase C*I* signaling pathway for the treatment of cancer. Biochemical Society Transactions, 35(5), pp. 996-1000, 2007.

* cited by examiner

SEQUENCE LISTING

<160> NUMBER OF SEQ ID NOS: 13

<210> SEQ ID NO 1
<211> LENGTH: 606
<212> TYPE: PRT
<213> ORGANISM: Drosophila melanogaster

<400> SEQUENCE: 1

Met Gln Lys Met Pro Ser Gln Ile Leu Asn Asp Gly Ser Ser Val Thr
1               5                   10                  15

Leu Ser Ser Ala Ser Met Asn Met Ala Asn Thr Pro Asn Ser Ile Thr
            20                  25                  30

Val Lys Thr Ala Tyr Asn Gly Gln Ile Ile Thr Thr Ile Asn Lys
        35                  40                  45

Asn Ile Ser Tyr Glu Glu Leu Cys Tyr Glu Ile Arg Asn Ile Cys Arg
    50                  55                  60

Phe Pro Leu Asp Gln Pro Phe Thr Ile Lys Trp Val Asp Glu Asn
65                  70                  75                  80

Asp Pro Cys Thr Ile Ser Thr Lys Met Glu Leu Asp Glu Ala Ile Arg
                85                  90                  95

Leu Tyr Glu Met Asn Phe Asp Ser Gln Leu Val Ile His Val Phe Pro
            100                 105                 110

Asn Val Pro Gln Ala Pro Gly Leu Ser Cys Asp Gly Glu Asp Arg Ser
        115                 120                 125

Ile Tyr Arg Arg Gly Ala Arg Arg Trp Arg Lys Leu Tyr Arg Val Asn
    130                 135                 140

Gly His Ile Phe Gln Ala Lys Arg Phe Asn Arg Arg Ala Phe Cys Ala
145                 150                 155                 160

Tyr Cys Gln Asp Arg Ile Trp Gly Leu Gly Arg Gln Gly Phe Lys Cys
                165                 170                 175

Ile Gln Cys Lys Leu Leu Val His Lys Lys Cys His Lys Leu Val Gln
            180                 185                 190

Lys His Cys Thr Asp Gln Pro Glu Pro Leu Val Lys Glu Arg Ala Glu
        195                 200                 205

Glu Ser Ser Asp Pro Ile Pro Val Pro Leu Pro Pro Leu Pro Tyr Glu
    210                 215                 220

Ala Met Ser Gly Gly Ala Glu Ala Cys Glu Thr His Asp His Ala His
225                 230                 235                 240

Ile Val Ala Pro Pro Pro Glu Asp Pro Leu Glu Pro Gly Thr Gln
                245                 250                 255

Arg Gln Tyr Ser Leu Asn Asp Phe Glu Leu Ile Arg Val Ile Gly Arg
            260                 265                 270

Gly Ser Tyr Ala Lys Val Leu Met Val Glu Leu Arg Arg Thr Arg Arg
        275                 280                 285

Ile Tyr Ala Met Lys Val Ile Lys Lys Ala Leu Val Thr Asp Asp Glu
    290                 295                 300

Asp Ile Asp Trp Val Gln Thr Glu Lys His Val Phe Glu Thr Ala Ser
305                 310                 315                 320

Asn His Pro Phe Leu Val Gly Leu His Ser Cys Phe Gln Thr Pro Ser
                325                 330                 335

Arg Leu Phe Phe Val Ile Glu Phe Val Arg Gly Gly Asp Leu Met Tyr
            340                 345                 350

His Met Gln Arg Gln Arg Arg Leu Pro Glu Glu His Ala Arg Phe Tyr
        355                 360                 365

```
Ala Ala Glu Ile Ser Leu Ala Leu Asn Phe Leu His Glu Lys Gly Ile
    370                 375                 380

Ile Tyr Arg Asp Leu Lys Leu Asp Asn Val Leu Leu Asp His Glu Gly
385                 390                 395                 400

His Ile Lys Leu Thr Asp Tyr Gly Met Cys Lys Glu Gly Ile Arg Pro
                405                 410                 415

Gly Asp Thr Thr Ser Thr Phe Cys Gly Thr Pro Asn Tyr Ile Ala Pro
            420                 425                 430

Glu Ile Leu Arg Gly Glu Asp Tyr Gly Phe Ser Val Asp Trp Trp Ala
                435                 440                 445

Leu Gly Val Leu Leu Tyr Glu Met Leu Ala Gly Arg Ser Pro Phe Asp
    450                 455                 460

Leu Ala Gly Ala Ser Glu Asn Pro Asp Gln Asn Thr Glu Asp Tyr Leu
465                 470                 475                 480

Phe Gln Val Ile Leu Glu Lys Thr Ile Arg Ile Pro Arg Ser Leu Ser
                485                 490                 495

Val Arg Ala Ala Ser Val Leu Lys Gly Phe Leu Asn Lys Asn Pro Ala
            500                 505                 510

Asp Arg Leu Gly Cys His Arg Glu Ser Ala Phe Met Asp Ile Val Ser
                515                 520                 525

His Pro Phe Phe Lys Asn Met Asp Trp Glu Leu Leu Glu Arg Lys Gln
    530                 535                 540

Val Thr Pro Pro Phe Lys Pro Arg Leu Asp Ser Asp Arg Asp Leu Ala
545                 550                 555                 560

Asn Phe Pro Pro Glu Phe Thr Gly Glu Ala Val Gln Leu Thr Pro Asp
                565                 570                 575

Asp Asp His Val Ile Asp Asn Ile Asp Gln Ser Glu Phe Glu Gly Phe
            580                 585                 590

Glu Tyr Val Asn Pro Leu Leu Met Ser Leu Glu Asp Cys Val
                595                 600                 605

<210> SEQ ID NO 2
<211> LENGTH: 1520
<212> TYPE: PRT
<213> ORGANISM: Drosophila melanogaster

<400> SEQUENCE: 2

Met Phe Asp Val Pro Pro Lys Cys Pro Ala Leu Ala Asn Lys Leu Gly
1               5                   10                  15

Gly Leu Phe Gly Trp Arg His Thr Tyr Lys Val Ala Ala Lys Gln Glu
            20                  25                  30

Gly Ile Pro His Gly Gln Leu His Lys Ser Tyr Ser Leu Thr Leu Pro
        35                  40                  45

Lys Arg Pro Pro Ser Pro Ser Thr Tyr Ser Cys Val Lys Pro Asp Ser
    50                  55                  60

Trp Val Thr Val Thr His Leu Gln Thr Gln Ser Gly Ile Leu Asp Pro
65                  70                  75                  80

Asp Asp Cys Val Arg Asp Val Ala Asp Arg Glu Gln Ile Leu Ala
                85                  90                  95

His Phe Asp Pro Gly Pro Pro Gly Val Pro Gln Gly Gly Gly
            100                 105                 110

Asp Gly Ala Ser Gly Ser Ser Ser Val Gly Thr Gly Ser Pro Asp Ile
        115                 120                 125

Phe Arg Asp Pro Thr Asn Thr Glu Ala Pro Thr Cys Pro Arg Asp Leu
    130                 135                 140
```

```
Ser Thr Pro His Ile Glu Val Thr Ser Thr Thr Ser Gly Pro Met Ala
145                 150                 155                 160

Gly Leu Gly Val Gly Leu Met Val Arg Arg Ser Ser Asp Pro Asn Leu
            165                 170                 175

Leu Ala Ser Leu Lys Ala Glu Gly Ser Asn Lys Arg Trp Ser Ala Ala
            180                 185                 190

Ala Pro His Tyr Ala Gly Gly Asp Ser Pro Glu Arg Leu Phe Leu Asp
        195                 200                 205

Lys Ala Gly Gly Gln Leu Ser Pro Gln Trp Glu Glu Asp Asp Asp Pro
210                 215                 220

Ser His Gln Leu Lys Glu Gln Leu Leu His Gln Gln Pro His Ala
225                 230                 235                 240

Ala Asn Gly Gly Ser Ser Gly Asn His Gln Pro Phe Ala Arg Ser
            245                 250                 255

Gly Arg Leu Ser Met Gln Phe Leu Gly Asp Gly Asn Gly Tyr Lys Trp
            260                 265                 270

Met Glu Ala Ala Glu Lys Leu Gln Asn Gln Pro Pro Ala Gln Gln Thr
        275                 280                 285

Tyr Gln Gln Gly Ser His His Ala Gly His Gly Gln Asn Gly Ala Tyr
290                 295                 300

Ser Ser Lys Ser Leu Pro Arg Glu Ser Arg Lys Glu Pro Leu Gly
305                 310                 315                 320

Gln Ala Tyr Glu Ser Ile Arg Glu Lys Asp Gly Glu Met Leu Leu Ile
            325                 330                 335

Ile Asn Glu Tyr Gly Ser Pro Leu Gly Leu Thr Ala Leu Pro Asp Lys
            340                 345                 350

Glu His Gly Gly Gly Leu Leu Val Gln His Val Glu Pro Gly Ser Arg
        355                 360                 365

Ala Glu Arg Gly Arg Leu Arg Arg Asp Asp Arg Ile Leu Glu Ile Asn
        370                 375                 380

Gly Ile Lys Leu Ile Gly Leu Thr Glu Ser Gln Val Gln Glu Gln Leu
385                 390                 395                 400

Arg Arg Ala Leu Glu Ser Ser Glu Leu Arg Val Arg Val Leu Arg Gly
            405                 410                 415

Asp Arg Asn Arg Arg Gln Gln Arg Asp Ser Lys Val Ala Glu Met Val
        420                 425                 430

Glu Val Ala Thr Val Ser Pro Thr Arg Lys Pro His Ala Ala Pro Val
            435                 440                 445

Gly Thr Ser Leu Gln Val Ala Asn Thr Arg Lys Leu Gly Arg Lys Ile
        450                 455                 460

Glu Ile Met Leu Lys Lys Gly Pro Asn Gly Leu Gly Phe Ser Val Thr
465                 470                 475                 480

Thr Arg Asp Asn Pro Ala Gly Gly His Cys Pro Ile Tyr Ile Lys Asn
            485                 490                 495

Ile Leu Pro Arg Gly Ala Ala Ile Glu Asp Gly Arg Leu Lys Pro Gly
            500                 505                 510

Asp Arg Leu Leu Glu Val Asp Gly Thr Pro Met Thr Gly Lys Thr Gln
        515                 520                 525

Thr Asp Val Val Ala Ile Leu Arg Gly Met Pro Ala Gly Ala Thr Val
        530                 535                 540

Arg Ile Val Val Ser Arg Gln Gln Glu Leu Ala Glu Gln Ala Asp Gln
545                 550                 555                 560
```

```
Pro Ala Glu Lys Ser Ala Gly Val Ala Val Ala Pro Ser Val Ala Pro
            565                 570                 575
Pro Ala Val Pro Ala Ala Ala Pro Ala Pro Ile Pro Val Gln
        580                 585                 590
Lys Ser Ser Ser Ala Arg Ser Leu Phe Thr His Gln Gln Ser Gln
    595                 600                 605
Leu Asn Glu Ser Gln His Phe Ile Asp Ala Gly Ser Glu Ser Ala Ala
610                 615                 620
Ser Asn Asp Ser Leu Pro Ser Ser Asn Ser Trp His Ser Arg Glu
625                 630                 635                 640
Glu Leu Thr Leu His Ile Pro Val His Asp Thr Glu Lys Ala Gly Leu
                    645                 650                 655
Gly Val Ser Val Lys Gly Lys Thr Cys Ser Asn Leu Asn Ala Ser Gly
                660                 665                 670
Ser Ser Ala Ser Ser Gly Ser Asn Gly Leu Met Lys His Asp Gly Asp
            675                 680                 685
Leu Gly Ile Phe Val Lys Asn Val Ile His Gly Ala Ala Ser Arg
        690                 695                 700
Asp Gly Arg Leu Arg Met Asn Asp Gln Leu Leu Ser Val Asn Gly Val
705                 710                 715                 720
Ser Leu Arg Gly Gln Asn Asn Ala Glu Ala Met Glu Thr Leu Arg Arg
                    725                 730                 735
Ala Met Val Asn Thr Pro Gly Lys His Pro Gly Thr Ile Thr Leu Leu
                740                 745                 750
Val Gly Arg Lys Ile Leu Arg Ser Ala Ser Ser Asp Ile Leu Asp
            755                 760                 765
His Ser Asn Ser His Ser His Ser His Ser Asn Ser Ser Gly Gly Ser
        770                 775                 780
Asn Ser Asn Gly Ser Gly Asn Asn Asn Ser Ser Asn Ala Ser
785                 790                 795                 800
Asp Asn Ser Gly Ala Thr Val Ile Tyr Leu Ser Pro Glu Lys Arg Glu
                    805                 810                 815
Gln Arg Cys Asn Gly Gly Gly Gly Gly Ser Ala Gly Asn Glu Met
                820                 825                 830
Asn Arg Trp Ser Asn Pro Val Leu Asp Arg Leu Thr Gly Gly Ile Cys
            835                 840                 845
Ser Ser Asn Ser Ala Gln Pro Ser Ser Gln Gln Ser His Gln Gln Gln
        850                 855                 860
Pro His Pro Ser Gln Gln Gln Gln Gln Arg Arg Leu Pro Ala Ala
865                 870                 875                 880
Pro Val Cys Ser Ala Ala Leu Arg Asn Glu Ser Tyr Tyr Met Ala
                    885                 890                 895
Thr Asn Asp Asn Trp Ser Pro Ala Gln Met His Leu Met Thr Ala His
                900                 905                 910
Gly Asn Thr Ala Leu Leu Ile Glu Asp Asp Ala Glu Pro Met Ser Pro
            915                 920                 925
Thr Leu Pro Ala Arg Pro His Asp Gly Gln His Cys Asn Thr Ser Ser
        930                 935                 940
Ala Asn Pro Ser Gln Asn Leu Ala Val Gly Asn Gln Gly Pro Pro Ile
945                 950                 955                 960
Asn Thr Val Pro Gly Thr Pro Ser Thr Ser Asn Phe Asp Ala Thr
                    965                 970                 975
Tyr Ser Ser Gln Leu Ser Leu Glu Thr Asn Ser Gly Val Glu His Phe
```

```
                980              985              990
Ser Arg Asp Ala Leu Gly Arg Arg  Ser Ile Ser Glu Lys  His His Ala
            995              1000             1005

Ala Leu Asp Ala Arg Glu Thr  Gly Thr Tyr Gln Arg  Asn Lys Lys
    1010            1015             1020

Leu Arg Glu Glu Arg Glu Arg  Glu Arg Arg Ile Gln  Leu Thr Lys
    1025            1030             1035

Ser Ala Val Tyr Gly Gly Ser  Ile Glu Ser Leu Thr  Ala Arg Ile
    1040            1045             1050

Ala Ser Ala Asn Ala Gln Phe  Ser Gly Tyr Lys His  Ala Lys Thr
    1055            1060             1065

Ala Ser Ser Ile Glu Gln Arg  Glu Thr Gln Gln Gln  Leu Ala Ala
    1070            1075             1080

Ala Glu Ala Glu Ala Arg Asp  Gln Leu Gly Asp Leu  Gly Pro Ser
    1085            1090             1095

Leu Gly Met Lys Lys Ser Ser  Ser Leu Glu Ser Leu  Gln Thr Met
    1100            1105             1110

Val Gln Glu Leu Gln Met Ser  Asp Glu Pro Arg Gly  His Gln Ala
    1115            1120             1125

Leu Arg Ala Pro Arg Gly Arg  Gly Arg Glu Asp Ser  Leu Arg Ala
    1130            1135             1140

Ala Val Val Ser Glu Pro Asp  Ala Ser Lys Pro Arg  Lys Thr Trp
    1145            1150             1155

Leu Leu Glu Asp Gly Asp His  Glu Gly Gly Phe Ala  Ser Gln Arg
    1160            1165             1170

Asn Gly Pro Phe Gln Ser Ser  Leu Asn Asp Gly Lys  His Gly Cys
    1175            1180             1185

Lys Ser Ser Arg Ala Lys Lys  Pro Ser Ile Leu Arg  Gly Ile Gly
    1190            1195             1200

His Met Phe Arg Phe Gly Lys  Asn Arg Lys Asp Gly  Val Val Pro
    1205            1210             1215

Val Asp Asn Tyr Ala Val Asn  Ile Ser Pro Pro Thr  Ser Val Val
    1220            1225             1230

Ser Thr Ala Thr Ser Pro Gln  Leu Gln Gln Gln Gln  Gln Gln Gln
    1235            1240             1245

Leu Gln Gln His Gln Gln Gln  Gln Gln Ile Pro Thr  Ala Ala Leu
    1250            1255             1260

Ala Ala Leu Glu Arg Asn Gly  Lys Pro Pro Ala Tyr  Gln Pro Pro
    1265            1270             1275

Pro Pro Leu Pro Ala Pro Asn  Gly Val Gly Ser Asn  Gly Ile His
    1280            1285             1290

Gln Asn Asp Ile Phe Asn His  Arg Tyr Gln His Tyr  Ala Asn Tyr
    1295            1300             1305

Glu Asp Leu His Gln Gln His  Gln Gln His Gln Ile  Ser Gly Gly
    1310            1315             1320

Asp Ser Thr Thr Ser Ile Ser  Glu Thr Leu Ser Glu  Ser Thr Leu
    1325            1330             1335

Glu Cys Met Arg Gln Gln Val  Ile Arg Gln Arg Ile  Lys Val Glu
    1340            1345             1350

Ala Glu Ser Arg Arg His Gln  His Tyr His Ser Gln  Arg Ser Ala
    1355            1360             1365

Arg Ser Gln Asp Val Ser Met  His Ser Thr Ser Ser  Gly Ser Gln
    1370            1375             1380
```

-continued

```
Pro Gly Ser Leu Ala Gln Pro Gln Ala Gln Ser Asn Gly Val Arg
    1385                1390                1395
Pro Met Ser Ser Tyr Tyr Glu Tyr Glu Thr Val Gln Gln Gln Arg
    1400                1405                1410
Val Gly Ser Ile Lys His Ser His Ser Ser Ser Ala Thr Ser Ser
    1415                1420                1425
Ser Ser Ser Pro Ile Asn Val Pro His Trp Lys Ala Ala Ala Met
    1430                1435                1440
Asn Gly Tyr Ser Pro Ala Ser Leu Asn Ser Ser Ala Arg Ser Arg
    1445                1450                1455
Gly Pro Phe Val Thr Gln Val Thr Ile Arg Glu Gln Ser Ser Gly
    1460                1465                1470
Gly Ile Pro Ala His Leu Leu Gln Gln His Gln Gln Gln Leu
    1475                1480                1485
Gln Gln Gln Gln Pro Thr Tyr Gln Thr Val Gln Lys Met Ser Gly
    1490                1495                1500
Pro Ser Gln Tyr Gly Ser Ala Ala Gly Ser Gln Pro His Ala Ser
    1505                1510                1515
Lys Val
    1520

<210> SEQ ID NO 3
<211> LENGTH: 351
<212> TYPE: PRT
<213> ORGANISM: Drosophila melanogaster

<400> SEQUENCE: 3

Met Ser Lys Asn Lys Ile Asn Thr Thr Ser Ala Thr Ala Ala Ser Asp
1               5                   10                  15
Thr Asn Leu Ile Glu Val Lys Ser Lys Phe Asp Ala Glu Phe Arg Arg
                20                  25                  30
Trp Ser Phe Lys Arg Asn Glu Ala Glu Gln Ser Phe Asp Lys Phe Ala
            35                  40                  45
Ser Leu Ile Glu Gln Leu His Lys Leu Thr Asn Ile Gln Phe Leu Ile
        50                  55                  60
Leu Tyr Ile Asp Pro Arg Asp Asn Asp Leu Leu Pro Ile Asn Asn Asp
65                  70                  75                  80
Asp Asn Phe Gly Arg Ala Leu Lys Thr Ala Arg Pro Leu Leu Arg Val
                85                  90                  95
Ile Val Gln Arg Lys Asp Asp Leu Asn Glu Tyr Ser Gly Phe Gly Thr
            100                 105                 110
Met Lys Pro Arg Asn Leu Ile Gly Ser Ile Leu Met Gly His Thr Pro
        115                 120                 125
Val Lys Thr Lys Ala Pro Ser Ile Ser Ile Pro His Asp Phe Arg Gln
    130                 135                 140
Val Ser Ala Ile Ile Asp Val Asp Ile Val Pro Glu Thr His Arg Arg
145                 150                 155                 160
Val Arg Leu Leu Lys His Gly Ser Asp Lys Pro Leu Gly Phe Tyr Ile
                165                 170                 175
Arg Asp Gly Thr Ser Val Arg Val Thr Ala Ser Gly Leu Glu Lys Gln
            180                 185                 190
Pro Gly Ile Phe Ile Ser Arg Leu Val Pro Gly Gly Leu Ala Glu Ser
        195                 200                 205
Thr Gly Leu Leu Ala Val Asn Asp Glu Val Ile Glu Val Asn Gly Ile
```

```
            210                 215                 220
Glu Val Ala Gly Lys Thr Leu Asp Gln Val Thr Asp Met Met Val Ala
225                 230                 235                 240

Asn Ser Ser Asn Leu Ile Ile Thr Val Lys Pro Ala Asn Gln Arg Thr
                245                 250                 255

Leu Thr Ser Thr His Arg Gly Ser Phe Ser Arg Asn Ser Gln Leu Ser
            260                 265                 270

Ser Gly Ser His His Thr Asn Asn Thr Asn Thr Ser Asp Glu Ile Glu
        275                 280                 285

His Asp Asp Gln Asp Asp Ile Val Asp Leu Thr Gly Val Thr Leu Asp
    290                 295                 300

Glu Ser Pro Thr Ser Thr Ser Ala Gly Asn His Asn His Gln Pro Pro
305                 310                 315                 320

Leu Ser Ser Ser Pro Ser Ser His His Gln Gln Ala Ala Ser Asn Ala
                325                 330                 335

Ser Thr Ile Met Ala Ser Asp Val Lys Asp Gly Val Leu His Leu
                340                 345                 350
```

<210> SEQ ID NO 4
<211> LENGTH: 191
<212> TYPE: PRT
<213> ORGANISM: Drosophila melanogaster

<400> SEQUENCE: 4

```
Met Gln Thr Ile Lys Cys Val Val Asp Asp Gly Ala Val Gly Lys
1               5                   10                  15

Thr Cys Leu Leu Ile Ser Tyr Thr Thr Asn Lys Phe Pro Ser Glu Tyr
                20                  25                  30

Val Pro Thr Val Phe Asp Asn Tyr Ala Val Thr Val Met Ile Gly Gly
            35                  40                  45

Glu Pro Tyr Thr Leu Gly Leu Phe Asp Thr Ala Gly Gln Glu Asp Tyr
        50                  55                  60

Asp Arg Leu Arg Pro Leu Ser Tyr Pro Gln Thr Asp Val Phe Leu Val
65                  70                  75                  80

Cys Phe Ser Val Val Ser Pro Ser Ser Phe Glu Asn Val Lys Glu Lys
                85                  90                  95

Trp Val Pro Glu Ile Thr His His Cys Gln Lys Thr Pro Phe Leu Leu
                100                 105                 110

Val Gly Thr Gln Ile Asp Leu Arg Asp Glu Asn Ser Thr Leu Glu Lys
            115                 120                 125

Leu Ala Lys Asn Lys Gln Lys Pro Ile Thr Met Glu Gln Gly Glu Lys
130                 135                 140

Leu Ala Lys Glu Leu Lys Ala Val Lys Tyr Val Glu Cys Ser Ala Leu
145                 150                 155                 160

Thr Gln Lys Gly Leu Lys Asn Val Phe Asp Glu Ala Ile Leu Ala Ala
                165                 170                 175

Leu Glu Pro Pro Glu Pro Thr Lys Lys Arg Lys Cys Lys Phe Leu
                180                 185                 190
```

<210> SEQ ID NO 5
<211> LENGTH: 1507
<212> TYPE: PRT
<213> ORGANISM: Drosophila melanogaster

<400> SEQUENCE: 5

Met Ser Thr Ser Val Gln Arg Met Ser Arg Ser Tyr His Cys Ile Asn

-continued

```
1               5                   10                  15

Met Ser Ala Thr Pro Gln Ala Gly His Leu Asn Pro Ala Gln Gln Gln
                20                  25                  30

Thr His Gln Gln His Lys Arg Lys Cys Arg Asp Leu Gly Arg Arg Leu
                35                  40                  45

Ile Pro Ala Arg Leu Leu Leu Gly Val Ile Val Ala Ile Ser Leu Leu
50                      55                  60

Ser Pro Ala Leu Ala Leu His Ser Pro Pro Asp Lys Asn Phe Ser Gly
65                  70                  75                  80

Asp Asn Arg Lys Pro Ala Phe Lys Asn Cys Ala Gly Tyr Ala Pro Lys
                85                  90                  95

Val Lys Glu Glu Gln Pro Glu Asn Thr Tyr Val Leu Thr Val Glu Ala
                100                 105                 110

Val Asp Pro Asp Pro Asp Gln Val Ile Arg Tyr Ser Ile Val Gln Ser
                115                 120                 125

Pro Phe Glu Arg Pro Lys Phe Phe Ile Asn Pro Ser Thr Gly Val Ile
130                     135                 140

Phe Thr Thr His Thr Phe Asp Arg Asp Glu Pro Ile His Glu Lys Phe
145                 150                 155                 160

Val Phe Val Thr Val Gln Ala Thr Asp Asn Gly Leu Pro Pro Leu Asp
                165                 170                 175

Asp Val Cys Thr Phe Asn Val Thr Ile Glu Asp Ile Asn Asp Asn Ala
                180                 185                 190

Pro Ala Phe Asn Lys Ala Arg Tyr Asp Glu Ser Met Ser Glu Asn Ala
                195                 200                 205

Gln Pro Asp Ala Val Val Met Thr Ile Ser Ala Ser Asp Phe Asp Asp
                210                 215                 220

Gly Asn Asn Ser Leu Val Glu Tyr Glu Ile Leu Arg Glu Arg Asp Phe
225                 230                 235                 240

Gln Tyr Phe Lys Ile Asp Lys Glu Ser Gly Ile Ile Tyr Leu Lys Arg
                245                 250                 255

Pro Ile Asp Lys Arg Pro Gly Gln Ser Tyr Ala Ile Ile Val Arg Ala
                260                 265                 270

Tyr Asn Val Val Pro Asp Pro Gln Asp Ala Gln Ile Glu Val Arg
                275                 280                 285

Ile Arg Val Val Glu Ser Ser Ile Lys Pro Pro Ser Phe Val Asn Pro
                290                 295                 300

Ile Asp Thr Pro Ile Tyr Leu Lys Glu Asn Leu Lys Asn Phe Thr His
305                 310                 315                 320

Pro Ile Ala Thr Leu Arg Ala Val Ser Asn Met Pro Asp Lys Pro Glu
                325                 330                 335

Val Ile Phe Glu Leu Asn Thr Gly Arg Thr Glu Gln Thr Asn Ser Lys
                340                 345                 350

Asn Thr Phe Val Phe Asn Gln Ile Gly Asn Glu Val Thr Ile Ser Leu
                355                 360                 365

Gly Lys Thr Leu Asp Tyr Glu Ala Ile Thr Asp Tyr Thr Leu Thr Met
370                 375                 380

Ile Val Arg Asn Thr His Glu Leu Gly Thr Glu His Gln Ile Lys Ile
385                 390                 395                 400

Gln Val Glu Asp Val Asn Asp Asn Ile Pro Tyr Tyr Thr Glu Val Lys
                405                 410                 415

Ser Gly Thr Ile Leu Glu Asn Glu Pro Pro Gly Thr Pro Val Met Gln
                420                 425                 430
```

```
Val Arg Ala Phe Asp Met Asp Gly Thr Ser Ala Asn Ile Val Ser
        435                 440                 445

Phe Glu Leu Ala Asp Asn Arg Glu Tyr Phe Thr Ile Asp Pro Asn Thr
    450                 455                 460

Gly Asn Ile Thr Ala Leu Thr Thr Phe Asp Arg Glu Arg Asp Phe
465                 470                 475                 480

Tyr Asn Val Lys Val Ile Ala Ser Asp Asn Ser Pro Ser Ser Leu Phe
            485                 490                 495

Asp Asn Gly Glu Pro Asn Arg Gly His Gln Val Phe Arg Ile Ser Ile
                500                 505                 510

Gly Asp Lys Asn Asp His Lys Pro His Phe Gln Gln Asp Lys Tyr Leu
            515                 520                 525

Ala Glu Arg Leu Leu Glu Asp Ala Asn Thr Asn Thr Glu Val Ile Glu
            530                 535                 540

Val Lys Ala Glu Asp Glu Asp Asn Ala Ser Gln Ile Leu Tyr Ser Ile
545                 550                 555                 560

Glu Ser Gly Asn Val Gly Asp Ala Phe Lys Ile Gly Leu Lys Thr Gly
                565                 570                 575

Lys Ile Thr Val Asn Gln Lys Leu Asp Tyr Glu Thr Ile Thr Glu Tyr
            580                 585                 590

Glu Leu Lys Val Arg Ala Phe Asp Gly Ile Tyr Asp Asp Tyr Thr Thr
            595                 600                 605

Val Val Ile Lys Ile Glu Asp Val Asn Asp Asn Pro Pro Val Phe Lys
610                 615                 620

Gln Asp Tyr Ser Val Thr Ile Leu Glu Glu Thr Thr Tyr Asp Asp Cys
625                 630                 635                 640

Ile Leu Thr Val Glu Ala Tyr Asp Pro Asp Ile Lys Asp Arg Asn Ala
                645                 650                 655

Asp Gln His Ile Val Tyr Ser Ile His Gln Asn Asp Gly Asn Arg Trp
                660                 665                 670

Thr Ile Asp Asn Ser Gly Cys Leu Arg Leu Val Lys Thr Leu Asp Arg
    675                 680                 685

Asp Pro Pro Asn Gly His Lys Asn Trp Gln Val Leu Ile Lys Ala Asn
    690                 695                 700

Asp Glu Asp Gly Val Gly Thr Thr Val Ser Thr Val Lys Glu Val Thr
705                 710                 715                 720

Val Thr Leu Lys Asp Ile Asn Asp Asn Ala Pro Phe Leu Ile Asn Glu
            725                 730                 735

Met Pro Val Tyr Trp Gln Glu Asn Arg Asn Pro Gly His Val Val Gln
                740                 745                 750

Leu Gln Ala Asn Asp Tyr Asp Asp Thr Pro Gly Ala Gly Asn Phe Thr
            755                 760                 765

Phe Gly Ile Asp Ser Glu Ala Thr Pro Asp Ile Lys Thr Lys Phe Ser
    770                 775                 780

Met Asp Gly Asp Tyr Leu His Ala Asn Val Gln Phe Asp Arg Glu Ala
785                 790                 795                 800

Gln Lys Glu Tyr Phe Ile Pro Ile Arg Ile Ser Asp Ser Gly Val Pro
                805                 810                 815

Arg Gln Ser Ala Val Ser Ile Leu His Leu Val Ile Gly Asp Val Asn
            820                 825                 830

Asp Asn Ala Met Ser Glu Gly Ser Ser Arg Ile Phe Ile Tyr Asn Tyr
    835                 840                 845
```

```
Lys Gly Glu Ala Pro Glu Thr Asp Ile Gly Arg Val Phe Val Asp Asp
850                 855                 860

Leu Asp Asp Trp Asp Leu Glu Asp Lys Tyr Phe Glu Trp Lys Asp Leu
865                 870                 875                 880

Pro His Asp Gln Phe Arg Leu Asn Pro Ser Thr Gly Met Ile Thr Met
                885                 890                 895

Leu Val His Thr Ala Glu Gly Glu Tyr Asp Leu Ser Phe Val Val Thr
                900                 905                 910

Glu Asp Ser Met Phe Val Pro Arg His Ser Val Asp Ala Tyr Val Thr
                915                 920                 925

Val Val Val Arg Glu Leu Pro Glu Glu Ala Val Asp Lys Ser Gly Ser
930                 935                 940

Ile Arg Phe Ile Asn Val Thr Lys Glu Glu Phe Ile Ser Val Pro Arg
945                 950                 955                 960

Asp Phe Gln Ser Pro Asp Ala Leu Ser Leu Lys Asp Arg Phe Gln Leu
                965                 970                 975

Ser Leu Ala Lys Leu Phe Asn Thr Ser Val Ser Asn Val Asp Val Phe
                980                 985                 990

Thr Val Leu Gln Asn Glu Asn His Thr Leu Asp Val Arg Phe Ser Ala
                995                 1000                1005

His Gly Ser Pro Tyr Tyr Ala Pro Glu Lys Leu Asn Gly Ile Val
    1010                1015                1020

Ala Gln Asn Gln Gln Arg Leu Glu Asn Glu Leu Asp Leu Gln Met
    1025                1030                1035

Leu Met Val Asn Ile Asp Glu Cys Leu Ile Glu Lys Phe Lys Cys
    1040                1045                1050

Glu Glu Ser Cys Thr Asn Glu Leu His Lys Ser Ser Val Pro Tyr
    1055                1060                1065

Met Ile Tyr Ser Asn Thr Thr Ser Phe Val Gly Val Asn Ala Phe
    1070                1075                1080

Val Gln Ala Gln Cys Val Cys Glu Ala Pro Leu Met Arg Arg Cys
    1085                1090                1095

Leu Asn Gly Gly Ser Pro Arg Tyr Gly Glu Asn Asp Val Cys Asp
    1100                1105                1110

Cys Ile Asp Gly Phe Thr Gly Pro His Cys Glu Leu Val Ser Val
    1115                1120                1125

Ala Phe Tyr Gly Ser Gly Tyr Ala Phe Tyr Glu Pro Ile Ala Ala
    1130                1135                1140

Cys Asn Asn Thr Lys Ile Ser Leu Glu Ile Thr Pro Gln Ile Asp
    1145                1150                1155

Gln Gly Leu Ile Met Tyr Leu Gly Pro Leu Asn Phe Asn Pro Leu
    1160                1165                1170

Leu Ala Ile Ser Asp Phe Leu Ala Leu Glu Leu Asp Asn Gly Tyr
    1175                1180                1185

Pro Val Leu Thr Val Asp Tyr Gly Ser Gly Ala Ile Arg Ile Arg
    1190                1195                1200

His Gln His Ile Lys Met Val Ala Asp Arg Thr Tyr Gln Leu Asp
    1205                1210                1215

Ile Ile Leu Gln Arg Thr Ser Ile Glu Met Thr Val Asp Asn Cys
    1220                1225                1230

Arg Leu Ser Thr Cys Gln Leu Gly Ala Pro Ile Gly Pro Asn
    1235                1240                1245

Glu Phe Leu Asn Val Asn Ala Pro Leu Gln Leu Gly Gly Thr Pro
```

-continued

```
            1250                1255                1260

Val Asp Leu Glu Gln Leu Gly Arg Gln Leu Asn Trp Thr His Val
    1265                1270                1275

Pro Asn Gln Lys Gly Phe Phe Gly Cys Ile Arg Asn Leu Thr Ile
    1280                1285                1290

Asn Glu Gln Thr Tyr Asn Leu Gly Met Pro Ser Val Phe Arg Asn
    1295                1300                1305

Ile Asp Ser Gly Cys Gln Gln Ser Val Ala Val Ala Phe Ser Phe
    1310                1315                1320

Gly Ile Asp Arg Asn Phe Ile Ala Ile Ile Val Cys Leu Ala
    1325                1330                1335

Leu Leu Leu Ile Ile Leu Leu Ala Val Val Val Gln Lys Lys Gln
    1340                1345                1350

Lys Asn Gly Trp His Glu Lys Asp Ile Asp Asp Ile Arg Glu Thr
    1355                1360                1365

Ile Ile Asn Tyr Glu Asp Glu Gly Gly Gly Glu Arg Asp Thr Asp
    1370                1375                1380

Tyr Asp Leu Asn Val Leu Arg Thr Gln Pro Phe Tyr Glu Glu Lys
    1385                1390                1395

Leu Tyr Lys Asp Pro His Ala Leu Gln Gly Asn Met Arg Asp Pro
    1400                1405                1410

Asn Asp Ile Pro Asp Ile Ala Asp Phe Leu Gly Asp Lys Lys Glu
    1415                1420                1425

Asn Cys Asp Arg Asp Val Gly Ala Thr Thr Val Asp Asp Val Arg
    1430                1435                1440

His Tyr Ala Tyr Glu Gly Asp Gly Asn Ser Asp Gly Ser Leu Ser
    1445                1450                1455

Ser Leu Ala Ser Cys Thr Asp Asp Gly Asp Leu Asn Phe Asp Tyr
    1460                1465                1470

Leu Ser Asn Phe Gly Pro Arg Phe Arg Lys Leu Ala Asp Met Tyr
    1475                1480                1485

Gly Glu Glu Pro Ser Asp Thr Asp Ser Asn Val Asp Asp Asp Gln
    1490                1495                1500

Gly Trp Arg Ile
    1505

<210> SEQ ID NO 6
<211> LENGTH: 2146
<212> TYPE: PRT
<213> ORGANISM: Drosophila melanogaster

<400> SEQUENCE: 6

Met Ala Lys Ile Ala Asn Ala Ser Leu Ser Gln Gln Gln Lys Gln Arg
1               5                   10                  15

Gln Ala Glu Thr Ala Thr Thr Thr Thr Thr Val Ala Ala Ser Val
            20                  25                  30

Glu Thr Ala Thr Thr Thr Ala Arg Ser Arg Asp Arg Thr Lys Ser Ala
        35                  40                  45

Ala Gln Ile Thr Ser His Leu Leu Lys Arg Ala Ile Ser Val Tyr Ser
    50                  55                  60

Ser Pro Gln Trp Ile Pro Leu Phe Ile Leu Ile Tyr Leu Ala Thr Asp
65                  70                  75                  80

Val Ala Ser Val Ala Val Pro Thr Lys Glu Ala Tyr Phe Asn Gly Ser
                85                  90                  95
```

```
Thr Tyr Leu Arg Leu Thr Thr Pro Met Pro Ile Trp Asp His Ser Ala
            100                 105                 110
Ile Ser Phe Arg Ser Cys Arg Gly Gly Glu Ile Leu Ala Gln Gln Tyr
        115                 120                 125
Asn Lys Asn Ser Ile Val Ile Ser Val Leu Asn Asp Phe Leu Gln Ile
    130                 135                 140
Ser Leu Ala Gly Pro Ala Val His Gly Pro Asn Asn Arg Leu Asp Val
145                 150                 155                 160
Lys Leu Pro Tyr Gln Leu Leu Asp Asn Arg Trp His Thr Leu Gln Phe
                165                 170                 175
Lys Tyr Glu Tyr Gly Asn Leu Tyr Leu His Val Asp Arg Ala Ala Ser
            180                 185                 190
Ile Phe Ala Asn Ser Thr Tyr Asn Ser Gln Phe Leu Thr Asn Gln Asp
        195                 200                 205
Ile Gly Tyr Lys Asp Ala Ile Leu Ile Leu Gly Asn Ser Phe Ser Gly
    210                 215                 220
Cys Leu Leu Asp Gly Pro Gly Leu Gln Phe Val Asn Asn Ser Thr Val
225                 230                 235                 240
Gln Asn Val Val Phe Gly His Cys Pro Leu Thr Pro Gly Pro Cys Ser
                245                 250                 255
Asp His Asp Leu Phe Thr Arg Leu Pro Asp Asn Phe Cys Leu Asn Asp
            260                 265                 270
Pro Cys Met Gly His Gly Thr Cys Ser Ser Ser Pro Glu Gly Tyr Glu
        275                 280                 285
Cys Arg Cys Thr Ala Arg Tyr Ser Gly Lys Asn Cys Gln Lys Asp Asn
    290                 295                 300
Gly Ser Pro Cys Ala Lys Asn Pro Cys Glu Asn Gly Gly Ser Cys Leu
305                 310                 315                 320
Glu Asn Ser Arg Gly Asp Tyr Gln Cys Phe Cys Asp Pro Asn His Ser
                325                 330                 335
Gly Gln His Cys Glu Thr Glu Val Asn Ile His Pro Leu Cys Gln Thr
            340                 345                 350
Asn Pro Cys Leu Asn Asn Gly Ala Cys Val Val Ile Gly Gly Ser Gly
        355                 360                 365
Ala Leu Thr Cys Glu Cys Pro Lys Gly Tyr Ala Gly Ala Arg Cys Glu
    370                 375                 380
Val Asp Thr Asp Glu Cys Ala Ser Gln Pro Cys Gln Asn Asn Gly Ser
385                 390                 395                 400
Cys Ile Asp Arg Ile Asn Gly Phe Ser Cys Asp Cys Ser Gly Thr Gly
                405                 410                 415
Tyr Thr Gly Ala Phe Cys Gln Thr Asn Val Asp Glu Cys Asp Lys Asn
            420                 425                 430
Pro Cys Leu Asn Gly Gly Arg Cys Phe Asp Thr Tyr Gly Trp Tyr Thr
        435                 440                 445
Cys Gln Cys Leu Asp Gly Trp Gly Gly Glu Ile Cys Asp Arg Pro Met
    450                 455                 460
Thr Cys Gln Thr Gln Gln Cys Leu Asn Gly Gly Thr Cys Leu Asp Lys
465                 470                 475                 480
Pro Ile Gly Phe Gln Cys Leu Cys Pro Pro Glu Tyr Thr Gly Glu Leu
                485                 490                 495
Cys Gln Ile Ala Pro Ser Cys Ala Gln Gln Cys Pro Ile Asp Ser Glu
            500                 505                 510
Cys Val Gly Gly Lys Cys Val Cys Lys Pro Gly Ser Ser Gly Tyr Asn
```

515                 520                 525
Cys Gln Thr Ser Thr Gly Asp Gly Ala Ser Ala Leu Ala Leu Thr Pro
            530                 535                 540
Ile Asn Cys Asn Ala Thr Asn Gly Lys Cys Leu Asn Gly Gly Thr Cys
545                 550                 555                 560
Ser Met Asn Gly Thr His Cys Tyr Cys Ala Val Gly Tyr Ser Gly Asp
                565                 570                 575
Arg Cys Glu Lys Ala Glu Asn Cys Ser Pro Leu Asn Cys Gln Glu Pro
            580                 585                 590
Met Val Cys Val Gln Asn Gln Cys Leu Cys Pro Glu Asn Lys Val Cys
            595                 600                 605
Asn Gln Cys Ala Thr Gln Pro Cys Gln Asn Gly Gly Glu Cys Val Asp
            610                 615                 620
Leu Pro Asn Gly Asp Tyr Glu Cys Lys Cys Thr Arg Gly Trp Thr Gly
625                 630                 635                 640
Arg Thr Cys Gly Asn Asp Val Asp Glu Cys Thr Leu His Pro Lys Ile
                645                 650                 655
Cys Gly Asn Gly Ile Cys Lys Asn Glu Lys Gly Ser Tyr Lys Cys Tyr
            660                 665                 670
Cys Thr Pro Gly Phe Thr Gly Val His Cys Asp Ser Asp Val Asp Glu
            675                 680                 685
Cys Leu Ser Phe Pro Cys Leu Asn Gly Ala Thr Cys His Asn Lys Ile
            690                 695                 700
Asn Ala Tyr Glu Cys Val Cys Gln Pro Gly Tyr Glu Gly Glu Asn Cys
705                 710                 715                 720
Glu Val Asp Ile Asp Glu Cys Gly Ser Asn Pro Cys Ser Asn Gly Ser
                725                 730                 735
Thr Cys Ile Asp Arg Ile Asn Asn Phe Thr Cys Asn Cys Ile Pro Gly
            740                 745                 750
Met Thr Gly Arg Ile Cys Asp Ile Asp Ile Asp Asp Cys Val Gly Asp
            755                 760                 765
Pro Cys Leu Asn Gly Gly Gln Cys Ile Asp Gln Leu Gly Gly Phe Arg
770                 775                 780
Cys Asp Cys Ser Gly Thr Gly Tyr Glu Gly Glu Asn Cys Glu Leu Asn
785                 790                 795                 800
Ile Asp Glu Cys Leu Ser Asn Pro Cys Thr Asn Gly Ala Lys Cys Leu
                805                 810                 815
Asp Arg Val Lys Asp Tyr Phe Cys Asp Cys His Asn Gly Tyr Lys Gly
            820                 825                 830
Lys Asn Cys Glu Gln Asp Ile Asn Glu Cys Glu Ser Asn Pro Cys Gln
            835                 840                 845
Tyr Asn Gly Asn Cys Leu Glu Arg Ser Asn Ile Thr Leu Tyr Gln Met
            850                 855                 860
Ser Arg Ile Thr Asp Leu Pro Lys Val Phe Ser Gln Pro Phe Ser Phe
865                 870                 875                 880
Glu Asn Ala Ser Gly Tyr Glu Cys Val Cys Val Pro Gly Ile Ile Gly
                885                 890                 895
Lys Asn Cys Glu Ile Asn Ile Asn Glu Cys Asp Ser Asn Pro Cys Ser
            900                 905                 910
Lys His Gly Asn Cys Asn Asp Gly Ile Gly Thr Tyr Thr Cys Glu Cys
            915                 920                 925
Glu Pro Gly Phe Glu Gly Thr His Cys Glu Ile Asn Ile Asp Glu Cys
            930                 935                 940

```
Asp Arg Tyr Asn Pro Cys Gln Arg Gly Thr Cys Tyr Asp Gln Ile Asp
945                 950                 955                 960

Asp Tyr Asp Cys Asp Cys Asp Ala Asn Tyr Gly Gly Lys Asn Cys Ser
            965                 970                 975

Val Leu Leu Lys Gly Cys Asp Gln Asn Pro Cys Leu Asn Gly Gly Ala
        980                 985                 990

Cys Leu Pro Tyr Leu Ile Asn Glu Val Thr His Leu Tyr Asn Cys Thr
        995                 1000                1005

Cys Glu Asn Gly Phe Gln Gly Asp Lys Cys Glu Lys Thr Thr Thr
    1010                1015                1020

Leu Ser Met Val Ala Thr Ser Leu Ile Ser Val Thr Thr Glu Arg
    1025                1030                1035

Glu Glu Gly Tyr Asp Ile Asn Leu Gln Phe Arg Thr Thr Leu Pro
    1040                1045                1050

Asn Gly Val Leu Ala Phe Gly Thr Thr Gly Glu Lys Asn Glu Pro
    1055                1060                1065

Val Ser Tyr Ile Leu Glu Leu Ile Asn Gly Arg Leu Asn Leu His
    1070                1075                1080

Ser Ser Leu Leu Asn Lys Trp Glu Gly Val Phe Ile Gly Ser Lys
    1085                1090                1095

Leu Asn Asp Ser Asn Trp His Lys Val Phe Val Ala Ile Asn Thr
    1100                1105                1110

Ser His Leu Val Leu Ser Ala Asn Asp Glu Gln Ala Ile Phe Pro
    1115                1120                1125

Val Gly Ser Tyr Glu Thr Ala Asn Asn Ser Gln Pro Ser Phe Pro
    1130                1135                1140

Arg Thr Tyr Leu Gly Gly Thr Ile Pro Asn Leu Lys Ser Tyr Leu
    1145                1150                1155

Arg His Leu Thr His Gln Pro Ser Ala Phe Val Gly Cys Met Gln
    1160                1165                1170

Asp Ile Met Val Asn Gly Lys Trp Ile Phe Pro Asp Glu Gln Asp
    1175                1180                1185

Ala Asn Ile Ser Tyr Thr Lys Leu Glu Asn Val Gln Ser Gly Cys
    1190                1195                1200

Pro Arg Thr Glu Gln Cys Lys Pro Asn Pro Cys His Ser Asn Gly
    1205                1210                1215

Glu Cys Thr Asp Leu Trp His Thr Phe Ala Cys His Cys Pro Arg
    1220                1225                1230

Pro Phe Phe Gly His Thr Cys Gln His Asn Met Thr Ala Ala Thr
    1235                1240                1245

Phe Gly His Glu Asn Thr Thr His Ser Ala Val Ile Val Glu Thr
    1250                1255                1260

Thr Asp Val Ala Arg Arg Ala Ile Arg Ser Ile Leu Asp Ile Ser
    1265                1270                1275

Met Phe Ile Arg Thr Arg Glu Pro Thr Gly Gln Val Phe Tyr Leu
    1280                1285                1290

Gly Thr Asp Pro Arg Lys Ala Pro Thr Lys Asn Ile Gly Asp Ser
    1295                1300                1305

Tyr Val Ala Ala Lys Leu His Gly Gly Glu Leu Leu Val Lys Met
    1310                1315                1320

Gln Phe Ser Gly Thr Pro Glu Ala Tyr Thr Val Gly Gly Gln Lys
    1325                1330                1335
```

Leu Asp Asn Gly Tyr Asn His Leu Ile Glu Val Val Arg Asn Gln
1340                1345                1350

Thr Leu Val Gln Val Lys Leu Asn Gly Thr Glu Tyr Phe Arg Lys
1355                1360                1365

Thr Leu Ser Thr Thr Gly Leu Leu Asp Ala Gln Val Leu Tyr Leu
1370                1375                1380

Gly Gly Pro Ala Pro Thr Arg Glu Ser Leu Leu Gly Ala Thr Thr
1385                1390                1395

Glu Pro Gly Ile Ile Pro Val Pro Gly Ala Gly Ile Pro Ile Glu
1400                1405                1410

Asp Thr Thr Val Pro Lys Glu Ala Asp Ser Arg Asp Tyr Phe
1415                1420                1425

Lys Gly Ile Ile Gln Asp Val Lys Val Ser Asn Gly Ser Leu Asn
1430                1435                1440

Leu Ile Val Glu Met Tyr Ser Leu Asn Val Thr Asp Val Gln Val
1445                1450                1455

Asn Ala Lys Pro Leu Gly Ala Val Thr Ile Asp Arg Ala Ser Val
1460                1465                1470

Leu Pro Gly Glu Val Ser Asp Asp Leu Cys Arg Lys Asn Pro Cys
1475                1480                1485

Leu His Asn Ala Glu Cys Arg Asn Thr Trp Asn Asp Tyr Thr Cys
1490                1495                1500

Lys Cys Pro Asn Gly Tyr Lys Gly Lys Asn Cys Gln Glu Ile Glu
1505                1510                1515

Phe Cys Gln His Val Thr Cys Pro Gly Gln Ser Leu Cys Gln Asn
1520                1525                1530

Leu Asp Asp Gly Tyr Glu Cys Val Thr Asn Thr Thr Phe Thr Gly
1535                1540                1545

Gln Glu Arg Ser Pro Leu Ala Phe Phe Tyr Phe Gln Glu Gln Gln
1550                1555                1560

Ser Asp Asp Ile Val Ser Glu Ala Ser Pro Lys Gln Thr Leu Lys
1565                1570                1575

Pro Val Ile Asp Ile Ala Phe Arg Thr Arg Ala Gly Gly Thr Leu
1580                1585                1590

Leu Tyr Ile Asp Asn Val Asp Gly Phe Phe Glu Ile Gly Val Asn
1595                1600                1605

Gly Gly Arg Val Thr Ile Thr Trp Lys Leu Ser Ala Leu His Phe
1610                1615                1620

Gly Glu Ser Ala Arg Phe Glu Lys Glu Asn Thr Asp Gly Glu Trp
1625                1630                1635

Ser Arg Ile Tyr Leu Arg Ala His Asn Ser Lys Leu Glu Gly Gly
1640                1645                1650

Trp Lys Gly Trp Glu Ser Met Val Asp Pro Thr Pro Ala Phe Ser
1655                1660                1665

Thr Asp Ile Asp Gln Ala Ala Phe Gln Ser Leu Ile Ala Thr Ser
1670                1675                1680

Thr Gln Val Tyr Leu Gly Gly Met Pro Glu Ser Arg Gln Ala Arg
1685                1690                1695

Gly Ser Thr Leu Ser Ala Gln Gln Gly Ser Gln Phe Lys Gly Cys
1700                1705                1710

Val Gly Glu Ala Arg Val Gly Asp Leu Leu Leu Pro Tyr Phe Ser
1715                1720                1725

Met Ala Glu Leu Tyr Ser Arg Thr Asn Val Ser Val Gln Gln Lys

```
                1730                1735                1740
Ala Gln Phe Arg Leu Asn Ala Thr Arg Pro Glu Glu Gly Cys Ile
    1745                1750                1755

Leu Cys Phe Gln Ser Asp Cys Lys Asn Asp Gly Phe Cys Gln Ser
    1760                1765                1770

Pro Ser Asp Glu Tyr Ala Cys Thr Cys Gln Pro Gly Phe Glu Gly
    1775                1780                1785

Asp Asp Cys Gly Thr Asp Ile Asp Glu Cys Leu Asn Thr Glu Cys
    1790                1795                1800

Leu Asn Asn Gly Thr Cys Ile Asn Gln Val Ala Ala Phe Phe Cys
    1805                1810                1815

Gln Cys Gln Pro Gly Phe Glu Gly Gln His Cys Glu Gln Asn Ile
    1820                1825                1830

Asp Glu Cys Ala Asp Gln Pro Cys His Asn Gly Gly Asn Cys Thr
    1835                1840                1845

Asp Leu Ile Ala Ser Tyr Val Cys Asp Cys Pro Glu Asp Tyr Met
    1850                1855                1860

Gly Pro Gln Cys Asp Val Leu Lys Gln Met Thr Cys Glu Asn Glu
    1865                1870                1875

Pro Cys Arg Asn Gly Ser Thr Cys Gln Asn Gly Phe Asn Ala Ser
    1880                1885                1890

Thr Gly Asn Asn Phe Thr Cys Thr Cys Val Pro Gly Phe Glu Gly
    1895                1900                1905

Pro Leu Cys Asp Ile Pro Cys Phe Cys Glu Ile Thr Pro Cys Asp Asn
    1910                1915                1920

Gly Gly Leu Cys Leu Thr Thr Gly Ala Val Pro Met Cys Lys Cys
    1925                1930                1935

Ser Leu Gly Tyr Thr Gly Arg Leu Cys Glu Gln Asp Ile Asn Glu
    1940                1945                1950

Cys Glu Ser Asn Pro Cys Gln Asn Gly Gly Gln Cys Lys Asp Leu
    1955                1960                1965

Val Gly Arg Tyr Glu Cys Asp Cys Gln Gly Thr Gly Phe Glu Gly
    1970                1975                1980

Ile Arg Cys Glu Asn Asp Ile Asp Glu Cys Asn Met Glu Gly Asp
    1985                1990                1995

Tyr Cys Gly Gly Leu Gly Arg Cys Phe Asn Lys Pro Gly Ser Phe
    2000                2005                2010

Gln Cys Ile Cys Gln Lys Pro Tyr Cys Gly Ala Tyr Cys Asn Phe
    2015                2020                2025

Thr Asp Pro Cys Asn Ala Thr Asp Leu Cys Ser Asn Gly Gly Arg
    2030                2035                2040

Cys Val Glu Ser Cys Gly Ala Lys Pro Asp Tyr Tyr Cys Glu Cys
    2045                2050                2055

Pro Glu Gly Phe Ala Gly Lys Asn Cys Thr Ala Pro Ile Thr Ala
    2060                2065                2070

Lys Glu Asp Gly Pro Ser Thr Thr Asp Ile Ala Ile Ile Val Ile
    2075                2080                2085

Pro Val Val Val Leu Leu Leu Ile Ala Gly Ala Leu Leu Gly
    2090                2095                2100

Thr Phe Leu Val Met Ala Arg Asn Lys Arg Ala Thr Arg Gly Thr
    2105                2110                2115

Tyr Ser Pro Ser Ala Gln Glu Tyr Cys Asn Pro Arg Leu Glu Met
    2120                2125                2130
```

```
Asp Asn  Val Leu Lys Pro Pro  Pro Glu Glu Arg Leu  Ile
    2135             2140             2145
```

<210> SEQ ID NO 7
<211> LENGTH: 2019
<212> TYPE: PRT
<213> ORGANISM: Drosophila melanogaster

<400> SEQUENCE: 7

```
Met Gln Ala Asn Ser Ser Arg Ser Asn Leu Ser Ala Gln Ser Ser Gly
1               5                   10                  15

Thr Pro Ser Ala Ser Thr Ile Ser Ser Ser Gln Gly Lys Gln Gln Val
            20                  25                  30

Val Glu Leu Ser Gly Tyr Val Ile Leu Val Glu Asn Val Glu Gly Gly
        35                  40                  45

Lys Ile Lys Leu Tyr Gly Ser Pro Pro Asp Arg Asp Asn Leu Glu Val
    50                  55                  60

Gly Asp Glu Ile Leu Glu Val Asn Gly Leu Thr Leu Glu Asn Ile Ser
65                  70                  75                  80

Arg Thr Glu Val Ile Arg His Ile His Asp Cys Ile Lys Ser Cys Thr
                85                  90                  95

Ile Cys Leu Arg Val Arg Lys Lys Asn Asp Ser Arg Leu Ala Trp Asp
            100                 105                 110

Ile Gly Asn Ser Val Gln Asp Ala Phe Val Ile Ala Val Glu Glu His
        115                 120                 125

Ala Arg Glu Arg Leu Gln Arg Leu Ala Ala Leu Asn Arg Val Thr Pro
    130                 135                 140

Val Asp Ile Thr Gln Leu Ser Lys Lys Leu Gln Gln Thr Lys Ser Gly
145                 150                 155                 160

Thr Ala Thr Ser Gln Arg Gln Asp Leu Ser Phe Leu Asn Glu Ser Thr
                165                 170                 175

Pro Ile Tyr Val Thr Ser Phe Thr Ser Asn Gln Ile Thr Cys Ser Ser
            180                 185                 190

Ser Thr Met Thr Thr Ala Thr Ala Gly Gly Pro Ile Ser Ala Pro Ser
        195                 200                 205

Leu Ala Thr Ala Thr Thr Thr Val Pro Thr Ala Ser Ser His Thr Thr
    210                 215                 220

Thr Val Val Ala Gln Ile Glu His Gly Ala Ser Ala Leu Val Ser Ala
225                 230                 235                 240

Ala Val Ala Ala Ala Thr Ala Asp Arg Asn Ala Asn Ser Thr Thr
                245                 250                 255

Ser Ala Ala Leu Lys Gln Thr Ala Asn Cys Ile Gly Asn Ser Thr Ser
            260                 265                 270

Ser Leu Gly Thr Thr Ser Thr Thr Ser Ser Gln Ser Thr Ser Ser Ala
        275                 280                 285

Thr Gly His Ile Tyr Gln Thr Ser Gln Ala Gln Gln Gln Leu Gln
    290                 295                 300

Gln Leu Gln Gln Gln Leu Ala Ala Ala Ala Ala Gly Lys Pro Leu
305                 310                 315                 320

Gln Ala Lys Ser Leu Leu Ala Ser Ser Leu Gln His Leu Ala Glu Glu
                325                 330                 335

Val Asp Asn Glu Asp Leu Asp Asp Asp Asp Val Asp Gly Ala Asn
            340                 345                 350

Tyr Cys Gly Ile Thr Tyr Ile Ser Tyr Asn Asn Lys His Ala Gln Leu
```

```
                355                 360                 365
Pro Thr Thr Thr Leu Pro Ala Thr Thr Ala Leu Pro Ala Ala Ala Ala
370                 375                 380

Ser Leu Ala Thr Thr Ala Ala Ile Tyr Gln Gln Arg Gln Gln Gln Gln
385                 390                 395                 400

His Gln Gln Gln Gln Gln Gln Gln Gln Pro Val His His His Asn
        405                 410                 415

His Pro Pro Thr Ala Ser Gln Leu Asn Arg Ala Thr Ala Pro Ala Pro
            420                 425                 430

Leu Gln Leu Gly Gly Pro Val Asn Pro Ser Phe Val Asp Ala Gln Thr
            435                 440                 445

Ser Thr Ser Pro Leu Met Ala Gln Gln Leu His Ser Gln His Ala Asp
    450                 455                 460

Val Asp Ala Ala Pro Pro Ser Ser Ser Ser Ser Ala Val Val Val
465                 470                 475                 480

Val Glu Arg His Val His Gly Thr Thr Thr Pro Lys Thr Glu Tyr Ser
                485                 490                 495

Thr Ala Ile Ser Ser Gly Gln Leu Gln Gln Ala Phe Ala Glu Leu Gln
            500                 505                 510

Leu His Ser Ser Asn Asn Asn Ala Thr Gln Gln Gln Gln Gln His Leu
        515                 520                 525

Leu Leu Ser Asn Asn Asn Ser Asn Asn Ser Met Ala Ala Ala Gln
530                 535                 540

Thr Thr Ala Ser Leu Met Lys Asn Cys Asp Leu Leu Ile Ser Asn Asn
545                 550                 555                 560

Leu Tyr Pro Pro Arg Arg Glu Leu Leu Glu Asp Val Ile Val His Gln
                565                 570                 575

Ala Ser Asp Val His Ser Tyr Ser Thr Ser Ala Ser Ala Ala Ala Ile
            580                 585                 590

Ala Ser Ser Ser Asn Arg Ser Gln Gln Gln Gln Gln Gln Gln Gln
        595                 600                 605

His Gln Leu Leu Ser Ala Ala Tyr Glu Leu Gln Gln Gln Gln Gln Leu
    610                 615                 620

Gln Leu Gln Gln Gln Gln Gln Gln Asn Ser Pro Thr Ser Ser Ile
625                 630                 635                 640

Ser Ile Gly Arg Thr Glu Leu Leu Leu Gly Asp Gln Ser Leu Arg Gln
                645                 650                 655

Asp Pro Arg Gly Asn Arg Arg Ser Gly Ser Ser Ile Val Val Leu
            660                 665                 670

Asp Gly Asp Asp Leu Lys Pro Cys Leu Pro Asp Asp Tyr Ile Ser Gly
        675                 680                 685

Gln His His Leu Asn His Gln Gln Leu Gln Gln Gln Gln Leu
    690                 695                 700

Gln Gln Gln His Pro Leu Gln Gln Gln His Tyr Arg Thr His Ser Gly
705                 710                 715                 720

Asp Ile Arg Glu Ile Asp Gln Glu Met Leu Thr Met Leu Ser Val Asn
                725                 730                 735

Gln Asp Asn Gly Pro His Arg Glu Met Ala Val Asp Cys Pro Asp Thr
            740                 745                 750

Phe Ile Ala Arg Asn Lys Thr Pro Pro Arg Tyr Pro Pro Pro Arg Pro
        755                 760                 765

Pro Gln Lys His Lys Lys Ser Thr Asn Thr Thr Thr Thr Thr Ile
770                 775                 780
```

-continued

```
Thr Ala Leu Thr Asn Asn Asp His Ala Asn Lys Met Leu Ile Val Ala
785                 790                 795                 800

Tyr His Ser Ser His Gln His Glu Gln Leu Gln Gln Gln His Pro Ser
            805                 810                 815

Lys Thr Ser Thr Thr Thr Thr Thr Ile Ala Leu Asp Val Ala Thr Gln
        820                 825                 830

Asn Leu Tyr Asn Gln Lys Gln Gln Asn Lys Leu Glu Gln Ile Glu Asn
            835                 840                 845

Tyr Glu Asn Cys Leu Gln Ser Glu Arg Asn Glu Gln His Glu Gln Gln
850                 855                 860

Phe Glu Gln Gln Lys Gln His Gln Ala Thr Thr Ala Met Ala Ala Thr
865                 870                 875                 880

Gln Val Ala Gln Gln Gln Thr Pro Ser His Lys Leu Gln Ala Thr Leu
                885                 890                 895

Ser Ser Asp Pro Asn Gly Asn Ser Asn Ser Asn Asn Asn Ser His Ile
                900                 905                 910

Val Gly Ile Ser Ser Ser Ser Ser Ser Asn Asn Ser Ser Ile Thr Asp
            915                 920                 925

Asp Phe Leu Cys Val Val Asp Gly Leu Tyr Gln Gly Arg Lys Asp Thr
    930                 935                 940

Ala Ser Pro Ser Ser Ser Ala Phe Asp Glu Val Met Ser Lys His Thr
945                 950                 955                 960

Leu Asp Ser Phe Gly Ser Ile Ala Tyr Arg His Leu His Gln Gln His
                965                 970                 975

Gln Ala Thr Ser Asn Gly Asn Ser Ser Ser Asn Thr Ser Asn Thr Asn
                980                 985                 990

Ser Asn Thr Asn Ser Asn Thr Asn Ser Asn Ser Asn Thr Asn Gly Asn
            995                 1000                1005

Thr Ser Asn Asn Thr Ala Val Ser Thr Lys Thr Ala Thr Val Thr
    1010                1015                1020

Lys Thr Gly Val Ser Ser Ser Asn Ser Asn Ser Asn Ser Leu Asn
    1025                1030                1035

Ser Ser Asn Ser Ser Met His Thr Ser Ser Ser Ser Gly His
    1040                1045                1050

Ser Ser Asn Ile Ala Ser Ala Thr Ser Ser Ser Ser Ala Thr Ser
    1055                1060                1065

Ser Ser Thr Val Pro Asp Asp Leu Ser Leu Ala Pro Pro Gly Tyr
    1070                1075                1080

Glu Val Ser Gln Gln Gln Gln Gln Gln His Leu Val Ala Thr Pro
    1085                1090                1095

Val Thr Met Leu Leu Pro Pro Met Ala Lys His Arg Glu Leu Pro
    1100                1105                1110

Val Asp Val Pro Asp Ser Phe Ile Glu Met Val Lys Thr Thr Pro
    1115                1120                1125

Arg Tyr Pro Pro Pro Ala His Leu Ser Ser Arg Gly Ser Leu Leu
    1130                1135                1140

Ser Asn Gly Ser Ala Ser Thr Ala His Thr Thr Leu Ser Ser Met
    1145                1150                1155

Gly Val Ala Pro Ser Pro Val Thr Ala Thr Ala Ala Ala Ala Ala
    1160                1165                1170

Ser Ala Ser Ala Ala Cys Ala Thr Thr Ala Val Ala Ala Ala Ala
    1175                1180                1185
```

```
Val Ser Gly Val Ala Asp Gly Asp Ala Arg Arg Val Ala Asp Glu
1190                1195                1200

Leu Asn Gly Asn Ala Lys Pro Val Pro Pro Arg Asp His Leu
1205                1210                1215

Arg Val Glu Lys Asp Gly Arg Leu Val Asn Cys Ser Pro Ala Pro
1220                1225                1230

Gln Leu Pro Asp Arg Arg Ala Pro Gly Asn Ala Ser Ser Gly Ser
1235                1240                1245

Ser Gly Ala Thr Thr His Pro Leu Gln His Gln Gln Ile Ala Gln
1250                1255                1260

Ile Val Glu Pro Thr Leu Glu Gln Leu Asp Ser Ile Lys Lys Tyr
1265                1270                1275

Gln Glu Gln Leu Arg Arg Arg Glu Glu Glu Arg Ile Ala
1280                1285                1290

Gln Gln Asn Glu Phe Leu Arg Asn Ser Leu Arg Gly Ser Arg Lys
1295                1300                1305

Leu Lys Ala Leu Gln Asp Thr Ala Thr Pro Gly Lys Ala Val Ala
1310                1315                1320

Gln Gln Gln Gln Gln Ala Thr Leu Ala Thr Gln Val Val Gly Val
1325                1330                1335

Glu Asn Glu Ala Tyr Leu Pro Asp Glu Asp Gln Pro Gln Ala Glu
1340                1345                1350

Gln Ile Asp Gly Tyr Gly Glu Leu Ile Ala Ala Leu Thr Arg Leu
1355                1360                1365

Gln Asn Gln Leu Ser Lys Ser Gly Leu Ser Thr Leu Ala Gly Arg
1370                1375                1380

Val Ser Ala Ala His Ser Val Leu Ala Ser Ala Ser Val Ala His
1385                1390                1395

Val Leu Ala Ala Arg Thr Ala Val Leu Gln Arg Arg Arg Ser Arg
1400                1405                1410

Val Ser Gly Pro Leu His His Ser Ser Leu Gly Leu Gln Lys Asp
1415                1420                1425

Ile Val Glu Leu Leu Thr Gln Ser Asn Thr Ala Ala Ala Ile Glu
1430                1435                1440

Leu Gly Asn Leu Leu Thr Ser His Glu Met Glu Gly Leu Leu Leu
1445                1450                1455

Ala His Asp Arg Ile Ala Asn His Thr Asp Gly Thr Pro Ser Pro
1460                1465                1470

Thr Pro Thr Pro Thr Pro Ala Ile Gly Ala Ala Thr Gly Ser Thr
1475                1480                1485

Leu Ser Ser Pro Val Ala Gly Pro Lys Arg Asn Leu Gly Met Val
1490                1495                1500

Val Pro Pro Pro Val Val Pro Pro Leu Ala Gln Arg Gly Ala
1505                1510                1515

Met Pro Leu Pro Arg Gly Glu Ser Pro Pro Val Pro Met Pro
1520                1525                1530

Pro Leu Ala Thr Met Pro Met Ser Met Pro Val Asn Leu Pro Met
1535                1540                1545

Ser Ala Cys Phe Gly Thr Leu Asn Asp Gln Asn Asp Asn Ile Arg
1550                1555                1560

Ile Ile Gln Ile Glu Lys Ser Thr Glu Pro Leu Gly Ala Thr Val
1565                1570                1575

Arg Asn Glu Gly Glu Ala Val Val Ile Gly Arg Ile Val Arg Gly
```

-continued

```
            1580                1585                1590
Gly Ala Ala Glu Lys Ser Gly Leu Leu His Glu Gly Asp Glu Ile
            1595                1600                1605
Leu Glu Val Asn Gly Gln Glu Leu Arg Gly Lys Thr Val Asn Glu
            1610                1615                1620
Val Cys Ala Leu Leu Gly Ala Met Gln Gly Thr Leu Thr Phe Leu
            1625                1630                1635
Ile Val Pro Ala Gly Ser Pro Pro Ser Val Gly Val Met Gly Gly
            1640                1645                1650
Thr Thr Gly Ser Gln Leu Ala Gly Leu Gly Gly Ala His Arg Asp
            1655                1660                1665
Thr Ala Val Leu His Val Arg Ala His Phe Asp Tyr Asp Pro Glu
            1670                1675                1680
Asp Asp Leu Tyr Ile Pro Cys Arg Glu Leu Gly Ile Ser Phe Gln
            1685                1690                1695
Lys Gly Asp Val Leu His Val Ile Ser Arg Glu Asp Pro Asn Trp
            1700                1705                1710
Trp Gln Ala Tyr Arg Glu Gly Glu Glu Asp Gln Thr Leu Ala Gly
            1715                1720                1725
Leu Ile Pro Ser Gln Ser Phe Gln His Gln Arg Glu Thr Met Lys
            1730                1735                1740
Leu Ala Ile Ala Glu Glu Ala Gly Leu Ala Arg Ser Arg Gly Lys
            1745                1750                1755
Asp Gly Ser Gly Ser Lys Gly Ala Thr Leu Leu Cys Ala Arg Lys
            1760                1765                1770
Gly Arg Lys Lys Lys Lys Ala Ser Ser Glu Ala Gly Tyr Pro
            1775                1780                1785
Leu Tyr Ala Thr Thr Ala Pro Asp Glu Thr Asp Pro Glu Glu Ile
            1790                1795                1800
Leu Thr Tyr Glu Glu Val Ala Leu Tyr Tyr Pro Arg Ala Thr His
            1805                1810                1815
Lys Arg Pro Ile Val Leu Ile Gly Pro Pro Asn Ile Gly Arg His
            1820                1825                1830
Glu Leu Arg Gln Arg Leu Met Ala Asp Ser Glu Arg Phe Ser Ala
            1835                1840                1845
Ala Val Pro His Thr Ser Arg Ala Arg Arg Glu Gly Glu Val Pro
            1850                1855                1860
Gly Val Asp Tyr His Phe Ile Thr Arg Gln Ala Phe Glu Ala Asp
            1865                1870                1875
Ile Leu Ala Arg Arg Phe Val Glu His Gly Glu Tyr Glu Lys Ala
            1880                1885                1890
Tyr Tyr Gly Thr Ser Leu Glu Ala Ile Arg Thr Val Val Ala Ser
            1895                1900                1905
Gly Lys Ile Cys Val Leu Asn Leu His Pro Gln Ser Leu Lys Leu
            1910                1915                1920
Leu Arg Ala Ser Asp Leu Lys Pro Tyr Val Val Leu Val Ala Pro
            1925                1930                1935
Pro Ser Leu Asp Lys Leu Arg Gln Lys Lys Leu Arg Asn Gly Glu
            1940                1945                1950
Pro Phe Lys Glu Glu Glu Leu Lys Asp Ile Ile Ala Thr Ala Arg
            1955                1960                1965
Asp Met Glu Ala Arg Trp Gly His Leu Phe Asp Met Ile Ile Ile
            1970                1975                1980
```

```
Asn Asn  Asp Thr Glu Arg Ala  Tyr His Gln Leu Leu  Ala Glu Ile
    1985         1990                  1995

Asn Ser  Leu Glu Arg Glu Pro  Gln Trp Val Pro Ala  Gln Trp Val
    2000         2005                  2010

His Asn  Asn Arg Asp Glu
    2015

<210> SEQ ID NO 8
<211> LENGTH: 871
<212> TYPE: PRT
<213> ORGANISM: Drosophila melanogaster

<400> SEQUENCE: 8

Met His Leu Ser Ala Asp Ile Ser Ser Ala Leu Gln Gln Ile Glu Ala
1               5                   10                  15

Val Lys Lys Gly Ile Asp Glu Ser Asp Asp Pro Lys Leu Gln Met Gln
            20                  25                  30

Thr Ala Glu Ser Leu Ser Thr Ile Leu Gly Ile Leu Gln Asp Pro Val
        35                  40                  45

Phe Arg Thr Ile Val His Val Gln Asp Ser Leu Ser Glu Leu Asn Ala
    50                  55                  60

Gln Leu Ala Gln His Pro Ser Met Leu Pro Asn Asp Phe Asp Ile Asp
65                  70                  75                  80

Val Ala Gly Asn Leu Val Leu Ser Leu Asn Gly Gly Val Met Tyr
                85                  90                  95

Asp Phe Asp Glu Gln Arg Ser Ser His Ser His Ser Ala Pro Gly
                100                 105                 110

Ser Pro Asp Lys Ser Gly Gly Val Gly Glu Glu Pro Arg Pro Gln Ser
            115                 120                 125

Gln Asn Ser Lys Gly Ala Gly Val Ala Asp Leu Tyr Ala Thr Asp Tyr
130                 135                 140

Ala Gln Ile Gln Ala Ile Glu Leu Val Asn Asp Gly Thr Gly Leu Gly
145                 150                 155                 160

Phe Gly Ile Ile Gly Ala Arg Asn Ser Gly Val Ile Val Lys Thr Ile
                165                 170                 175

Leu Pro Gly Gly Val Ala Asp Lys Asp Gly Arg Leu Arg Ser Gly Asp
            180                 185                 190

His Ile Leu Gln Ile Gly Asp Val Asn Leu His Glu Met Val Ser Glu
        195                 200                 205

Gln Val Ala Ala Val Leu Arg Gln Ser Gly Thr His Val Arg Leu Val
    210                 215                 220

Val Ala Arg Pro Val Glu Gln Ser Val Pro Thr Pro Gln Tyr Ala Leu
225                 230                 235                 240

Glu Pro Gly Thr Ala Val Val Pro Thr Arg Val Leu Val Asp Pro Ala
                245                 250                 255

Glu Leu Glu Arg Tyr Leu Ile Ser Thr Gly Tyr Pro Glu Ile Phe Gly
            260                 265                 270

Glu Ser Ser Thr Ala Ser Thr Pro Gln Thr Thr Glu Asp Asp Arg
        275                 280                 285

Phe Val Tyr Arg Gly Glu Thr Ser Met Leu Ile Asp Pro Asn Ile Asp
    290                 295                 300

Leu Glu Glu Leu Leu Ala Leu Pro Glu Thr Glu Lys Leu Gln Val Glu
305                 310                 315                 320

Leu Lys Lys Asp Ala Asn Gly Leu Gly Ile Thr Ile Ala Gly Tyr Val
```

-continued

```
                325                 330                 335
Cys Glu Lys Glu Glu Leu Ser Gly Ile Phe Val Lys Ser Val Ser Pro
                340                 345                 350
Gly Ser Ala Ala Asp Leu Ser Gly Arg Ile Arg Val Asn Asp Arg Ile
                355                 360                 365
Ile Glu Val Asp Gly Gln Ser Leu Gln Gly Tyr Ser Asn His Gln Ala
                370                 375                 380
Val Glu Leu Leu Lys Lys Ser Gly Gln Val Val Asn Leu Arg Leu Glu
385                 390                 395                 400
Arg Tyr Leu Arg Gly Pro Lys Phe Glu Gln Leu Gln Gln Ala Ile Ala
                405                 410                 415
Ala Asn Asp Lys Leu Pro Ser Ser Ala Pro Gly Thr Pro Ser Arg Ala
                420                 425                 430
Pro Met Pro Thr Pro Val Ala Thr Thr Ser Ser Ala Thr Thr Thr Pro
                435                 440                 445
Ser Arg Ser Ile Thr Arg Glu Leu Glu Glu Glu Ala Leu Pro Ala Pro
                450                 455                 460
Glu Ala Phe Met Thr Thr Pro Pro Ser Val Thr Thr Met Thr Thr Thr
465                 470                 475                 480
Thr Leu Ser Ser Phe Gly Ala Gly Lys Gln Leu Val Ala Val Arg Asp
                485                 490                 495
Ser Leu Asp Gly Ser Thr Lys Ile Ile Pro Thr Glu Val Val Pro Leu
                500                 505                 510
Ala Asp Lys Thr Glu Ala Lys Asn Ser Gly Val Ile Thr Arg His Lys
                515                 520                 525
Tyr Tyr Thr Asp Pro Glu Leu Ser Asp Asp Ala Glu Thr Glu Ile Ile
                530                 535                 540
Arg Lys Trp Gln Lys Ile Val Gly Ser Asp Val Glu Val Ile Val Ala
545                 550                 555                 560
Gln Ile Lys Lys Phe Ala Val Gly Gly Leu Gly Ile Ser Leu Glu Gly
                565                 570                 575
Thr Val Asp Val Glu Gly Gly Arg Glu Val Arg Pro His His Tyr Ile
                580                 585                 590
Arg Ser Ile Leu Pro Asp Gly Pro Val Gly Val Asn Gly Val Leu Arg
                595                 600                 605
Ser Gly Asp Glu Leu Leu Glu Val Asn Gly Glu Arg Leu Leu Gly Met
                610                 615                 620
Asn His Leu Glu Val Val Ala Ile Leu Lys Glu Leu Pro Leu Asp Val
625                 630                 635                 640
Arg Met Val Cys Gly Arg Asn Arg Asn Ser Ser Leu Leu Pro Phe Ser
                645                 650                 655
Asp Asp Thr Leu Lys Lys Leu Ser Asn Asn Phe Glu Asn Leu Leu Pro
                660                 665                 670
Ala Thr Asp Arg Leu Val Lys Ala Lys Ser Asp Gly Ser Leu Ala Thr
                675                 680                 685
Ala Gly Ser Val Ala Asp Gly Asp Ser Val Ala Ala Ala Ala Ala Ser
                690                 695                 700
Phe Ser Lys Leu Lys Ser Arg Ser Leu Glu Pro Leu Thr Gly Leu Ala
705                 710                 715                 720
Met Trp Ser Ser Gln Pro Gln Ile Ile Glu Leu Val Lys Gly Asp Arg
                725                 730                 735
Gly Leu Gly Phe Ser Ile Leu Asp Tyr Gln Asp Pro Leu Asp Pro Asn
                740                 745                 750
```

```
Asp Thr Leu Ile Val Ile Arg Ser Leu Val Pro Gly Gly Val Ala Gln
            755                 760                 765

Leu Asp Gly Arg Leu Ile Pro Gly Asp Arg Leu Leu Phe Val Asn Ser
770                 775                 780

Ile Asn Leu Glu Asn Ala Ser Leu Asp Gln Ala Val Gln Ala Leu Lys
785                 790                 795                 800

Gly Ala Ser Lys Gly Val Val Arg Ile Gly Val Ala Lys Pro Leu Pro
                805                 810                 815

Met Thr Asp Asn Ser Leu Lys Ala Cys Ser Asn Ala Ser Thr Thr Ser
            820                 825                 830

Glu Glu Thr Leu Asp Ala Gln Pro Ser Pro Ala Leu Pro Thr Val
                835                 840                 845

Ala Pro Pro Ala Met Pro Pro Ser Ala Ser Met Gly Ala Glu Pro Asp
850                 855                 860

Leu Ile Pro Asp Trp Arg Asn
865                 870

<210> SEQ ID NO 9
<211> LENGTH: 246
<212> TYPE: PRT
<213> ORGANISM: Drosophila melanogaster

<400> SEQUENCE: 9

Met Ala Asp Asn Ala Glu Pro Leu Thr Leu Ser Arg Asp Val Lys Arg
1               5                   10                  15

Ser Ile Glu Leu Leu Gly Lys Leu Gln Ala Ser Gly Asp Phe Pro Thr
                20                  25                  30

Thr Lys Leu Ala Ala Leu Gln Lys Val Leu Asn Ser Asp Phe Met Thr
            35                  40                  45

Ser Val Arg Glu Val Tyr Glu His Val Tyr Glu Thr Val Asp Ile Gln
        50                  55                  60

Gly Ser His Asp Val Arg Ala Ser Ala Thr Ala Lys Ala Thr Val Ala
65                  70                  75                  80

Ala Phe Ala Ala Ser Glu Gly His Ala His Pro Arg Val Val Glu Leu
                85                  90                  95

Pro Lys Thr Glu Glu Gly Lys Thr Arg Pro Tyr Glu Leu Arg Ile Glu
            100                 105                 110

Gly Ile Pro Leu Tyr His Lys Thr Asn Thr Leu Ile Val Lys Val Tyr
        115                 120                 125

Arg Pro Arg Ile Tyr Val Ser Ile Ile His Leu Ile Trp Lys Ala Leu
130                 135                 140

Ser Ile Phe Asn Phe Cys Phe Ser Gly Leu Gly Phe Asn Val Met Gly
145                 150                 155                 160

Gly Lys Glu Gln Asn Ser Pro Ile Tyr Ile Ser Arg Ile Ile Pro Gly
                165                 170                 175

Gly Val Ala Asp Arg His Gly Gly Leu Lys Arg Gly Asp Gln Leu Leu
            180                 185                 190

Ser Val Asn Gly Val Ser Val Glu Gly Glu Asn His Glu Lys Ala Val
        195                 200                 205

Glu Leu Leu Lys Gln Ala Val Gly Ser Val Lys Leu Val Val Arg Tyr
    210                 215                 220

Thr Pro Lys Val Leu Glu Glu Met Glu Met Arg Phe Asp Lys Gln Arg
225                 230                 235                 240

Asn Thr Arg Arg Arg Gln
```

<210> SEQ ID NO 10
<211> LENGTH: 5954
<212> TYPE: DNA
<213> ORGANISM: Artificial
<220> FEATURE:
<223> OTHER INFORMATION: Par6_AcGFP DNA sequence including all "natural" control elements

<400> SEQUENCE: 10

```
gcggccgcgc tgtgcgtgtg tgtgtctgtg ttgatgcggg cctgcgctgg tgtgcgtgcg      60
aatcgctgtc tcaaggtttc agtttcgtca gcttattcct gcagctgagc tcttcggctc     120
tcggatagtc gcaatttcac cgccttttcc cagctgcctt ggaaaagtgg tcccaaaata     180
tatgaatatg tgcgttgtgg gctggcttta actattcctt gcgtgtaga ctccttatgc      240
ttcctttggc cccgctagtc tccttgtctg ttgtttgggt ttatgttttc acacgcactc     300
gtttaaagac tatatatata tatgtatttg gtatagcacc tcctctcgaa aatcttgatt    360
tttagttttt ctagcgactt aaaattttgt ttcgttggtt gcttttgttt tgaaatcgat    420
tcgctcaact ttgtcgtagc tgctgtgtga cctatctcga ctctggcgtt cacatctaaa    480
caaattcagt tgtctaattg gacacttcac gctcgacaac aacacacaaa aacagtttca    540
ttttacagta accctcgtcg ctggcgctgc gctacaattg gggcatattc gtgctggcgt    600
cttgcctgcc ttcgatttaa aagcgggttt ttatttattt atttaaaaaa cgtctttgat    660
taaaactgag catttaaata tagctaattc ttgtcttgta acagttaagc ctcttttttc    720
gtgcaaacag cagccacttt gcaaatgtag cgcatctgaa gatccaccca gcccacacaa    780
acaaactgtc tctacactaa cgcagcaaca tggctgctca gactctatcg atatatcgat    840
atatgcacaa catcggttca tgcctaagtt actctgggaa atatttaaaa acaaacaaag    900
aacataccgt tattaaaaaa aaaaactat tgttgtgata aattcaaaac ctttgctagc      960
tatattgaaa acaaattatt attatttcta agtctttta gatactttca ttgttgttta    1020
aatctattgc ttatagcata tttgtggtat tttagaaaac tgaaatggta tattttggtt    1080
ttgcattccc cacggtcact ctggatctat taccatccga taaccgatag tgcctaccaa    1140
tatcgaagta cgatagtgcc cgataggttc atccatccat tttttttatt taattagttt    1200
taatttagat ttctaactct aatttattgg cggccccca ctatcgtcgc tccccgccat     1260
cggtacgctg cactttggtt cggtttcggt tcgcatcggg cgtatcggtt cgatttcgat    1320
cctgaagatc agatcagaat ctgcggaact caactgccgt gttttgtgtt gtgtgtgagg    1380
aacggagagg aaaactgtca gtgcactctt gatcgggcgg atcggagaaa atgtcgaaga    1440
acaagataaa cacaacgtcc gcaacggcgg ccagtgacac gaatctaatc gaggtgaaat    1500
cgaaggtgag tcctaacttt cgtggccccc ggattccacg ccccttctg cggcgctgag     1560
ctgctgattc atgcgctcag gaatgggatt aatagcttaa attggagttc tgtgcgtgga    1620
aagggggtct ttagtctgag gagcaatgtg tctaccaatt tgggaactcc tatctgttga    1680
gctcgattgt gtcaaagcgg ccagagcagg gattaatgct tggagtgcga ggtgtgagga    1740
gcaactggtt tccatcttag aagcacccca aaagtgacaa tttgcccttg cgaatgcatc    1800
ttacttgtcg gaattcctga gctctgatat ggattgttgc aacacccttt attgcttggg    1860
ctctttgcct gaaaaccaat ctgttgcgcc ttactcaaaa actaccctgt ttcgttcatt    1920
ttctgtaatt ttacagagaa ggaaacttca gttattaatt agtcaaggta caattcttca    1980
```

```
agataaactc cagtaatagc tataaggcag tagatgtact gcaattcagt gaaggtccca    2040
ttaaattagt aaaatgtctg catacaattg aatcaacagg tgatgctgat gaacaaacta    2100
tacgggtttc aaaagattca gcccctttac taatcaatac gtatcccttta gttcgatgca   2160 gagtttcgga ggtggagctt caagcgaaat gaggcggagc agagcttcga caaattcgca    2220
tccctcattg agcagctgca caagctgacc aacatccagt ttctcatact ctacatcgat    2280
ccgcgggaca atgatctgtt gccgattaac aacgacgata acttcggccg ggccctgaaa    2340
acagcacgtc cacttttacg ggtcattgtg cagcgaaagg gtgagtatgg gtatgcataa    2400
gatacaatac gagccactca accacaatct tttcgttcac tctatagatg atcttaatga    2460
gtactctggc tttggaacga tgaaaccgag aaacctcatc ggcagcatac tgatgggcca    2520
tacgccagtg aagacaaagg cgccatcgat atccataccg cacgatttcc gtcaagtctc    2580
ggccattata gatgtggata tagtgccgga aacgcataga agagtgcggc tactgaagca    2640
cggcagcgat aagcccctgg gattctacat acgggatggc acctctgtca gggtgacggc    2700
cagtgggcta gagaagcagc cgggcatttt tatatcccgt ttggttccgg gcggtctggc    2760
cgaaagtact ggcctgctgg ccgtcaacga tgaggtgatc gaggtaaatg catcgaagt    2820 ggctggcaag actctggatc aagtcaccga catgatggtg ccaacagct ccaatctgat     2880 aatcaccgtg aagccggcca atcagcgcac actgacgtcc acacatcgcg gatcctttc    2940 aaggaacagc cagctgtcca gtgggtcaca tcacactaat aatacaaaca cctccgacga    3000
gatcgagcac gacgatcagg acgatattgt ggacttaacg ggcgtcaccc tcgacgagag    3060
tccaacgtcc acgtcagccg gcaatcacaa ccatcagccg ccattatcct catcaccctc    3120
gtcgcaccac cagcaggcag cctccaatgc gtccacgata atggccagcg atgtcaagga    3180
tggagtgctg catttgatgg tgagcaaggg cgccgagctg ttcaccggca tcgtgcccat    3240
cctgatcgag ctgaatggcg atgtgaatgg ccacaagttc agcgtgagcg gcgagggcga    3300
gggcgatgcc acctacggca agctgaccct gaagttcatc tgcaccaccg gcaagctgcc    3360
tgtgccctgg cccaccctgg tgaccaccct gagctacggc gtgcagtgct tctcacgcta    3420
ccccgatcac atgaagcagc acgacttctt caagagcgcc atgcctgagg gctacatcca    3480
ggagcgcacc atcttcttcg aggatgacgg caactacaag tcgcgcgccg aggtgaagtt    3540
cgagggcgat accctggtga atcgcatcga gctgaccggc accgatttca aggaggatgg    3600
caacatcctg ggcaataaga tggagtacaa ctacaacgcc cacaatgtgt acatcatgac    3660
cgacaaggcc aagaatggca tcaaggtgaa cttcaagatc cgccacaaca tcgaggatgg    3720
cagcgtgcag ctggccgacc actaccagca gaatacccc atcggcgatg ccctgtgct     3780 gctgcccgat aaccactacc tgtccaccca gagcgccctg tccaaggacc caacgagaa    3840 gcgcgatcac atgatctact cggcttcgt gaccgccgcc gccatcaccc acggcatgga    3900
tgagctgtac aagtagtagg attaacccgg cgatacagca cctccagcag acgcagccag    3960
aacttaagca acgaaaaacg cgaattcatc gctgagaagt gcagaggatt ttcagtttat    4020
cagacttaac tttccttaag atcgaataag ttcgttaaac tcgagtcaat tatttaaagt    4080
tatacaagtt aggccaactt attcacatgt acactgatcg cttgtatatc gctcacttac    4140
taaagcgact gtcatagctc aaccagccat gatttgaaaa gtcaccttat aaaatctatt    4200
ggtattagcc tgaaagcctg attgattgag taaacaacat atcggccata tcccattcat    4260
ttcttgttaa tcctgccat tcaaatttaa cgttctgcaa aatttccagt ccgattgtag    4320
gtgagcaata tataaaacac gattgtatat acatgtgtaa tcatcatacg actttcctcc    4380
```

```
atacattcca cgaaacactc aaagtcaaag aaaacacacc tattcatttg cacgttttg      4440
aatgcagtct cttgttttta tcttttttcc tggcatatat atatatgtgt atttaaattt      4500
gtaagattta cgtcttgtta ttattcttgc ttgttgtatt agactagagt gagacagcta      4560
gaggagagag tgaaatagag agagggcatc aaatgctgaa ggcagatcaa tttatttaac      4620
ttaaccattt gaaacggcaa taattgtaac aaaatcacat atacgagcac gaataattta      4680
taaaaaaaaa aaacattcca ttttatgtac tgtgacaagt cggaaaagcc taacaaaatt      4740
atatttcctg atttgtaagc cttgttttta atttgagccg atcattttgc gtatatctgc      4800
tatgttttgt ttagctcaat ttcttatttt ttcggcatta ctcattatat ctgtttattt      4860
taaaaaccat ttgtaatttt taacttttgt tttttcgtca ttgtgtccaa tactcgtcca      4920
agttctttgt tgtcattgtc atcacttaga gttatggaga aaggatagaa aaacgaggag      4980
ataaagttaa caaaacgtta agatacaaac gaaacaccaa cagcgccttc gccttcaaga      5040
gagcaattcg atactttta tatatataca agagaatata taaacgaata caatctatgt      5100
tatgtacgta cccctgtaca cacaattgaa ttgaagtctg tgtattcgct ttagtaaaat      5160
tgagaaaacg ccactcacgg cagatgggat gcaatgcgat ctgctcgact tgaagttaac      5220
aatattaata tttatgggtc gcaacgggca taactaaccc catacgaacg tgtaccctgg      5280
gtagatagca agatctagga tagacagcag cgaatctgaa actataacta aatgcgtatc      5340
gccgcccaac cactcccctc atatacccat ttcacatata cccttgcatt atcgagaaat      5400
ctgaacttac atcgaacaaa agtcgccaga atatcccgat ttccaagcaa acgcatgtat      5460
atatatatat atacaaaagc taatgtgtat tcccgctaag caactgaaaa gaccgaaaag      5520
caaatcacga aagaaaacct tatattttga tgtatgtatt attatttttt aataaaccta      5580
agagaacttg taaccgatct ggtgtgtaat tggtttttc ctgggaggct atagcaaaac       5640
aatgtaagtt tattgtttat atcacaacca attcgaggcg ttaaagtata caaaaaagtt      5700
aaaaatgata ttcggttcct gcatttataa acgaaaaaat tgtttccctc tgtaagcaat      5760
acttttcaat tcaactgaat tgctttcact tattttagc ttacaaaaat caatttaaat       5820
acattagccg ggccttaatc aaaaaagatc ttacatatac ccttttgaag actgcgaatt      5880
aaaaaaccag ttaacgatat agttttgtt ccatttgggg attcgattta ttcgaccact       5940
cttttggcgg ccgc                                                        5954
```

<210> SEQ ID NO 11
<211> LENGTH: 590
<212> TYPE: PRT
<213> ORGANISM: Artificial
<220> FEATURE:
<223> OTHER INFORMATION: Par6AcGFP Protein Sequence

<400> SEQUENCE: 11

Met Ser Lys Asn Lys Ile Asn Thr Thr Ser Ala Thr Ala Ala Ser Asp
1               5                   10                  15

Thr Asn Leu Ile Glu Val Lys Ser Lys Phe Asp Ala Glu Phe Arg Arg
            20                  25                  30

Trp Ser Phe Lys Arg Asn Glu Ala Glu Gln Ser Phe Asp Lys Phe Ala
        35                  40                  45

Ser Leu Ile Glu Gln Leu His Lys Leu Thr Asn Ile Gln Phe Leu Ile
    50                  55                  60

Leu Tyr Ile Asp Pro Arg Asp Asn Asp Leu Leu Pro Ile Asn Asn Asp
65                  70                  75                  80

```
Asp Asn Phe Gly Arg Ala Leu Lys Thr Ala Arg Pro Leu Leu Arg Val
                85                  90                  95
Ile Val Gln Arg Lys Asp Asp Leu Asn Glu Tyr Ser Gly Phe Gly Thr
            100                 105                 110
Met Lys Pro Arg Asn Leu Ile Gly Ser Ile Leu Met Gly His Thr Pro
        115                 120                 125
Val Lys Thr Lys Ala Pro Ser Ile Ser Ile Pro His Asp Phe Arg Gln
    130                 135                 140
Val Ser Ala Ile Ile Asp Val Asp Ile Val Pro Glu Thr His Arg Arg
145                 150                 155                 160
Val Arg Leu Leu Lys His Gly Ser Asp Lys Pro Leu Gly Phe Tyr Ile
                165                 170                 175
Arg Asp Gly Thr Ser Val Arg Val Thr Ala Ser Gly Leu Glu Lys Gln
            180                 185                 190
Pro Gly Ile Phe Ile Ser Arg Leu Val Pro Gly Gly Leu Ala Glu Ser
        195                 200                 205
Thr Gly Leu Leu Ala Val Asn Asp Glu Val Ile Glu Val Asn Gly Ile
    210                 215                 220
Glu Val Ala Gly Lys Thr Leu Asp Gln Val Thr Asp Met Met Val Ala
225                 230                 235                 240
Asn Ser Ser Asn Leu Ile Ile Thr Val Lys Pro Ala Asn Gln Arg Thr
                245                 250                 255
Leu Thr Ser Thr His Arg Gly Ser Phe Ser Arg Asn Ser Gln Leu Ser
            260                 265                 270
Ser Gly Ser His His Thr Asn Asn Thr Asn Thr Ser Asp Glu Ile Glu
        275                 280                 285
His Asp Asp Gln Asp Ile Val Asp Leu Thr Gly Val Thr Leu Asp
        290                 295                 300
Glu Ser Pro Thr Ser Thr Ser Ala Gly Asn His Asn His Gln Pro Pro
305                 310                 315                 320
Leu Ser Ser Ser Pro Ser Ser His His Gln Gln Ala Ala Ser Asn Ala
                325                 330                 335
Ser Thr Ile Met Ala Ser Asp Val Lys Asp Gly Val Leu His Leu Met
            340                 345                 350
Val Ser Lys Gly Ala Glu Leu Phe Thr Gly Ile Val Pro Ile Leu Ile
        355                 360                 365
Glu Leu Asn Gly Asp Val Asn Gly His Lys Phe Ser Val Ser Gly Glu
    370                 375                 380
Gly Glu Gly Asp Ala Thr Tyr Gly Lys Leu Thr Leu Lys Phe Ile Cys
385                 390                 395                 400
Thr Thr Gly Lys Leu Pro Val Pro Trp Pro Thr Leu Val Thr Thr Leu
                405                 410                 415
Ser Tyr Gly Val Gln Cys Phe Ser Arg Tyr Pro Asp His Met Lys Gln
            420                 425                 430
His Asp Phe Phe Lys Ser Ala Met Pro Glu Gly Tyr Ile Gln Glu Arg
        435                 440                 445
Thr Ile Phe Phe Glu Asp Asp Gly Asn Tyr Lys Ser Arg Ala Glu Val
    450                 455                 460
Lys Phe Glu Gly Asp Thr Leu Val Asn Arg Ile Glu Leu Thr Gly Thr
465                 470                 475                 480
Asp Phe Lys Glu Asp Gly Asn Ile Leu Gly Asn Lys Met Glu Tyr Asn
                485                 490                 495
```

```
Tyr Asn Ala His Asn Val Tyr Ile Met Thr Asp Lys Ala Lys Asn Gly
                500                 505                 510

Ile Lys Val Asn Phe Lys Ile Arg His Asn Ile Glu Asp Gly Ser Val
            515                 520                 525

Gln Leu Ala Asp His Tyr Gln Gln Asn Thr Pro Ile Gly Asp Gly Pro
        530                 535                 540

Val Leu Leu Pro Asp Asn His Tyr Leu Ser Thr Gln Ser Ala Leu Ser
545                 550                 555                 560

Lys Asp Pro Asn Glu Lys Arg Asp His Met Ile Tyr Phe Gly Phe Val
                565                 570                 575

Thr Ala Ala Ile Thr His Gly Met Asp Glu Leu Tyr Lys
            580                 585                 590

<210> SEQ ID NO 12
<211> LENGTH: 843
<212> TYPE: PRT
<213> ORGANISM: Drosophila melanogaster

<400> SEQUENCE: 12

Met Ser Tyr Met Pro Ala Gln Asn Arg Thr Met Ser His Asn Asn Gln
1               5                   10                  15

Tyr Asn Pro Pro Asp Leu Pro Pro Met Val Ser Ala Lys Glu Gln Thr
            20                  25                  30

Leu Met Trp Gln Gln Asn Ser Tyr Leu Gly Asp Ser Gly Ile His Ser
        35                  40                  45

Gly Ala Val Thr Gln Val Pro Ser Leu Ser Gly Lys Glu Asp Glu Glu
    50                  55                  60

Met Glu Gly Asp Pro Leu Met Phe Asp Leu Asp Thr Gly Phe Pro Gln
65                  70                  75                  80

Asn Phe Thr Gln Asp Gln Val Asp Met Asn Gln Gln Leu Ser Gln
                85                  90                  95

Thr Arg Ser Gln Arg Val Arg Ala Ala Met Phe Pro Glu Thr Leu Glu
            100                 105                 110

Glu Gly Ile Glu Ile Pro Ser Thr Gln Phe Asp Pro Gln Gln Pro Thr
        115                 120                 125

Ala Val Gln Arg Leu Ser Glu Pro Ser Gln Met Leu Lys His Ala Val
    130                 135                 140

Val Asn Leu Ile Asn Tyr Gln Asp Asp Ala Glu Leu Ala Thr Arg Ala
145                 150                 155                 160

Ile Pro Glu Leu Ile Lys Leu Leu Asn Asp Glu Asp Gln Val Val Val
                165                 170                 175

Ser Gln Ala Ala Met Met Val His Gln Leu Ser Lys Lys Glu Ala Ser
            180                 185                 190

Arg His Ala Ile Met Asn Ser Pro Gln Met Val Ala Ala Leu Val Arg
        195                 200                 205

Ala Ile Ser Asn Ser Asn Asp Leu Glu Ser Thr Lys Ala Ala Val Gly
    210                 215                 220

Thr Leu His Asn Leu Ser His His Arg Gln Gly Leu Leu Ala Ile Phe
225                 230                 235                 240

Lys Ser Gly Gly Ile Pro Ala Leu Val Lys Leu Leu Ser Ser Pro Val
                245                 250                 255

Glu Ser Val Leu Phe Tyr Ala Ile Thr Thr Leu His Asn Leu Leu Leu
            260                 265                 270

His Gln Asp Gly Ser Lys Met Ala Val Arg Leu Ala Gly Gly Leu Gln
        275                 280                 285
```

-continued

```
Lys Met Val Thr Leu Leu Gln Arg Asn Asn Val Lys Phe Leu Ala Ile
    290                 295                 300

Val Thr Asp Cys Leu Gln Ile Leu Ala Tyr Gly Asn Gln Glu Ser Lys
305                 310                 315                 320

Leu Ile Ile Leu Ala Ser Gly Gly Pro Asn Glu Leu Val Arg Ile Met
                    325                 330                 335

Arg Ser Tyr Asp Tyr Glu Lys Leu Leu Trp Thr Thr Ser Arg Val Leu
                340                 345                 350

Lys Val Leu Ser Val Cys Ser Ser Asn Lys Pro Ala Ile Val Asp Ala
            355                 360                 365

Gly Gly Met Gln Ala Leu Ala Met His Leu Gly Asn Met Ser Pro Arg
        370                 375                 380

Leu Val Gln Asn Cys Leu Trp Thr Leu Arg Asn Leu Ser Asp Ala Ala
385                 390                 395                 400

Thr Lys Val Glu Gly Leu Glu Ala Leu Leu Gln Ser Leu Val Gln Val
                405                 410                 415

Leu Gly Ser Thr Asp Val Asn Val Val Thr Cys Ala Ala Gly Ile Leu
            420                 425                 430

Ser Asn Leu Thr Cys Asn Asn Gln Arg Asn Lys Ala Thr Val Cys Gln
        435                 440                 445

Val Gly Gly Val Asp Ala Leu Val Arg Thr Ile Ile Asn Ala Gly Asp
    450                 455                 460

Arg Glu Glu Ile Thr Glu Pro Ala Val Cys Ala Leu Arg His Leu Thr
465                 470                 475                 480

Ser Arg His Val Asp Ser Glu Leu Ala Gln Asn Ala Val Arg Leu Asn
                485                 490                 495

Tyr Gly Leu Ser Val Ile Val Lys Leu Leu His Pro Ser Arg Trp
            500                 505                 510

Pro Leu Ile Lys Ala Val Ile Gly Leu Ile Arg Asn Leu Ala Leu Cys
        515                 520                 525

Pro Ala Asn His Ala Pro Leu Arg Glu His Gly Ala Ile His His Leu
    530                 535                 540

Val Arg Leu Leu Met Arg Ala Phe Gln Asp Thr Glu Arg Gln Arg Ser
545                 550                 555                 560

Ser Ile Ala Thr Thr Gly Ser Gln Gln Pro Ser Ala Tyr Ala Asp Gly
                565                 570                 575

Val Arg Met Glu Glu Ile Val Glu Gly Thr Val Gly Ala Leu His Ile
            580                 585                 590

Leu Ala Arg Glu Ser His Asn Arg Ala Leu Ile Arg Gln Gln Ser Val
        595                 600                 605

Ile Pro Ile Phe Val Arg Leu Leu Phe Asn Glu Ile Glu Asn Ile Gln
    610                 615                 620

Arg Val Ala Ala Gly Val Leu Cys Glu Leu Ala Ala Asp Lys Glu Gly
625                 630                 635                 640

Ala Glu Ile Ile Glu Gln Glu Gly Ala Thr Gly Pro Leu Thr Asp Leu
                645                 650                 655

Leu His Ser Arg Asn Glu Gly Val Ala Thr Tyr Ala Ala Ala Val Leu
            660                 665                 670

Phe Arg Met Ser Glu Asp Lys Pro Gln Asp Tyr Lys Lys Arg Leu Ser
        675                 680                 685

Ile Glu Leu Thr Asn Ser Leu Leu Arg Glu Asp Asn Asn Ile Trp Ala
    690                 695                 700
```

```
Asn Ala Asp Leu Gly Met Gly Pro Asp Leu Gln Asp Met Leu Gly Pro
705                 710                 715                 720

Glu Glu Ala Tyr Glu Gly Leu Tyr Gly Gln Gly Pro Pro Ser Val His
            725                 730                 735

Ser Ser His Gly Gly Arg Ala Phe His Gln Gln Gly Tyr Asp Thr Leu
                740                 745                 750

Pro Ile Asp Ser Met Gln Gly Leu Glu Ile Ser Ser Pro Val Gly Gly
            755                 760                 765

Gly Gly Ala Gly Gly Ala Pro Gly Asn Gly Gly Ala Val Gly Gly Ala
        770                 775                 780

Ser Gly Gly Gly Asn Ile Gly Ala Ile Pro Pro Ser Gly Ala Pro
785                 790                 795                 800

Thr Ser Pro Tyr Ser Met Asp Met Asp Val Gly Glu Ile Asp Ala Gly
                805                 810                 815

Ala Leu Asn Phe Asp Leu Asp Ala Met Pro Thr Pro Pro Asn Asp Asn
                820                 825                 830

Asn Asn Leu Ala Ala Trp Tyr Asp Thr Asp Cys
            835                 840

<210> SEQ ID NO 13
<211> LENGTH: 781
<212> TYPE: PRT
<213> ORGANISM: Drosophila melanogaster

<400> SEQUENCE: 13

Met Ala Thr Gln Ala Asp Leu Met Glu Leu Asp Met Ala Met Glu Pro
1               5                   10                  15

Asp Arg Lys Ala Ala Val Ser His Trp Gln Gln Gln Ser Tyr Leu Asp
            20                  25                  30

Ser Gly Ile His Ser Gly Ala Thr Thr Thr Ala Pro Ser Leu Ser Gly
        35                  40                  45

Lys Gly Asn Pro Glu Glu Glu Asp Val Asp Thr Ser Gln Val Leu Tyr
    50                  55                  60

Glu Trp Glu Gln Gly Phe Ser Gln Ser Phe Thr Gln Glu Gln Val Ala
65                  70                  75                  80

Asp Ile Asp Gly Gln Tyr Ala Met Thr Arg Ala Gln Arg Val Arg Ala
                85                  90                  95

Ala Met Phe Pro Glu Thr Leu Asp Glu Gly Met Gln Ile Pro Ser Thr
            100                 105                 110

Gln Phe Asp Ala Ala His Pro Thr Asn Val Gln Arg Leu Ala Glu Pro
        115                 120                 125

Ser Gln Met Leu Lys His Ala Val Val Asn Leu Ile Asn Tyr Gln Asp
    130                 135                 140

Asp Ala Glu Leu Ala Thr Arg Ala Ile Pro Glu Leu Thr Lys Leu Leu
145                 150                 155                 160

Asn Asp Glu Asp Gln Val Val Val Asn Lys Ala Ala Val Met Val His
                165                 170                 175

Gln Leu Ser Lys Lys Glu Ala Ser Arg His Ala Ile Met Arg Ser Pro
            180                 185                 190

Gln Met Val Ser Ala Ile Val Arg Thr Met Gln Asn Thr Asn Asp Val
        195                 200                 205

Glu Thr Ala Arg Cys Thr Ala Gly Thr Leu His Asn Leu Ser His His
    210                 215                 220

Arg Glu Gly Leu Leu Ala Ile Phe Lys Ser Gly Gly Ile Pro Ala Leu
225                 230                 235                 240
```

```
Val Lys Met Leu Gly Ser Pro Val Asp Ser Val Leu Phe Tyr Ala Ile
            245                 250                 255

Thr Thr Leu His Asn Leu Leu Leu His Gln Glu Gly Ala Lys Met Ala
            260                 265                 270

Val Arg Leu Ala Gly Gly Leu Gln Lys Met Val Ala Leu Leu Asn Lys
            275                 280                 285

Thr Asn Val Lys Phe Leu Ala Ile Thr Thr Asp Cys Leu Gln Ile Leu
290                 295                 300

Ala Tyr Gly Asn Gln Glu Ser Lys Leu Ile Ile Leu Ala Ser Gly Gly
305                 310                 315                 320

Pro Gln Ala Leu Val Asn Ile Met Arg Thr Tyr Thr Tyr Glu Lys Leu
            325                 330                 335

Leu Trp Thr Thr Ser Arg Val Leu Lys Val Leu Ser Val Cys Ser Ser
            340                 345                 350

Asn Lys Pro Ala Ile Val Glu Ala Gly Gly Met Gln Ala Leu Gly Leu
            355                 360                 365

His Leu Thr Asp Pro Ser Gln Arg Leu Val Gln Asn Cys Leu Trp Thr
            370                 375                 380

Leu Arg Asn Leu Ser Asp Ala Ala Thr Lys Gln Glu Gly Met Glu Gly
385                 390                 395                 400

Leu Leu Gly Thr Leu Val Gln Leu Leu Gly Ser Asp Asp Ile Asn Val
            405                 410                 415

Val Thr Cys Ala Ala Gly Ile Leu Ser Asn Leu Thr Cys Asn Asn Tyr
            420                 425                 430

Lys Asn Lys Met Met Val Cys Gln Val Gly Gly Ile Glu Ala Leu Val
            435                 440                 445

Arg Thr Val Leu Arg Ala Gly Asp Arg Glu Asp Ile Thr Glu Pro Ala
            450                 455                 460

Ile Cys Ala Leu Arg His Leu Thr Ser Arg His Gln Glu Ala Glu Met
465                 470                 475                 480

Ala Gln Asn Ala Val Arg Leu His Tyr Gly Leu Pro Val Val Val Lys
            485                 490                 495

Leu Leu His Pro Pro Ser His Trp Pro Leu Ile Lys Ala Thr Val Gly
            500                 505                 510

Leu Ile Arg Asn Leu Ala Leu Cys Pro Ala Asn His Ala Pro Leu Arg
            515                 520                 525

Glu Gln Gly Ala Ile Pro Arg Leu Val Gln Leu Leu Val Arg Ala His
            530                 535                 540

Gln Asp Thr Gln Arg Arg Thr Ser Met Gly Gly Thr Gln Gln Gln Phe
545                 550                 555                 560

Val Glu Gly Val Arg Met Glu Glu Ile Val Glu Gly Cys Thr Gly Ala
            565                 570                 575

Leu His Ile Leu Ala Arg Asp Val His Asn Arg Ile Val Ile Arg Gly
            580                 585                 590

Leu Asn Thr Ile Pro Leu Phe Val Gln Leu Leu Tyr Ser Pro Ile Glu
            595                 600                 605

Asn Ile Gln Arg Val Ala Ala Gly Val Leu Cys Glu Leu Ala Gln Asp
610                 615                 620

Lys Glu Ala Ala Glu Ala Ile Glu Ala Glu Gly Ala Thr Ala Pro Leu
625                 630                 635                 640

Thr Glu Leu Leu His Ser Arg Asn Glu Gly Val Ala Thr Tyr Ala Ala
            645                 650                 655
```

-continued

```
Ala Val Leu Phe Arg Met Ser Glu Asp Lys Pro Gln Asp Tyr Lys Lys
            660                 665                 670

Arg Leu Ser Val Glu Leu Thr Ser Ser Leu Phe Arg Thr Glu Pro Met
        675                 680                 685

Ala Trp Asn Glu Thr Ala Asp Leu Gly Leu Asp Ile Gly Ala Gln Gly
        690                 695                 700

Glu Pro Leu Gly Tyr Arg Gln Asp Asp Pro Ser Tyr Arg Ser Phe His
705                 710                 715                 720

Ser Gly Gly Tyr Gly Gln Asp Ala Leu Gly Met Asp Pro Met Met Glu
                725                 730                 735

His Glu Met Gly Gly His His Pro Gly Ala Asp Tyr Pro Val Asp Gly
            740                 745                 750

Leu Pro Asp Leu Gly His Ala Gln Asp Leu Met Asp Gly Leu Pro Pro
        755                 760                 765

Gly Asp Ser Asn Gln Leu Ala Trp Phe Asp Thr Asp Leu
770                 775                 780
```

METHOD FOR IDENTIFYING CANCER DRUG CANDIDATES IN DROSOPHILA

This application claims the benefit of U.S. Provisional Application No. 61/561,560, filed Nov. 18, 2011, the contents of which are hereby incorporated by reference in their entirety.

This application incorporates-by-reference nucleotide and/or amino acid sequences which are present in the file named "121116_7526_83099_A_Sequence_Listing_REB.txt," which is 107 kilobytes in size, and which was created Nov. 16, 2012 in the IBM-PC machine format, having an operating system compatibility with MS-Windows, which is contained in the text file filed Nov. 16, 2012 as part of this application.

Throughout this application, various publications are referenced, including referenced in parenthesis. Full citations for publications referenced in parenthesis may be found listed in alphabetical order at the end of the specification immediately preceding the claims. The disclosures of all referenced publications in their entireties are hereby incorporated by reference into this application in order to more fully describe the state of the art to which this invention pertains.

BACKGROUND OF INVENTION

High Throughput Drug Screens

The drug discovery process has traditionally been initiated by searching a very large chemical library for compounds that can affect disease characteristics, to identify "hit" compounds. Hits are further tested and developed into leads. Lead compounds in turn are further refined, generally using medicinal chemistry, and tested with view to enter clinical trials and finally developing a drug for use in man.

High throughput screening methods for hits are generally based on in vitro cell culture, biochemical assays or receptor binding assays. Hit compounds identified in these assays need much in the way of further testing and refinement for in vivo use. Even in vitro cell culture assays, which are less artificial than biochemical or receptor binding assays, often fail to reliably indicate, for example, whether a compound will be toxic in vivo. The behavior of individual cells in culture can differ dramatically from the behavior of tissues in response to the same agent. Cells in culture often lack the nutrients, cell-cell contacts, basal membrane contacts, cell-cell signaling events, and physical forces that influence their behavior in vivo. Furthermore, immortalized cell lines often exhibit metabolisms and signal transduction events that vary markedly from the primary cell lines from which they are derived. As a result, the vast majority of hit compounds identified using traditional in vitro high throughput screening methods never become drugs, even after extensive medicinal chemistry optimization efforts are applied (Keserü and Makara, 2006).

In Vivo Drug Screens

Recently, there has been an increased interest in using whole animals to screen large chemical libraries. Such screens could potentially yield hits in a context in which relevant biological systems are present and functioning together in an intact organism. Though screens in mammalian models such as mice and rats are not practical due to the time and costs that would invariably be involved, smaller organisms whose biology has already been established to be relevant with respect to human disease are attractive candidates for use in drug discovery.

*Drosophila melanogaster* as a Tool for Drug Screens

The fruit fly (*D. melanogaster*) is a model organism which has been applied to the study of human genetics and development due to its small size, short generation time, prolific reproduction, and genetic tractability (Beir E., 2005). *D. melanogaster*'s usefulness as a genetic tool has facilitated the development of high throughput in vivo screens for chemical suppressors of pathological phenotypes in genetically modified strains (e.g., U.S. Pat. No. 6,316,690). While such screens may provide lead compounds which have been identified in an in vivo context, they rely on flies with artificial genetic backgrounds that often do not develop or behave like wild-type flies. In addition, *D. melanogaster* is an invertebrate, and as a result many aspects of its development, metabolism, and morphology can be markedly different from those of mammals.

SUMMARY OF THE INVENTION

The present invention provides a process for preparing information that identifies a compound as capable of perturbing the epithelium in a *D. melanogaster* comprising the steps of:

i) obtaining at least one *D. melanogaster* which is genetically unmodified except that the *D. melanogaster* optionally comprises at least one nucleotide sequence encoding a reporter polypeptide operably linked to a promoter of an endogenous protein;

ii) contacting the at least one *D. melanogaster* with the compound; and iii) determining whether there is a difference between the epithelium of the at least one *D. melanogaster* of ii) and the epithelium of a corresponding at least one *D. melanogaster* not contacted with the compound, wherein the presence of a difference between the epithelium of the at least one *D. melanogaster* contacted with the compound and the epithelium of a corresponding at least one *D. melanogaster* not contacted with the compound identifies the compound as a compound that is capable of perturbing the epithelium in a *D. melanogaster*.

The present invention provides a process for preparing information that identifies whether a compound is an epithelial cancer drug candidate comprising:

i) obtaining at least one *D. melanogaster* egg chamber which is genetically unmodified except that the at least one *D. melanogaster* egg chamber optionally comprises at least one nucleotide sequence encoding a reporter polypeptide operably linked to a promoter of an endogenous protein;

ii) contacting the at least one egg chamber with the compound; and iii) determining whether there is a difference between the follicular epithelium of the at least one egg chamber contacted with the compound and the follicular epithelium of a corresponding at least one egg chamber not contacted with the compound, wherein the presence of a difference between the follicular epithelium of the at least one egg chamber contacted with the compound and the follicular epithelium of a corresponding at least one egg chamber not contacted with the compound identifies the compound as an epithelial cancer drug candidate.

The present invention provides a process of producing an epithelial cancer drug comprising:

i) obtaining at least one *D. melanogaster* egg chamber which is genetically unmodified except that the at least one *D. melanogaster* egg chamber optionally comprises at least one nucleotide sequence encoding a reporter polypeptide operably linked to a promoter of an endogenous protein;

ii) contacting the at least one egg chamber with the compound;
iii) determining whether there is a difference between the follicular epithelium of the at least one egg chamber contacted with the compound and the follicular epithelium of a corresponding at least one egg chamber not contacted with the compound, wherein the presence of a difference between the follicular epithelium of the at least one egg chamber contacted with the compound and the follicular epithelium of the corresponding at least one egg chamber not contacted with the compound identifies the compound as an epithelial cancer drug; and
iv) producing the compound identified in step iii), thereby producing the epithelial cancer drug.

The present invention provides a process for preparing information that identifies whether a compound is an epithelial cancer drug candidate comprising:
i) obtaining at least one *D. melanogaster* egg chamber which is genetically unmodified except that the at least one *D. melanogaster* egg chamber optionally comprises at least one nucleotide sequence encoding a reporter polypeptide operably linked to a promoter of an endogenous protein;
ii) contacting the at least one egg chamber with the compound, and up to four additional compounds;
iii) determining whether there is a difference between the follicular epithelium of the at least one egg chamber contacted with the compound and up to four additional compounds and the follicular epithelium of a corresponding at least one egg chamber not contacted with the compound and up to four additional compounds;
iv) if there is a difference between the follicular epithelium of the at least one egg chamber contacted with the compound and up to four additional compounds and the follicular epithelium of the corresponding at least one egg chamber not contacted with the compound, contacting at least one additional egg chamber according to step i) with the compound but not the additional compound or compounds of step ii) and step iii); and
v) determining whether there is a difference between the follicular epithelium of the at least one additional egg chamber of step iv) and the follicular epithelium of a corresponding at least one additional egg chamber not contacted with the compound,
wherein the presence of a difference between the follicular epithelium of the at least one additional egg chamber of iv) and the follicular epithelium of the corresponding at least one additional egg chamber not contacted with the compound identifies the compound as an epithelial cancer drug candidate.

The present invention provides a process of producing an epithelial cancer drug comprising:
i) obtaining at least one *D. melanogaster* egg chamber which is genetically unmodified except that the at least one *D. melanogaster* egg chamber optionally comprises at least one nucleotide sequence encoding a reporter polypeptide operably linked to a promoter of an endogenous protein;
ii) contacting the at least one egg chamber with the compound, and up to four additional compounds;
iii) determining whether there is a difference between the follicular epithelium of the at least one egg chamber contacted with the compound and up to four additional compounds and the follicular epithelium of a corresponding at least one egg chamber not contacted with the compound and up to four additional compounds;
iv) if there is a difference between the follicular epithelium of the at least one egg chamber contacted with the compound and up to four additional compounds and the follicular epithelium of the corresponding at least one egg chamber not contacted with the compound, contacting at least one additional egg chamber according to step i) with the compound but not the additional compound or compounds of step ii) and step iii); and
v) determining whether the there is a difference between the follicular epithelium of the at least one additional egg chamber of step iv) and the follicular epithelium of the corresponding at least one additional egg chamber not contacted with the compound, wherein the presence of a difference between the follicular epithelium of the at least one additional egg chamber of step iv) and the follicular epithelium of the corresponding at least one additional egg chamber not contacted with the compound identifies the compound as an epithelial cancer drug; and
vi) producing the compound identified in step v), thereby producing the epithelial cancer drug.

The present invention provides a process for preparing information that identifies whether a compound is an epithelial cancer drug candidate comprising:
i) obtaining at least one *D. melanogaster* egg chamber which is genetically unmodified except that the at least one *D. melanogaster* egg chamber optionally comprises at least one nucleotide sequence encoding a reporter polypeptide operably linked to a promoter of an endogenous protein;
ii) contacting the at least one egg chamber with the compound;
iii) determining whether there is a difference between the follicular epithelium of the at least one egg chamber contacted with the compound and the follicular epithelium of a corresponding at least one egg chamber not contacted with the compound; and
iv) observing whether there is substantially more toxicity among cells other than follicle cells of the at least one egg chamber contacted with the compound than in the corresponding at least one egg chamber not contacted with the compound,
wherein the presence of a difference between the follicular epithelium of the at least one egg chamber contacted with the compound and the follicular epithelium of the corresponding at least one egg chamber not contacted with the compound, without the presence of substantially more toxicity among cells other than follicle cells of the at least one egg chamber contacted with the compound than in the corresponding at least one egg chamber not contacted with the compound, identifies the compound as an epithelial cancer drug candidate.

The present invention provides a process of producing an epithelial cancer drug comprising:
i) preparing or obtaining a group of compounds to be screened;
ii) performing a process of the invention for each compound from the group of compounds to identify an epithelial cancer drug candidate; and
iii) producing the compound identified in step ii), thereby producing the epithelial cancer drug.

The present invention provides a process of preparing an epithelial cancer drug comprising:
i) preparing or obtaining a group of compounds to be screened;
ii) performing a process of the invention for each compound from the group of compounds to identify an epithelial cancer drug candidate;
iii) producing the compound identified in step ii), thereby producing the epithelial cancer drug; and
iv) preparing the identified epithelial cancer drug candidate for use in treating an epithelial cancer.

The present invention provides novel drug screening processes in *D. melanogaster* that overcome limitations of previous approaches.

The present invention provides a process for preparing information that identifies a compound as capable of perturbing the epithelium in a *D. melanogaster* comprising the steps of:
i) obtaining a *D. melanogaster* which is genetically unmodified except that the *D. melanogaster* optionally comprises at least one nucleotide sequence encoding a reporter polypeptide operably linked to a promoter of an endogenous protein;
ii) contacting the *D. melanogaster* with the compound; and
iii) determining whether there is a difference between the epithelium of the *D. melanogaster* of ii) and the epithelium of a corresponding *D. melanogaster* not contacted with the compound,
wherein the presence of a difference between the epithelium of the *D. melanogaster* contacted with the compound and the epithelium of a corresponding *D. melanogaster* not contacted with the compound identifies the compound as a compound that is capable of perturbing the epithelium in a *D. melanogaster*.

Aspects of the present invention provide a process for preparing information that identifies whether a compound is an epithelial cancer drug candidate comprising:
i) obtaining a *D. melanogaster* egg chamber which is genetically unmodified except that the *D. melanogaster* egg chamber optionally comprises at least one nucleotide sequence encoding a reporter polypeptide operably linked to a promoter of an endogenous protein;
ii) contacting the egg chamber with the compound; and
iii) determining whether there is a difference between the follicular epithelium of the egg chamber contacted with the compound and the follicular epithelium of an egg chamber not contacted with the compound,
wherein the presence of a difference between the follicular epithelium of an egg chamber contacted with the compound and the follicular epithelium of a corresponding egg chamber not contacted with the compound identifies the compound as an epithelial cancer drug candidate.

Aspects of the present invention provide a process of producing an epithelial cancer drug comprising:
i) obtaining a *D. melanogaster* egg chamber which is genetically unmodified except that the *D. melanogaster* egg chamber optionally comprises at least one nucleotide sequence encoding a reporter polypeptide operably linked to a promoter of an endogenous protein;
ii) contacting the egg chamber with the compound;
iii) determining whether there is a difference between the follicular epithelium of the egg chamber contacted with the compound and the follicular epithelium of an egg chamber not contacted with the compound, wherein the presence of a difference between the follicular epithelium of an egg chamber contacted with the compound and the follicular epithelium of a corresponding egg chamber not contacted with the compound identifies the compound as an epithelial cancer drug; and
iv) producing the compound identified in step iii), thereby producing the epithelial cancer drug.

Aspects of the present invention provide a process for preparing information that identifies whether a compound is an epithelial cancer drug candidate comprising:
i) obtaining a *D. melanogaster* egg chamber which is genetically unmodified except that the *D. melanogaster* egg chamber optionally comprises at least one nucleotide sequence encoding a reporter polypeptide operably linked to a promoter of an endogenous protein;
ii) contacting the egg chamber with the compound, and up to four additional compounds;
iii) determining whether there is a difference between follicular epithelium of the egg chamber contacted with the compound and up to four additional compounds and the follicular epithelium of an egg chamber not contacted with the compound and up to four additional compounds;
iv) if there is a difference between the follicular epithelium of the egg chamber contacted with the compound and up to four additional compounds and the follicular epithelium of an egg chamber not contacted with the compound, contacting at least one additional egg chamber according to step i) with the compound but not the additional compound or compounds of step ii) and step iii); and
v) determining whether there is a difference between the follicular epithelium of the egg chamber of step iv) and the follicular epithelium of an egg chamber not contacted with the compound,
wherein the presence of a difference between the follicular epithelium of the egg chamber of iv) and the follicular epithelium of an egg chamber not contacted with the compound identifies the compound as an epithelial cancer drug candidate.

Aspects of the present invention provide a process of producing an epithelial cancer drug comprising:
i) obtaining a *D. melanogaster* egg chamber which is genetically unmodified except that the *D. melanogaster* egg chamber optionally comprises at least one nucleotide sequence encoding a reporter polypeptide operably linked to a promoter of an endogenous protein;
ii) contacting the egg chamber with the compound, and up to four additional compounds;
iii) determining whether there is a difference between follicular epithelium of the egg chamber contacted with the compound and up to four additional compounds and the follicular epithelium of an egg chamber not contacted with the compound and up to four additional compounds;
iv) if there is a difference between the follicular epithelium of the egg chamber contacted with the compound and up to four additional compounds and the follicular epithelium of an egg chamber not contacted with the compound, contacting at least one additional egg chamber according to step i) with the compound but not the additional compound or compounds of step ii) and step iii); and
v) determining whether the there is a difference between the follicular epithelium of the egg chamber of step iv) and the follicular epithelium of an egg chamber not contacted with the compound, wherein the presence of a difference between the follicular epithelium of the egg chamber of step iv) and the follicular epithelium of a corresponding egg chamber not contacted with the compound identifies the compound as an epithelial cancer drug; and
vi) producing the compound identified in step v), thereby producing the epithelial cancer drug.

Aspects of the present invention provide a process for preparing information that identifies whether a compound is an epithelial cancer drug candidate comprising:
i) obtaining a *D. melanogaster* egg chamber which is genetically unmodified except that the *D. melanogaster* egg chamber optionally comprises at least one nucleotide sequence encoding a reporter polypeptide operably linked to a promoter of an endogenous protein;
ii) contacting the egg chamber with the compound;
iii) determining whether there is a difference between the follicular epithelium of the egg chamber contacted with the compound and the follicular epithelium of an egg chamber not contacted with the compound; and iv) observing whether there is more toxicity among cells other than follicle cells of the egg chamber contacted with the compound than in the egg chamber not contacted with the compound, wherein the presence of a difference between the follicular epithelium of an egg chamber contacted with the compound and the follicular epithelium of a corresponding egg chamber not contacted with the compound, without the presence of substantially more toxicity among cells other than follicle cells of the egg chamber contacted with the compound than in the egg chamber not contacted with the compound, identifies the compound as an epithelial cancer drug candidate.

DETAILED DESCRIPTION OF THE INVENTION

The present invention provides a process for preparing information that identifies a compound as capable of perturbing the epithelium in a D. melanogaster comprising the steps of:

i) obtaining at least one D. melanogaster which is genetically unmodified except that the D. melanogaster optionally comprises at least one nucleotide sequence encoding a reporter polypeptide operably linked to a promoter of an endogenous protein;

ii) contacting the at least one D. melanogaster with the compound; and iii) determining whether there is a difference between the epithelium of the at least one D. melanogaster of ii) and the epithelium of a corresponding at least one D. melanogaster not contacted with the compound, wherein the presence of a difference between the epithelium of the at least one D. melanogaster contacted with the compound and the epithelium of a corresponding at least one D. melanogaster not contacted with the compound identifies the compound as a compound that is capable of perturbing the epithelium in a D. melanogaster.

In some embodiments, the process further comprises identifying whether a compound that is capable of perturbing the epithelium in a D. melanogaster specifically perturbs the epithelium by determining whether there is a difference between non-epithelial tissue of the at least one D. melanogaster contacted with the compound and the non-epithelial tissue of a corresponding at least one D. melanogaster not contacted with the compound, wherein when there is no difference between the non-epithelial tissue of the at least one D. melanogaster contacted with the compound and the non-epithelial tissue of a corresponding at least one D. melanogaster not contacted with the compound, the compound is identified as a compound that specifically perturbs the epithelium in a D. melanogaster.

In some embodiments, the at least one D. melanogaster comprises at least one nucleotide sequence encoding a reporter polypeptide operably linked to a promoter of an endogenous protein, and the reporter polypeptide is part of a fusion protein which comprises the endogenous protein.

In some embodiments, the endogenous protein is atypical kinase C (aPKC), Par3, Par6, Cdc42, DE-Cadherin, Crumbs (Crb), Stardust (Sdt), PATJ, Lin-7, beta-catenin, or Armadillo (Arm).

In some embodiments, the endogenous protein is Par6.

In some embodiments, the at least one D. melanogaster is an at least one D. melanogaster embryo.

In some embodiments, contacting the at least one D. melanogaster embryo with the compound comprises injecting the compound into the at least one D. melanogaster embryo.

In some embodiments, the at least one D. melanogaster is an at least one female D. melanogaster, and the epithelium is the follicular epithelium of an egg chamber of the at least one female D. melanogaster.

In some embodiments, a compound which perturbs or specifically perturbs the epithelium in a D. melanogaster is an epithelial cancer drug candidate.

The present invention provides a process for preparing information that identifies whether a compound is an epithelial cancer drug candidate comprising:

i) obtaining at least one D. melanogaster egg chamber which is genetically unmodified except that the at least one D. melanogaster egg chamber optionally comprises at least one nucleotide sequence encoding a reporter polypeptide operably linked to a promoter of an endogenous protein;

ii) contacting the at least one egg chamber with the compound; and iii) determining whether there is a difference between the follicular epithelium of the at least one egg chamber contacted with the compound and the follicular epithelium of a corresponding at least one egg chamber not contacted with the compound, wherein the presence of a difference between the follicular epithelium of the at least one egg chamber contacted with the compound and the follicular epithelium of a corresponding at least one egg chamber not contacted with the compound identifies the compound as an epithelial cancer drug candidate.

The present invention provides a process of producing an epithelial cancer drug comprising:

i) obtaining at least one D. melanogaster egg chamber which is genetically unmodified except that the at least one D. melanogaster egg chamber optionally comprises at least one nucleotide sequence encoding a reporter polypeptide operably linked to a promoter of an endogenous protein;

ii) contacting the at least one egg chamber with the compound;

iii) determining whether there is a difference between the follicular epithelium of the at least one egg chamber contacted with the compound and the follicular epithelium of a corresponding at least one egg chamber not contacted with the compound, wherein the presence of a difference between the follicular epithelium of the at least one egg chamber contacted with the compound and the follicular epithelium of the corresponding at least one egg chamber not contacted with the compound identifies the compound as an epithelial cancer drug; and iv) producing the compound identified in step iii), thereby producing the epithelial cancer drug.

In some embodiments, the at least one D. melanogaster egg chamber comprises at least one nucleotide sequence encoding a reporter polypeptide operably linked to a promoter of an endogenous protein, and the reporter polypeptide is part of a fusion protein which comprises the endogenous protein.

In some embodiments, the endogenous protein is atypical kinase C (aPKC), Par3, Par6, Cdc42, DE-Cadherin, Crumbs (Crb), Stardust (Sdt), PATJ, Lin-7, beta-catenin, or Armadillo (Arm).

In some embodiments, the endogenous protein is Par6.

In some embodiments, the difference between the follicular epithelium of the at least one egg chamber contacted with the compound and the follicular epithelium of the corresponding at least one egg chamber not contacted with the compound is altered expression of the fusion protein in the follicular epithelium.

In some embodiments, altered expression of the fusion protein comprises increased expression of the fusion protein in the follicular epithelium of the at least one egg chamber contacted with the compound compared to the follicular epithelium of the corresponding at least one egg chamber not contacted with the compound.

In some embodiments, altered expression of the fusion protein comprises decreased expression of the fusion protein in the follicular epithelium of the at least one egg chamber contacted with the compound compared to the follicular epithelium of the corresponding at least one egg chamber not contacted with the compound.

In some embodiments, altered expression of the fusion protein comprises a different localization of the fusion protein within follicle epithelial cells of the at least one egg chamber contacted with the compound compared to follicle epithelial cells of the corresponding at least one egg chamber not contacted with the compound.

In some embodiments, there is proportionally less localization of the fusion protein at the apical side of the follicle epithelial cells of the at least one egg chamber contacted with the compound compared to the follicle epithelial cells of the corresponding at least one egg chamber not contacted with the compound.

In some embodiments, altered expression of the fusion protein comprises a different location of protein production and/or post-transcriptional modification of the fusion protein in the follicular epithelium of the at least one egg chamber contacted with the compound compared to the follicular epithelium of the corresponding at least one egg chamber not contacted with the compound.

In some embodiments, the difference between the follicular epithelium of the at least one egg chamber contacted with the compound and the follicular epithelium of the corresponding at least one egg chamber not contacted with the compound is altered architecture of the follicular epithelium of the at least one egg chamber contacted with the compound compared to the follicular epithelium of the corresponding at least one egg chamber not contacted with the compound.

In some embodiments, the altered architecture comprises multilayering of follicle cells.

In some embodiments, the altered architecture comprises a change in the shape of a subtype of follicle cells.

In some embodiments, the difference between the follicular epithelium of the at least one egg chamber contacted with the compound and the follicular epithelium of the corresponding at least one egg chamber not contacted with the compound is altered migration of a subtype of follicle cells within the follicular epithelium of the at least one egg chamber contacted with the compound compared to the same subtype of follicle cells within the follicular epithelium of the corresponding at least one egg chamber not contacted with the compound.

In some embodiments, the subtype of follicle cells is selected from the group consisting of border cells, stretch cells, polar cells, and centripetal cells.

The present invention provides a process for preparing information that identifies whether a compound is an epithelial cancer drug candidate comprising:
i) obtaining at least one *D. melanogaster* egg chamber which is genetically unmodified except that the at least one *D. melanogaster* egg chamber optionally comprises at least one nucleotide sequence encoding a reporter polypeptide operably linked to a promoter of an endogenous protein;
ii) contacting the at least one egg chamber with the compound, and up to four additional compounds;
iii) determining whether there is a difference between the follicular epithelium of the at least one egg chamber contacted with the compound and up to four additional compounds and the follicular epithelium of a corresponding at least one egg chamber not contacted with the compound and up to four additional compounds;
iv) if there is a difference between the follicular epithelium of the at least one egg chamber contacted with the compound and up to four additional compounds and the follicular epithelium of the corresponding at least one egg chamber not contacted with the compound, contacting at least one additional egg chamber according to step i) with the compound but not the additional compound or compounds of step ii) and step iii); and
v) determining whether there is a difference between the follicular epithelium of the at least one additional egg chamber of step iv) and the follicular epithelium of a corresponding at least one additional egg chamber not contacted with the compound,
  wherein the presence of a difference between the follicular epithelium of the at least one additional egg chamber of iv) and the follicular epithelium of the corresponding at least one additional egg chamber not contacted with the compound identifies the compound as an epithelial cancer drug candidate.

The present invention provides a process of producing an epithelial cancer drug comprising:
i) obtaining at least one *D. melanogaster* egg chamber which is genetically unmodified except that the at least one *D. melanogaster* egg chamber optionally comprises at least one nucleotide sequence encoding a reporter polypeptide operably linked to a promoter of an endogenous protein;
ii) contacting the at least one egg chamber with the compound, and up to four additional compounds;
iii) determining whether there is a difference between the follicular epithelium of the at least one egg chamber contacted with the compound and up to four additional compounds and the follicular epithelium of a corresponding at least one egg chamber not contacted with the compound and up to four additional compounds;
iv) if there is a difference between the follicular epithelium of the at least one egg chamber contacted with the compound and up to four additional compounds and the follicular epithelium of the corresponding at least one egg chamber not contacted with the compound, contacting at least one additional egg chamber according to step i) with the compound but not the additional compound or compounds of step ii) and step iii); and
v) determining whether the there is a difference between the follicular epithelium of the at least one additional egg chamber of step iv) and the follicular epithelium of the corresponding at least one additional egg chamber not contacted with the compound, wherein the presence of a difference between the follicular epithelium of the at least one additional egg chamber of step iv) and the follicular epithelium of the corresponding at least one additional egg chamber not contacted with the compound identifies the compound as an epithelial cancer drug; and
vi) producing the compound identified in step v), thereby producing the epithelial cancer drug.

The present invention provides a process for preparing information that identifies whether a compound is an epithelial cancer drug candidate comprising:
i) obtaining at least one *D. melanogaster* egg chamber which is genetically unmodified except that the at least one *D. melanogaster* egg chamber optionally comprises at least one nucleotide sequence encoding a reporter polypeptide operably linked to a promoter of an endogenous protein;
ii) contacting the at least one egg chamber with the compound;

iii) determining whether there is a difference between the follicular epithelium of the at least one egg chamber contacted with the compound and the follicular epithelium of a corresponding at least one egg chamber not contacted with the compound; and iv) observing whether there is substantially more toxicity among cells other than follicle cells of the at least one egg chamber contacted with the compound than in the corresponding at least one egg chamber not contacted with the compound, wherein the presence of a difference between the follicular epithelium of the at least one egg chamber contacted with the compound and the follicular epithelium of the corresponding at least one egg chamber not contacted with the compound, without the presence of substantially more toxicity among cells other than follicle cells of the at least one egg chamber contacted with the compound than in the corresponding at least one egg chamber not contacted with the compound, identifies the compound as an epithelial cancer drug candidate.

In some embodiments, the presence of substantially more toxicity is observed in all cells other than follicle cells of the at least one egg chamber.

In some embodiments, the presence of substantially more toxicity is observed in one or more nurse cells of the at least one egg chamber.

In some embodiments, the presence of substantially more toxicity is observed in the oocyte of the at least one egg chamber.

In some embodiments, toxicity is determined by morphology.

In some embodiments, toxicity is increased cell death.

In some embodiments, the presence of more cell death is due to apoptosis.

In some embodiments, the presence of more cell death is due to necrosis.

In some embodiments, 10 to 30 *D. melanogaster* egg chambers are obtained and contacted with the compound.

In some embodiments, about 10, 15, 20, 25, or 30 *D. melanogaster* egg chambers are obtained and contacted with the compound.

In some embodiments, at least 10, 15, 20, 25, or 30 *D. melanogaster* egg chambers are obtained and contacted with each compound.

In some embodiments, 20 *D. melanogaster* egg chambers are obtained and contacted with the compound.

The present invention provides a process of producing an epithelial cancer drug comprising:
i) preparing or obtaining a group of compounds to be screened;
ii) performing a process of the invention for each compound from the group of compounds to identify an epithelial cancer drug candidate; and
iii) producing the compound identified in step ii), thereby producing the epithelial cancer drug.

The present invention provides a process of preparing an epithelial cancer drug comprising:
i) preparing or obtaining a group of compounds to be screened;
ii) performing a process of the invention for each compound from the group of compounds to identify an epithelial cancer drug candidate;
iii) producing the compound identified in step ii), thereby producing the epithelial cancer drug; and
iv) preparing the identified epithelial cancer drug candidate for use in treating an epithelial cancer.

In some embodiments, a process of the invention is performed for each compound in at least one well of a microwell plate, wherein the microwell plate has multiple wells such that a process of the invention may be performed for more than one compound from the group of compounds using the microwell plate.

In some embodiments, a process of the invention is performed for more than one compound from the group of compounds using the microwell plate.

In some embodiments, 10 to 30 *D. melanogaster* egg chambers are obtained and contacted with each compound.

In some embodiments, about 10, 15, 20, 25, or 30 *D. melanogaster* egg chambers are obtained and contacted with each compound.

In some embodiments, at least 10, 15, 20, 25, or 30 *D. melanogaster* egg chambers are obtained and contacted with each compound.

In some embodiments, 20 *D. melanogaster* egg chambers are obtained and contacted with each compound.

The present invention provides a process for preparing information that identifies a compound as capable of perturbing the epithelium in a *D. melanogaster* comprising the steps of:
i) obtaining a *D. melanogaster* which is genetically unmodified except that the *D. melanogaster* optionally comprises at least one nucleotide sequence encoding a reporter polypeptide operably linked to a promoter of an endogenous protein;
ii) contacting the *D. melanogaster* with the compound; and
iii) determining whether there is a difference between the epithelium of the *D. melanogaster* of ii) and the epithelium of a corresponding *D. melanogaster* not contacted with the compound, wherein the presence of a difference between the epithelium of the *D. melanogaster* contacted with the compound and the epithelium of a corresponding *D. melanogaster* not contacted with the compound identifies the compound as a compound that is capable of perturbing the epithelium in a *D. melanogaster*.

In some embodiments the process further comprises identifying whether a compound that is capable of perturbing the epithelium in a *D. melanogaster* specifically perturbs the epithelium by determining whether there is a difference between non-epithelial tissue of the *D. melanogaster* contacted with the compound and the non-epithelial tissue of a corresponding *D. melanogaster* not contacted with the compound, wherein when there is no difference between the non-epithelial tissue of the *D. melanogaster* contacted with the compound and the non-epithelial tissue of a corresponding *D. melanogaster* not contacted with the compound, the compound is identified as a compound that specifically perturbs the epithelium in a *D. melanogaster*.

In some embodiments, the *D. melanogaster* comprises at least one nucleotide sequence encoding a reporter polypeptide operably linked to a promoter of an endogenous protein, and the reporter polypeptide is part of a fusion protein which comprises the endogenous protein.

In some embodiments, the endogenous protein is atypical kinase C (aPKC), Par3, Par6, Cdc42, DE-Cadherin, Crumbs (Crb), Stardust (Sdt), PATJ, Lin-7, beta-catenin, or Armadillo (Arm).

In some embodiments, the endogenous protein is Par6.

In some embodiments, the *D. melanogaster* is a *D. melanogaster* embryo.

In some embodiments, contacting the *D. melanogaster* embryo with the compound comprises injecting the compound into the *D. melanogaster* embryo.

In some embodiments, the *D. melanogaster* is a female *D. melanogaster*, and the epithelium is the follicular epithelium of an egg chamber of the female *D. melanogaster*.

In some embodiments, a compound which perturbs or specifically perturbs the epithelium in a *D. melanogaster* is an epithelial cancer drug candidate.

Aspects of the present invention provide a process for preparing information that identifies whether a compound is an epithelial cancer drug candidate comprising:
i) obtaining a *D. melanogaster* egg chamber which is genetically unmodified except that the *D. melanogaster* egg chamber optionally comprises at least one nucleotide sequence encoding a reporter polypeptide operably linked to a promoter of an endogenous protein;
ii) contacting the egg chamber with the compound; and
iii) determining whether there is a difference between the follicular epithelium of the egg chamber contacted with the compound and the follicular epithelium of an egg chamber not contacted with the compound,
wherein the presence of a difference between the follicular epithelium of an egg chamber contacted with the compound and the follicular epithelium of a corresponding egg chamber not contacted with the compound identifies the compound as an epithelial cancer drug candidate.

Aspects of the present invention provide a process of producing an epithelial cancer drug comprising:
i) obtaining a *D. melanogaster* egg chamber which is genetically unmodified except that the *D. melanogaster* egg chamber optionally comprises at least one nucleotide sequence encoding a reporter polypeptide operably linked to a promoter of an endogenous protein;
ii) contacting the egg chamber with the compound;
iii) determining whether there is a difference between the follicular epithelium of the egg chamber contacted with the compound and the follicular epithelium of an egg chamber not contacted with the compound, wherein the presence of a difference between the follicular epithelium of an egg chamber contacted with the compound and the follicular epithelium of a corresponding egg chamber not contacted with the compound identifies the compound as an epithelial cancer drug; and
iv) producing the compound identified in step iii), thereby producing the epithelial cancer drug.

In some embodiments, the *D. melanogaster* egg chamber comprises at least one nucleotide sequence encoding a reporter polypeptide operably linked to a promoter of an endogenous protein, and the reporter polypeptide is part of a fusion protein which comprises the endogenous protein.

In some embodiments, the endogenous protein is atypical kinase C (aPKC), Par3, Par1, Cdc42, DE-Cadherin, Crumbs (Crb), Stardust (Sdt), PATJ, Lin-7, beta-catenin, or Armadillo (Arm).

In some embodiments, the endogenous protein is Par6.

In some embodiments, the difference between the follicular epithelium of an egg chamber contacted with the compound and the follicular epithelium of a corresponding egg chamber not contacted with the compound is altered expression of the fusion protein in follicular epithelium.

In some embodiments, altered expression of the fusion protein comprises increased expression of the fusion protein in follicular epithelium of the egg chamber contacted with the compound compared to the follicular epithelium of a corresponding egg chamber not contacted with the compound.

In some embodiments, altered expression of the fusion protein comprises decreased expression of the fusion protein in follicular epithelium of the egg chamber contacted with the compound compared to follicular epithelium of a corresponding egg chamber not contacted with the compound.

In some embodiments, altered expression of the fusion protein comprises a different localization of the fusion protein within follicle epithelial cells of the egg chamber contacted with the compound compared to follicle epithelial cells of a corresponding egg chamber not contacted with the compound.

In some embodiments, there is proportionally less localization of the fusion protein at the apical side of the follicle epithelial cells of the egg chamber contacted with the compound compared to follicle epithelial cells of a corresponding egg chamber not contacted with the compound.

In some embodiments, altered expression of the fusion protein comprises a different location of protein production and/or post-transcriptional modification of the fusion protein in the follicular epithelium of the egg chamber contacted with the compound compared to the follicular epithelium of a corresponding egg chamber not contacted with the compound.

In some embodiments, the difference between the follicular epithelium of an egg chamber contacted with the compound and the follicular epithelium of an egg chamber not contacted with the compound is altered architecture of the follicular epithelium compared to the follicular epithelium a corresponding egg chamber not contacted with the compound.

In some embodiments, the altered architecture comprises multilayering of follicle cells.

In some embodiments, the altered architecture comprises a change in the shape of a subtype of follicle cells.

In some embodiments, the difference between the follicular epithelium of an egg chamber contacted with the compound and the follicular epithelium of an egg chamber not contacted with the compound is altered migration of a subtype of follicle cells within the follicular epithelium compared to the same subtype of follicle cells within the follicular epithelium an egg chamber not contacted with the compound.

In some embodiments, the subtype of follicle cells is selected from the group consisting of border cells, stretch cells, polar cells, and centripetal cells.

Aspects of the present invention provide a process for preparing information that identifies whether a compound is an epithelial cancer drug candidate comprising:
i) obtaining a *D. melanogaster* egg chamber which is genetically unmodified except that the *D. melanogaster* egg chamber optionally comprises at least one nucleotide sequence encoding a reporter polypeptide operably linked to a promoter of an endogenous protein;
ii) contacting the egg chamber with the compound, and up to four additional compounds;
iii) determining whether there is a difference between follicular epithelium of the egg chamber contacted with the compound and up to four additional compounds and the follicular epithelium of an egg chamber not contacted with the compound and up to four additional compounds;
iv) if there is a difference between the follicular epithelium of the egg chamber contacted with the compound and up to four additional compounds and the follicular epithelium of an egg chamber not contacted with the compound, contacting at least one additional egg chamber according to step i) with the compound but not the additional compound or compounds of step ii) and step iii); and
v) determining whether there is a difference between the follicular epithelium of the egg chamber of step iv) and the follicular epithelium of an egg chamber not contacted with the compound, wherein the presence of a difference between the follicular epithelium of the egg chamber of iv) and the follicular epithelium of an egg chamber not contacted with the compound identifies the compound as an epithelial cancer drug candidate.

Aspects of the present invention provide a process of producing an epithelial cancer drug comprising:
i) obtaining a *D. melanogaster* egg chamber which is genetically unmodified except that the *D. melanogaster* egg chamber optionally comprises at least one nucleotide sequence encoding a reporter polypeptide operably linked to a promoter of an endogenous protein;
ii) contacting the egg chamber with the compound, and up to four additional compounds;
iii) determining whether there is a difference between follicular epithelium of the egg chamber contacted with the compound and up to four additional compounds and the follicular epithelium of an egg chamber not contacted with the compound and up to four additional compounds;
iv) if there is a difference between the follicular epithelium of the egg chamber contacted with the compound and up to four additional compounds and the follicular epithelium of an egg chamber not contacted with the compound, contacting at least one additional egg chamber according to step i) with the compound but not the additional compound or compounds of step ii) and step iii); and
v) determining whether the there is a difference between the follicular epithelium of the egg chamber of step iv) and the follicular epithelium of an egg chamber not contacted with the compound, wherein the presence of a difference between the follicular epithelium of the egg chamber of step iv) and the follicular epithelium of a corresponding egg chamber not contacted with the compound identifies the compound as an epithelial cancer drug; and
vi) producing the compound identified in step v), thereby producing the epithelial cancer drug.

Aspects of the present invention provide a process for preparing information that identifies whether a compound is an epithelial cancer drug candidate comprising:
i) obtaining a *D. melanogaster* egg chamber which is genetically unmodified except that the *D. melanogaster* egg chamber optionally comprises at least one nucleotide sequence encoding a reporter polypeptide operably linked to a promoter of an endogenous protein;
ii) contacting the egg chamber with the compound;
iii) determining whether there is a difference between the follicular epithelium of the egg chamber contacted with the compound and the follicular epithelium of an egg chamber not contacted with the compound; and
iv) observing whether there is more toxicity among cells other than follicle cells of the egg chamber contacted with the compound than in the egg chamber not contacted with the compound,
wherein the presence of a difference between the follicular epithelium of an egg chamber contacted with the compound and the follicular epithelium of a corresponding egg chamber not contacted with the compound, without the presence of substantially more toxicity among cells other than follicle cells of the egg chamber contacted with the compound than in the egg chamber not contacted with the compound, identifies the compound as an epithelial cancer drug candidate.

In some embodiments, the presence of more toxicity is observed in all cells other than follicle cells of the egg chamber.

In some embodiments, the presence of more toxicity is observed in one or more nurse cells of the egg chamber.

In some embodiments, the presence of more toxicity is observed in the oocyte of the egg chamber.

In some embodiments, toxicity is determined by morphology.

In some embodiments, toxicity is increased cell death.

In some embodiments, the presence of more cell death is due to apoptosis.

In some embodiments, the presence of more cell death is due to necrosis.

Each embodiment disclosed herein is contemplated as being applicable to each of the other disclosed embodiments. Thus, all combinations of the various elements described herein are within the scope of the invention.

It is understood that where a parameter range is provided, all integers within that range, and tenths thereof, are also provided by the invention. For example, "0.2-5 mg/kg/day" is a disclosure of 0.2 mg/kg/day, 0.3 mg/kg/day, 0.4 mg/kg/day, 0.5 mg/kg/day, 0.6 mg/kg/day etc. up to 5.0 mg/kg/day.

Terms

As used herein, and unless stated otherwise, each of the following terms shall have the definition set forth below.

As used herein, "about" in the context of a numerical value or range means±10% of the numerical value or range recited or claimed, unless the context requires a more limited range.

As used herein, a "cancer drug candidate" is a compound which is identified to produce a difference in a *D. melanogaster* which has been contacted with the compound, compared to a *D. melanogaster* which has not been contacted with the compound.

As used herein, "epithelial cancer" means a carcinoma. A carcinoma is a cancer derived from epithelial cells. Subtypes of carcinomas include but are not limited to adenocarcinoma, squamous cell carcinoma, adenosquamous carcinoma, anaplastic carcinoma, large cell carcinoma, small cell carcinoma, giant cell carcinoma, spindle cell carcinoma, sarcomatoid carcinoma, pleomorphic carcinoma, carcinosarcoma, pulmonary blastoma, basal cell carcinoma, linitis plastica, vipoma, cholangiocarcinoma, hepatocellular carcinoma, adenoid cystic carcinoma, renal cell carcinoma, adnexal and skin appendage neoplasms, mucoepidermoid neoplasms, and acinar cell neoplasms. The term carcinoma encompasses lung cancers, liver cancers, ovarian cancers, brain cancers, breast cancers, prostate cancers, colon cancers, pancreatic cancers, and brain cancers, of epithelial origin.

As used herein, "*D. melanogaster*" refers to an insect or insects as well as to parts of the insect belonging to the species *Drosophila melanogaster*, without regard to the developmental stage thereof and including, embryos (eggs), larvae, pupae, and mature adult flies of the insect, unless a specific developmental stage or a specific part is specified.

As used herein in regard to cell and tissue function, to "perturb" means to alter an aspect of the normal cell and tissue function of an organism, including but not limited to the embryonic development of a *D. melanogaster*, the development of an epithelium within a *D. melanogaster*, the development of a structure or tissue within a *D. melanogaster* such as an egg chamber of a *D. melanogaster*, or the development of an epithelium within a part of a *D. melanogaster*, such as an egg chamber. To perturb cell and tissue function of an epithelium, may mean to alter the normal growth, behavior, or morphology of a cell or the progeny thereof that is within a developing epithelium, and/or to alter the normal interaction or arrangement of cells or the progeny thereof that are within a developing epithelium, and/or to alter the normal growth, behavior, or morphology of a developing epithelium. To "perturb the epithelium" means to alter an aspect of a normal epithelial cell's function or of an epithelial tissue function in an organism or a part thereof.

As used herein, "epithelium" refers to tissue that lines the cavities and surfaces of an organism's body, and also form many glands. Types of *D. melanogaster* epitheliums include but are not limited to the follicular epithelium of the egg chamber, and the blastoderm epithelium, foregut epithelium, hindgut epithelium, neuroectodermal endothelium, subperineurium and peripheral glia, gonadal sheet, dorsal vessel, salivary glands, and malpighian tubules of the embryo.

As used herein, "follicular epithelium" or "follicle cell epithelium" means the somatic monolayer which surrounds the germ cells of a *Drosophila melanogaster* egg chamber. The follicular epithelium produces yolk and eggshell components of the egg, and also participates in signaling events with the germ cells that help determine future embryonic axes (Horne-Badovinac and Bilder, 2005).

As used herein, "follicle cell" means a cell which is part of, or derived from the follicular epithelium.

As used herein, "label" means a substance which may be introduced into a living or non-living cell such that it allows for the specific detection of a protein within the cell by any technique known in the art. The label may comprise a portion that is capable of binding to another protein, and a portion that is a marker. In some aspects of the invention, the portion that is capable of binding to another protein is attached to the marker by a covalent bond.

As used herein, a "marker" may be any molecule that provides an identifiable signal within a cell, or that facilitates the determination of the expression or location of a protein in a cell by any technique known in the art. Non-limiting examples of markers are fluorescent dyes, phosphorescent dyes, quantum dots, and reporter polypeptides.

As used herein, a "reporter polypeptide" is a protein or oligopeptide that provides an identifiable signal within a cell, or which is capable of being specifically detected within a cell by any technique known in the art. The cell may be alive or dead. Examples of reporter polypeptides include but are not limited to streptavidin, beta-galactosidase, epitope tags, fluorescent proteins, luminescent proteins and chromogenic enzymes such as horseradish peroxidase.

As used herein, an "epitope tag" is an amino acid sequence for which antibodies with suitable specificity and affinity have been generated, or may be generated.

As used herein, "altered expression" means having an amount or localization of a protein in a cell which is or was contacted with at least one compound, or the progeny thereof, compared to amount of localization of the protein in a corresponding untreated cell, or the progeny thereof. Altered expression of a protein may be increased expression of the protein, decreased expression of the protein, or a different localization of the protein within a cell or the progeny of the cell that is or has been contacted with at least one compound compared to a corresponding untreated cell or the progeny thereof. Altered expression may also be a different location of expression of the protein within a group of cells or a tissue in a *D. melanogaster* which is or has been contacted with at least one compound, compared to a corresponding group of cells or tissue in an untreated *D. melanogaster*, for example, within the follicular epithelium of an egg chamber of a *D. melanogaster*.

As used herein, "altered architecture" means a different number, shape, and/or arrangement of cells within a group of cells or a tissue of a *D. melanogaster* which is or has been contacted with at least one compound compared to a corresponding group of cells or tissue in an untreated *D. melanogaster*. In one non-limiting example, altered architecture may be the multilayering of cells in a *D. melanogaster* which has been contacted with a compound in a location where the corresponding cells an untreated *D. melanogaster* form a monolayer.

As used herein, "incubation medium" means growth medium which contains a compound with which a *D. melanogaster* egg chamber will be contacted and/or is being contacted and/or was contacted.

As used herein, a "fluorophore" is a molecule which absorbs electromagnetic energy at one wavelength and re-emits energy at another wavelength. A fluorophore may be a molecule or part of a molecule including fluorescent dyes and proteins.

Labels, Markers, and Reporter Polypeptides

Aspects of the invention relate to the detection of a labeled protein or a fusion protein within a *D. melanogaster*. The label may be used to specifically detect the presence and/or the amount and/or the localization of any endogenous protein which is expressed in the epithelium of a *D. melanogaster*. The label may also be used to detect the presence of a fusion protein which is expressed in the epithelium of a *D. melanogaster*. The fusion protein may comprise amino acids in the sequence of the amino acid sequence of an endogenous protein melanogaster and the amino acid sequence of a reporter polypeptide. In some embodiments, the protein which is expressed in the epithelium of a wild-type *D. melanogaster* is atypical kinase C (aPKC), Par3, Par6, Cdc42, DE-Cadherin, Crumbs (Crb), Stardust (Sdt), PATj, Lin-7, beta-catenin, or Armadillo (Arm). In some embodiments which comprise a label, the protein to which the label binds is Par6. In some embodiments which comprise a fusion protein, the fusion protein comprises amino acids in the amino acid sequence of Par6 and the amino acid sequence of a reporter polypeptide. The label may comprise a portion that is capable of binding to a protein or fusion protein, and a marker. The portion of the label which is capable of binding to a protein or fusion protein may be covalently attached to the marker.

One of skill in the art will understand that there may be more than one isoform for each of atypical kinase C (aPKC), Par3, Par6, Cdc42, DE-Cadherin, Crumbs (Crb), Stardust (Sdt), PATj, Lin-7, beta-catenin, or Armadillo (Arm), and that any isoform of one of these proteins may be used in accordance with embodiments of the invention. Non-limiting examples of atypical kinase C (aPKC), Par3, Par6, Cdc42, DE-Cadherin, Crumbs (Crb), Stardust (Sdt), PATj, Lin-7, Armadillo (Arm) and beta-catenin isoform amino acid sequences are set forth as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 12, and SEQ ID NO: 13, respectively.

In some embodiments which comprise a label, the label comprises a marker which is a fluorophore. Non-limiting examples of fluorophores include fluorescent dyes, phosphorescent dyes, quantum dots, xanthene derivatives, cyanine derivatives, naphthalene derivatives, coumarin derivatives, oxadiaxol derivatives, pyrene derivatives, acridine derivatives, arylmethine derivatives, tetrapyrrole derivatives. Xanthene derivatives include but are not limited to fluorescein, rhodamine, Oregon green, eosin, Texas red, and Cal Fluor dyes. Cyanine derivatives include but are not limited to cyanine, indocarbocyanine, oxacarbocyanine, thiacarbocyanine, merocyanine, and Quasar dyes. Naphthalene derivatives include but are not limited to dansyl and prodan derivatives. Oxadiazole derivatives include but are not limited to pyridyloxazol, nitrobenzoxadiazole and benzoxadiazole. A non-limiting example of a pyrene derivative is cascade blue. Oxadine derivatives include but are not limited to Nile red, Nile blue, cresyl violet, and oxazine 170. Acridine derivatives include but are not limited to proflavin, acridine orange, and acridine yellow. Arylmethine derivatives include but are not limited to auramine, crystal violet, and malachite green. Tetrapyrrole derivatives include but are not limited to porphin, phtalocyanine and bilirubin.

In some embodiments which comprise a label and a fusion protein, the label may comprise a portion that binds to the fusion protein and a marker. For instance, the fusion protein may comprise an epitope tag to which the label binds, wherein the label comprises an antibody fragment that binds to the epitope tag. In one embodiment, the fusion protein comprises streptavidin, and the portion of the label which binds to the fusion protein is biotin.

In some embodiments, the label comprises a marker which is a reporter polypeptide.

In aspects of the invention which comprise a fusion protein or a label which comprises a reporter polypeptide, the reporter polypeptide may be an epitope tag, a fluorescent protein, a luminescent protein, a chromogenic enzyme, streptavidin, beta-galactosidase, or any other reporter polypeptide as defined herein.

Examples of epitope tags include but are not limited to V5-tag, Myc-tag, HA-tag, FLAG-tag, GST-tag, and His-tags. Additional examples of epitope tags are described in the following references: Huang and Honda, CED: a conformational epitope database. BMC Immunology 7:7 biomedcentral.com/1471-2172/7/7#B1. Retrieved Feb. 16, 2011 (2006); and Walker and Rapley, Molecular biomethods handbook. Pg. 467 (Humana Press, 2008). These references in their entireties are hereby incorporated by reference into this application. In some embodiments of the invention a label comprising an antibody or an antibody fragment is used to detect the localization and/or expression of a fusion protein which comprises an epitope tag.

Fluorescent proteins will be well known to one skilled in the art, and include but are not limited to GFP, AcGFP, EGFP, TagGFP, EBFP, EBFP2, Asurite, mCFP, mKeima-Red, Azami Green, YagYFP, YFP, Topaz, mCitrine, Kusabira Orange, mOrange, mKO, TagGFP, RFP, DsRed, DsRed2, mstrawberry, mRFP1, mCherry, and, mRaspberry. Examples of luminescent proteins include but are not limited to enzymes which may catalyze a reaction that emits light, such as luciferase. Examples of chromogenic enzymes include but are not limited to horseradish peroxidase and alkaline phosphatase.

General techniques and compositions for detecting and/or observing and/or analyzing labels and/or fusion proteins which are useful in the present invention are described in the following references: Tsien et al., Fluorophores for confocal microscopy. Handbook of biological confocal microscopy. New York: Plenum Press, 1995; Rietdorf, Mocroscopic techniques. Advances in Biochemical Engineering/Biotechnology. Berlin: Springer 2005; Lakowicz, J R, Principles of fluorescence spectroscopy ($3^{rd}$ ed.). Springer, 2006. These references in their entireties are hereby incorporated by reference into this application.

Injection of Compounds

Injected *D. melanogaster* embryos may be used to identify whether a compound is biologically active and/or a cancer drug candidate. In some embodiments, a compound that has biological activity perturbs the epithelium in a *D. melanogaster*. Unlabeled embryos or genetically modified embryos may be used. Use of a *D. melanogaster* embryo to test a compound for biological activity may comprise steps related to culturing *D. melanogaster*, embryo laying, embryo harvesting, embryo alignment, embryo injection, and embryo analysis to determine whether there is at least one difference between an embryo that has been injected with the compound and a embryo that has not been injected with the compound. General techniques useful for the culture and preparation of *Drosophila* include those described in the following references: Ashburner et al., *Drosophila. A laboratory handbook.* 1989, Cold Spring Harbor Laboratory Press, ISBN 0-87969-321-5, and Sullivan et al., ed., *Drosophila Protocols.* 2000, Cold Spring Harbor Laboratory Press, ISBN 978-087969586-6. These references in their entireties are hereby incorporated by reference into this application.

Fly Culture

In aspects of the invention which relate to fly culture and the injection of a compound into an embryo, at least one *D. melanogaster* adult female fly may be used to make a laying pot for embryo harvesting. The laying pot comprises a laying substrate plate. The *D. melanogaster* adult female fly may be 2-3 days old, 2-5 days old, or 2, 3, 4, or 5 days old. In some embodiments, it is necessary to wait until the *D. melanogaster* adult female fly has adapted to laying pot before collecting embryos. It may be necessary to wait at least 24 hours, or 24, 30, 36, 42, or 48 hours.

Embryo Laying

On the same day that at least one embryo is injected with a compound or compounds, the existing substrate plate is replaced with a new laying substrate plate in the laying pot, and the *D. melanogaster* adult female fly is given a period of time to lay retained, overdeveloped eggs. In some embodiments, the period of time given may be 1, 1.5, 2, 2.5, or 3 hours. The laying substrate plate containing overdeveloped eggs is then removed from the laying pot and incubated. The laying substrate plate may be incubated at a temperature of 20, 21, 22, 23, 24, 25, 26, 27, 28, 29, or 30° C. The laying substrate plate may be incubated for 45, 50, 55, 60, 65, 70, 75, 80, 85, or 90 minutes. In some embodiments, the laying substrate plate may be incubated for longer than 90 minutes.

Embryo Harvesting and Alignment

Some embodiments of the invention which encompass *D. melanogaster* embryo harvesting may comprise the steps of:
i) placing a basket strainer in a petri dish filled with 0.1% Tween-20/$H_2O$;
ii) harvesting the embryos from the laying substrate plate with a brush wet with 0.1% Tween-20/$H_2O$, and adding them to the basket strainer;
iii) replacing the 0.1% Tween-20/$H_2O$ from the petri dish, with a dechorionation agent to remove the chorions of the embryos;
iv) monitoring the dechorionation under a microscope;
v) replacing the dechorionation agent with $H_2O$;
vi) washing the embryos by replacing the $H_2O$ with new $H_2O$;
vii) drying the bottom of the basket;
viii) removing the embryos with a spatula;
ix) placing the embryos on a piece of agar;
x) aligning the embryos;
xi) preparing a slide with adhesive, and adhering the aligned embryos to the adhesive by inverting the slide over the embryos; and
xii) desiccating the embryos in a petri dish filled with silica gel.

Non-limiting examples of dechorionation agents which may be used in steps iii) and iv) are 25%, 30%, 35%, 40%, 45%, or 50% bleach in water. It will be understand that "$H_2O$" as used in steps i) to xii) hereinabove may include $H_2O$ that comprises salts and/or buffers. In some embodiments, step vi) may be repeated 1, 2, 3, 4, 5, or 6 times, or more. In some embodiments, in the embryos of step x) may be aligned with their posterior poles in the same direction.

Injection of Embryos

Some embodiments of the invention which relate to injecting a compound into a *D. melanogaster* embryo may comprise the steps of:
i) filling a needle with a solution comprising the compound;
ii) creating an opening at the tip of the needle;
iii) adjusting the drop size exiting the needle to a desired amount using a graticule; and
iv) injecting the embryo through the posterior pole.

The desired amount of step iii) may be 50 to 500 pL, or about 50, 100, 150, 200, 250, 300, 350, 400, 450, or 500 pL. In some embodiments the desired amount is 420 pL.

Analysis

In some embodiments in which the embryo is not labeled and does not express a fusion protein, differences in embryos injected with a compound compared to embryos not injected with the compound may be determined by light microscopy. If embryos which are labeled or that express a fusion protein are used, the label or fusion protein may be observed by appropriate methodologies including but not limited to fluorescent and confocal microscopy. After an embryo is injected with a compound, the embryo may be processed for analysis using standard procedures. Which procedure is performed will depend on the label used or the fusion protein expressed in the embryo. In some embodiments of the invention, the embryo is incubated, stained, or otherwise contacted with a label, such that the label becomes attached to a protein within the embryo, before analysis of the embryo is performed.

Embryos may be observed for development and death. The embryos may be observed for 1-12 h. In some embodiments, the embryos are observed for 1, 1.5, 2, 2.5, 3, 3.5, 4, 4.5, 5, 5.5, 6, 6.5, 7, 7.5, 8, 8.5, 9, 9.5, 10, 10.5, 11, 11.5, or 12 hours. In some embodiments, the death of an embryo after the embryo is injected with a compound may identify the compound as being a toxic compound.

Determining whether there is a difference between an embryo which has been injected with a compound and an embryo which has not been injected with the compound may be performed at any time point or time points occurring from the moment of injection of the compound until the embryo has developed into an adult fly. A time point may be a point of time as counted from a beginning reference point in time such as from the approximate moment of egg laying or the approximate moment of injection, or from any *D. melanogaster* developmental stage.

Soaking of Egg Chambers

Aspects of the invention relate to the use of a dissected *D. melanogaster* egg chamber to test a compound for biological activity, or to determine whether a compound is a cancer drug candidate. In some embodiments, a compound that has biological activity perturbs the epithelium in a *D. melanogaster*. Dissected egg chambers from wild-type *D. melanogaster* or from a genetically modified *D. melanogaster* may be used. In some embodiments of the invention the *D. melanogaster* may be genetically modified to express a fusion protein comprising amino acids in the sequence of the amino acid sequence of a protein which is naturally expressed in *D. melanogaster*, and a reporter polypeptide. In some embodiments, a label is used to detect the expression and/or localization of a protein in an egg chamber.

Processes of the invention which use a *D. melanogaster* egg chamber to test a compound for biological activity or to determine whether a compound is a cancer drug candidate may comprise steps related to culturing *D. melanogaster*, preparing *D. melanogaster*, dissection of an egg chamber or egg chambers from at least one *D. melanogaster* adult female fly, contacting the egg chamber or egg chambers with the compound, preparing the egg chamber for analysis, and analyzing the egg chamber for at least one difference between an egg chamber that has been contacted with the compound and a corresponding egg chamber that has not been contacted with the egg chamber. General techniques useful for the culture and preparation of *D. melanogaster* include those described in the following references: Ashburner et al., *Drosophila. A laboratory handbook*. 1989, Cold Spring Harbor Laboratory Press, ISBN 0-87969-321-5, and Sullivan et al., ed., *Drosophila Protocols*. 2000, Cold Spring Harbor Laboratory Press, ISBN 978-087969586-6. These references in their entireties are hereby incorporated by reference into this application.

Fly Culture

In some embodiments of the invention which relate to fly culture and the soaking of an egg chamber with a compound, at least one *D. melanogaster* adult female fly is incubated with at least one *D. melanogaster* adult male fly. In some embodiments, the *D. melanogaster* adult female fly may be 1 to 3 days old. In some embodiments, the *D. melanogaster* adult female fly is 1, 1.5, 2, 2.5, or 3 days old. In some embodiments, the *D. melanogaster* adult female fly may be incubated with at least one *D. melanogaster* adult male fly for 1 to 2 days. In some embodiments, the *D. melanogaster* adult female fly is incubated with at least one *D. melanogaster* adult male fly for 1, 1.5, or 2 days. In some embodiments, at least one *D. melanogaster* adult female fly is incubated with at least one *D. melanogaster* adult male fly in a bottle or vial containing *D. melanogaster* food and yeast ad libitum.

Fly Preparation

Some embodiments of the invention which relate to *D. melanogaster* adult female fly preparation may comprise the steps of:
1) selecting at least one *D. melanogaster* adult female fly on a $CO_2$ pad or after incubation of the *D. melanogaster* adult female fly at a temperature that is sufficiently reduced to immobilize the *D. melanogaster* adult female fly;
ii) decapitating the *D. melanogaster* adult female fly; and
iii) transferring the *D. melanogaster* adult female fly to a dish which is cooled until the *D. melanogaster* a adult female fly is dissected.

In some embodiments, the dish of step iii) is cooled to a temperature at 4° C. or less.

In some embodiments, the number of female flies selected is a number that is suitable for the number of compounds. In some embodiments, 10 to 30 female flies are selected for each compound. In some embodiments about 20 female flies are selected for each compound. In some embodiments, about 5, 10, 15, 20, 25, 30, 35, 40, 45, or 50 female flies are selected for each compound. In some embodiments about 200, 400, 600, 800, or 1000 female flies are selected for about 5, 10, 15, 20, 25, 30, 35, 40, 45, or 50 compounds.

Dissection

In some embodiments of the invention which encompass *D. melanogaster* adult female fly dissection may comprise the steps of:
i) removing the ovaries of at least one *D. melanogaster* adult female fly for each compound;
ii) placing the ovaries into growth medium; and
iii) separating the ovarioles.

In some embodiments, the ovaries of 1-10 *D. melanogaster* adult female flies are removed. In some embodiments, the ovaries of 1, 2, 3, 4, 5, 6, 7, 8, 9, or 10 *D. melanogaster* adult female flies are removed.

The ovaries may be placed into 100-200 µL of growth medium, or about 100, 125, 150, 175, or 200 µL of growth medium. Examples of growth media which are suitable for use in embodiments of the invention include but are not limited to Shields and Sang M3 insect medium, Schneider's medium, Robb's medium (Theurkauf, W E, Chapter 25, Methods in Cell Biology Volume 44 (1994) Lawrence S. B. Goldstein and Eric A. Fyrberg, ISBN 978-0-12-564145-6) and others, all of which may or may not be supplemented with any combination of fetal bovine serum, albumin and/or other supplements. In some embodiments, the growth medium is not supplemented with fetal bovine serum. In some embodiments, the growth medium is not supplemented with a serum free supplement. In some embodiments, the growth medium is not supplemented with a growth factor. In some embodiments, the growth medium is not supplemented with a hormone. In some embodiments, the growth medium is supplemented with fetal bovine serum or a serum free supplement or a growth factor or a hormone, or any combination thereof.

The ovarioles are processed to remove the impact of muscle sheath contraction during analysis.

Some embodiments of the invention which encompass *D. melanogaster* adult female fly dissection may comprise the steps of:

i) Transferring flies to an electric liquefier filled with up to 250 mL of dissection medium. In some embodiments, the electric liquefier is filled with about 100 to about 500 mL of dissection medium. In some embodiments, the electric liquefier is filled with about 100, 150, 200, 250, 300, 350, 400, 450, or 500 mL of dissection medium. Suitable dissection mediums include but are not limited to Shields and Sang M3 insect medium, Schneider's medium, Robb's medium (Theurkauf, W E, Chapter 25, Methods in Cell Biology Volume 44 (1994) Lawrence S. B. Goldstein and Eric A. Fyrberg, ISBN 978-0-12-564145-6) and others, all of which may or may not be supplemented with any combination of fetal bovine serum, albumin and/or other supplements. In some embodiments, the growth medium is not supplemented with fetal bovine serum. In some embodiments, the growth medium is not supplemented with a serum free supplement. In some embodiments, the growth medium is not supplemented with a growth factor. In some embodiments, the growth medium is not supplemented with a hormone. In some embodiments, the growth medium is supplemented with fetal bovine serum or a serum free supplement or a growth factor or a hormone, or any combination thereof;

ii) Isolating egg chambers by fly maceration in the electric liquefier. In some embodiments, the egg chambers are isolated by fly maceration in the electric liquefier with 1, 2, 3, 4, or 5 second pulses repeated 1, 2, 3, 4, or 5 times in low speed. In some embodiments, the egg chambers are isolated by fly maceration in the electric liquefier with 2 second pulses repeated 3 times in low speed;

iii) Filtrating the fly homogenate through a mesh placed over a cup. Isolated egg chambers pass through the mesh and unopened flies and debris are retained in the mesh. In some embodiments, the cup is a glass cup. The mesh may be made of steel, nylon, popypropylene or other suitable materials, used alone or in combination. On some embodiments, the pore size of the mesh is 200 to 500 µm. In some embodiments, the pore size of the mesh is about 200, 250, 300, 350, 400, 450 or 500 µm. In some embodiments, the a pore size of the mesh is 250 µm;

iv) Repeating the maceration process with unopened flies retained in the mesh using the dissection medium;

v) Pooling the egg chambers by repeating filtration using a new/clean mesh;

vi) Leaving the egg chambers to settle and removing the dissection medium. In some embodiments, the egg chambers are left to settle for 1 to 10 minutes. In some embodiments, the egg chambers are left to settle for about 1, 2, 3, 4, 5, 6, 7, 8, 9, or 10 minutes. In some embodiments, the egg chambers are left to settle for 5 minutes. In some embodiments, the dissection medium is removed by decanting or aspirating with a manual pipette or a vacuum pump;

vii) A residual volume is left and egg chambers are transferred to tubes. In some embodiments, the residual volume is from 50 to 150 mL. In some embodiments, the residual volume is about 50, 100, or 150 mL. In some embodiments, the residual volume is 100 mL. In some embodiments, the tubes are conical tubes; and viii) Enriching the egg chambers through serial rinsing steps:
   a) Leaving egg chambers to settle and aspirating the dissection medium until a residual volume is left. In some embodiments, the egg chambers are left to settle for 1 to 10 minutes. In some embodiments, the egg chambers are left to settle for about 1, 2, 3, 4, 5, 6, 7, 8, 9, or 10 minutes. In some embodiments, the egg chambers are left to settle for 5 minutes. In some embodiments, the dissection medium is aspirated until 1 mL to 10 mL residual volume is left. In some embodiments, the dissection medium is aspirated until about 1, 2, 3, 4, 5, 6, 7, 8, 9, or 10 mL residual volume is left. In some embodiments, the dissection medium is aspirated until 5 mL residual volume is left;
   b) Rinsing the egg chambers by adding up to 10 to 20 mL of dissection medium to the tubes. In some embodiments, about 11, 12, 13, 14, 15, 16, 17, 18, 19 or 20 mL of dissection medium is added to the tubes;
   c) Leaving the egg chambers to settle, and aspirating the dissection medium is aspirated until an amount of dissection medium is left. In some embodiments, the egg chambers are left to settle for 1 to 10 minutes. In some embodiments, the egg chambers are left to settle for about 1, 2, 3, 4, 5, 6, 7, 8, 9, or 10 minutes. In some embodiments, the egg chambers are left to settle for 5 minutes. In some embodiments, the dissection medium is aspirated until 1 mL to 10 mL is left. In some embodiments, the dissection medium is aspirated until about 1, 2, 3, 4, 5, 6, 7, 8, 9, or 10 mL is left. In some embodiments, the dissection medium is aspirated until 1 mL is left; and
   d) Adding clean dissection medium to the tubes and rapidly transferring the egg chambers to a tray.

Compound Treatment

In some embodiments of the invention which relate to contacting dissected egg chambers with a compound, dissected egg chambers may be transferred to a tube after dissection. In some embodiments, the growth media containing the egg chamber may be replaced to remove dissection detritus. In some embodiments, the egg chambers are contacted with a compound while still within an ovariole, in some embodiments, the egg chambers are removed from the ovarioles and then contacted with a compound. A compound may be added to the growth media in which the egg chamber is already soaked, or may be added in new growth media which replaces the growth media which does not contain the compound. In some embodiments, the egg chamber is soaked in less than 200 µL of incubation medium. In some embodiments, the egg chamber is soaked in more than 200 µL of incubation medium. In some embodiments, the egg chamber is soaked in 200, 225, 250, 275, or 300 µL of incubation medium. The egg chamber may be soaked in growth medium which contains the compound at a temperature of 20, 21, 22, 23, 24, 25, 26, 27, 28, 29, or 30° C. In preferred embodiments, the egg chamber is soaked in incubation medium at a temperature of 25° C. The egg chamber may be soaked in incubation medium for a period lasting from 90 minutes to 6 hours or for a period of about 0.5, 1, 1.5, 2.5, 3, 3.5, 4, 4.5, 5, 5.5, or 6 hours.

After an egg chamber is contacted with a compound, the egg chamber may be fixed, using chemical treatments such as paraformaldehyde, methanol, or others. Alternatively, the egg chamber may be analyzed, or processed for analysis directly, without being fixed.

In some embodiments of the invention which relate to contacting dissected egg chambers with a compound, dissected egg chambers may be transferred to several wells of a microwell plate after dissection. For example, 100-200 µL of the egg chamber/dissection medium mixture may be transferred to wells of a microwell plate. The microwell plate may have 48, 96, 384 wells or more and may or may not have an optical bottom and black, white or transparent walls. After transfer to a microwell plate, the dissection medium may be aspirated, leaving a controlled volume. In some embodiments, the controlled volume is 50 to 250 µL. In some embodiments, the controlled volume is about 50, 100, 150, 200, or 250 µL. In some embodiments, the controlled volume is 100 µL. The drug, appropriately diluted in suitable growth medium may then be added to the microwell containing the egg chambers. In some embodiments, a volume of 50-500 µL of the drug appropriately diluted in suitable growth medium is added. In some embodiments, a volume of about 50, 100, 150, 200, 250, 300, 400, or 500 µL of the drug appropriately diluted in suitable growth medium is added. In some embodiments, a volume of about 100 µL of the drug appropriately diluted in suitable growth medium is added. Non-limiting examples of suitable growth mediums are Shields and Sang M3 insect medium, Schneider's medium and others, all of which may or may not be supplemented with any combination of fetal bovine serum, serum free supplements, insulin and/or other supplements. The egg chambers may then be incubated at 20-30° C., or about 20, 21, 22, 23, 24, 25, 26, 27, 28, 29, or 30° C. In some embodiments, the egg chambers are incubated at 25° C. In some embodiments, incubation times may range from 1 h to 6 h. In some embodiments, the incubation time is for a period of about 0.5, 1, 1.5, 2.5, 3, 3.5, 4, 4.5, 5, 5.5, or 6 hours. After an egg chamber is contacted with a compound, the egg chamber may be fixed, using chemical treatments such as paraformaldehyde, methanol, or others. Alternatively, the egg chamber may be analyzed, or processed for analysis directly, without being fixed. The egg chambers may be kept in the microwell plate with or without standard mountants and anti-fading products.

Some embodiments of the invention relate to contacting the egg chamber with multiple compounds at once. Therefore, the incubation medium may contain multiple compounds which are being tested for biological activity simultaneously. The use of incubation medium which contains more than one compound allows for higher throughput processes of preparing information that identifies a compound as a cancer drug candidate. In embodiments in which an egg chamber is contacted with more than one compound, and where there is a difference between the egg chamber which is contacted with more than one compound and an egg chamber not contacted with the compounds, it is necessary to subsequently test each of the compounds separately. Thus, the invention provides processes for first testing multiple compounds at once, and if a positive result is obtained in the first test, to then perform subsequent tests which evaluate each of the compounds that were tested together in the first test individually to determine which compound or compounds has biological activity or is a cancer drug candidate. In some embodiments, 2, 3, 4, 5, 6, 7, 8, 9, or 10 compounds may be tested at once in the first test.

Analysis

After an egg chamber is contacted with a compound, the egg chamber may be processed for analysis. In some embodiments, an egg chamber that has been contacted with a compound is analyzed on a slide. The egg chamber may be transferred to a slide in incubation medium. Alternatively, the incubation medium may be replaced with growth medium, so that the egg chamber is transferred to a slide in growth medium. In some embodiments, the egg chamber may be mounted in a manner suitable for observation. In some cases, egg chambers are immersed in mounting media which may or may not polymerize and may or may not contain chemical agents to reduce signal fading.

Egg chambers may be contacted with a compound at developmental stages 1 to 11 as defined in the field, e.g. in Sullivan et al., ed. *Drosophila* Protocols. 2000; Cold Spring Harbor Laboratory Press, ISBN 978-087969586-6; Horne-Badovinac and Bilder, 2005; and Baston and St Johnston, 2008, the contents of each of which are hereby incorporated by reference. Egg chambers may be contacted with a compound at stage 1, 2, 3, 4, 5, 6, 7, 8, 9, 10, or 11, or any combination thereof. Additionally, determining whether there is a difference between an egg chamber contacted with a compound, and an egg chamber not contacted with a compound may be conducted at any stage that is concurrent with, or that follows a stage in which the egg chamber is contacted with the compound.

A suitable microscope set-up may be used to score egg chambers for having healthy nurse cells or oocytes, and for differences between an egg chamber contacted with a compound and an egg chamber not contacted with the compound. In embodiments which comprise a fluorescent, phosphorescent, or otherwise luminescent label or fusion protein, microscopy may be used to determine the quantity, quality, and/or distribution of label or fusion protein in egg chambers. In some embodiments, digital images of egg chambers may be recorded. In some embodiments, digital images are recorded either by the operator or automatically using a suitable microscope and software. In some embodiments of the invention, the egg chamber is incubated, stained, or otherwise contacted with a label, such that the label becomes attached to a particular protein within the egg chamber, before analysis of the egg chamber is performed. In some embodiments, egg chambers are scored for having healthy germ cells and fluorescence quantity, quality and distribution in the apical part of the follicular epithelium using a suitable microscope set-up. Where other labeling systems are used, suitable experimental steps may be used.

In some embodiments, a positive compound is identified where healthy egg chambers have altered signal quality, quantity or distribution.

In some embodiments, identification can be made by the operator or using a suitable/tailor-made software of analysis. In some embodiments, a compound is identified to have biological activity when an egg chamber contacted with the compound has increased cell death and/or altered label or fusion protein signal quality, quantity, or distribution, compared to an egg chamber not contacted with the compound. In some embodiments, a compound is identified to be a cancer drug candidate when an egg chamber contacted with the compound does not have increased cell death, but has altered label or fusion protein signal quality, quantity, or distribution, compared to an egg chamber not contacted with the compound.

Compositions

According to another aspect of the invention, there is provided the use of a cancer drug candidate in the manufacture of a medicament for the treatment of cancer, where the medicament is formulated to deliver a dosage of the cancer drug candidate to a subject.

General techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences Vol. 40 (Gilbert S. Banker, Christopher T. Rhodes, Eds.). The references in their entireties are hereby incorporated by reference into this application.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1

Manual Soaking of Egg Chambers

Fly Culture 1-3 day-old female flies which express a fusion protein comprising Par6 fused at the C-terminus to AcGFP (Par6-AcGFP; SEQ ID NO: 11) under the control of the endogenous Par6 promoter were incubated with males for 1-2 days in bottles or vials containing fly food and yeast ad libitum. The nucleic acid sequence of Par6-AcGFP, including all "natural" control elements, is set forth as SEQ ID NO: 10.

Fly Preparation

Females were selected using a $CO_2$ pad, and then sacrificed by decapitation. Decapitated flies were then transferred to a dish which was kept on ice until dissection.

Dissection

The ovaries of 1-10 flies were removed for each treatment and kept in 100-200 µL growth medium. Ovarioles were carefully separated and prepared for drug treatment.

Drug Treatment

The egg-chambers were transferred to a tube and their medium, which contained dissection detritus, was removed. At least 200 µL of new growth medium containing a compound to be tested was then added for 90 minutes to 6 h. Egg chambers were then processed for analysis directly.

Mounting for Microscope Analysis

Egg chambers were mounted onto a microscope slide for observation.

Result Analysis

Suitable egg chambers (stage 7) were scored for having healthy germ cells as well as for the intensity and distribution of Par6-AcGFP in the apical part of the follicular epithelium using fluorescence microscopy. Digital images of the egg chambers were recorded.

Egg chambers that were treated with compounds and that had altered GFP signal quantity and/or distribution compared to untreated egg chambers, are those that identified the compounds with which they were contacted as being cancer drug candidates.

Example 2

Medium Scale Soaking of Egg Chambers

Purpose

Extension of the soaking of egg chambers protocol to a semi-automated format for medium scale of compound analysis.

Compounds may be routinely analyzed with medium scale soaking of egg chambers and then confirmed by low scale/manual format.

As for the low scale soaking protocol exemplified in Example 1, the medium scale soaking protocol consists of fly culture, fly preparation, dissection, drug treatment, label processing, preparation for analysis and analysis. Standard culture and preparation methods are used as described in many sources, including Theurkauf, W E, Chapter 25, Methods in Cell Biology Volume 44 (1994) Lawrence S. B. Goldstein and Eric A. Fyrberg, ISBN 978-0-12-564145-6; Ashburner, M. et al, *Drosophila*. A laboratory handbook. (1989), Cold Spring Harbor Laboratory Press ISBN, 0-87969-321-5 and W. Sullivan, et al., ed., *Drosophila* Protocols. (2000) Cold Spring Harbor Laboratory Press, ISBN 978-087969586-6, the entire contents of each of which are hereby incorporated herein by reference.

Fly Culture 1-3 day-old females are incubated with males for 1 to 2 days in bottles/vials containing fly food and yeast ad libitum.

Fly Preparation

A number of female flies suitable for the number of compounds is selected to analyze in the $CO_2$ pad. In one non-limiting example, 800 female flies are selected for 40 compounds.

Dissection

Flies are transferred to an electric liquefier filled with up to 250 mL of dissection medium. Suitable dissection mediums include Shields and Sang M3 insect medium, Schneider's medium, Robb's medium (Theurkauf, W E, Chapter 25, Methods in Cell Biology Volume 44 (1994) Lawrence S. B. Goldstein and Eric A. Fyrberg, ISBN 978-0-12-564145-6) and others, all of which may or may not be supplemented with any combination of fetal bovine serum, albumin and/or other supplements;

Egg chambers are isolated by fly maceration in the electric liquefier with 2 second pulses repeated 3 times at low speed;

The fly homogenate is filtrated through a mesh placed over a glass cup. Isolated egg chambers pass through the mesh and unopened flies and debris are retained in the mesh. The mesh can be made of steel, nylon, popypylene or other suitable materials, used alone or in combination, with a pore size of 250 µm;

The maceration process is repeated with unopened flies retained in the mesh using the dissection medium;

Egg chambers are pooled by repeating filtration using a new/clean mesh;

Egg chambers are left to settle for 5 minutes and dissection medium is removed by decanting or aspirating with a manual pipette or a vacuum pump;

A 100 mL residual volume is left and egg chambers are transferred to conical tubes; and Egg chambers are enriched through serial rinsing steps:

Egg chambers are left to settle for 5 minutes and dissection medium aspirated until 5 mL residual volume is left;

Egg chambers are rinsed by adding up to 10-20 mL of dissection medium to the conical tubes;

Egg chambers are left to settle for 5 minutes, and dissection medium is aspirated until 1 mL is left; and Clean dissection medium is added to the tubes and egg chambers are rapidly transferred to a tray.

Drug Treatment 100-200 μL of the egg chamber/dissection medium mixture is transferred to several wells of a microwell plate. The microwell plate can have 48, 96, 384 wells or more and may or may not have an optical bottom and black, white or transparent walls;

The dissection medium is aspirated, leaving a controlled volume of 100 μL;

100 μL of the drug appropriately diluted in suitable growth medium is added. Suitable growth medium include Shields and Sang M3 insect medium, Schneider's medium and others, all of which may or may not be supplemented with any combination of fetal bovine serum, serum free supplements, insulin and/or other supplements;

The egg chambers are incubated at 25° C. Incubation times can range from 1 h to 6 h; and Egg chambers may be fixed, using chemical treatments such as paraformaldehyde, methanol or others, or processed directly.

Label Processing

Where required, egg chambers are processed using standard procedures to detect the signal in the labeling method used.

Preparation for Analysis

Egg chambers are kept in the microwell with or without standard mountants and anti-fading products.

Result Analysis

Suitable egg chambers (stage 1 to 11, staged as is the convention in the field, e.g. W. Sullivan, et al., ed., *Drosophila* Protocols. (2000) Cold Spring Harbor Laboratory Press, ISBN 978-087969586-6) are scored for having healthy germ cells and fluorescence quantity, quality and distribution in the apical part of the follicular epithelium using a suitable microscope set-up. Where other labeling systems are used, suitable experimental steps are used.

Digital images are recorded either by the operator or automatically using a suitable microscope and software.

A positive compound is identified where healthy egg chambers have altered signal quality, quantity or distribution. Identification can be made by the operator or using a suitable/tailor-made software of analysis.

Example 3

Injection of Embryos

Fly Preparation 2-3 day-old flies which express Par6-AcGFP under the control of the endogenous Par6 promoter and an apple juice/agar substrate plate are used to prepare pots for egg laying. Flies are allowed to adapt to the pots for a minimum of 24 h.

Embryo Laying

On the day of the experiment, the first apple juice/agar substrate plate is replaced with a second apple juice/agar substrate plate. After 1 h the second apple juice/agar substrate plate is replaced with another apple juice/agar substrate plate which is used to collect additional embryos. Apple juice/agar substrate plates are continuously replaced as more embryos were collected each hour until the desired number of embryos are collected. Once an apple juice/agar substrate plate containing embryos is removed, it is incubated at 25° C. for 50-60 minutes.

Embryo Harvesting and Alignment

A basket strainer is placed in a petri dish which is contains 0.1% Tween-2/$H_2O$. Each embryo is then harvested from the apple juice/agar plate with a paint brush that is wet with 0.1% Tween-20/$H_2O$ and then added to the basket. The 0.1% Tween-20/$H_2O$ in the petri dish is then discarded and replaced with 50% bleach in $H_2O$ to remove the chorions of embryos in the basket. The embryos are incubated in the 50% bleach solution for about 1.5 minutes, after which they are washed by replacing the 50% bleach solution with $H_2O$. The $H_2O$ is replaced with new $H_2O$ at least 4 times to wash the embryos. The basket strainer is then removed from the petri dish, and the bottom of the basket is dried with paper to facilitate removal of the embryos with a spatula. The embryos are then placed on a small piece of agar and about 50 embryos are aligned with their posterior poles pointing in the same direction. A slide is prepared with tape and aligned over the embryos so that they stick to the tape. The embryos are then desiccated for 4 minutes at 25° C. in a petri dish which has been filled with silica gel.

Injection of Embryos

A needle that comes to a closed point at its tip is filled with a solution comprising a compound to be tested for biological activity, and the tip of the needle is broken to provide an opening through which the solution may be injected. The drop size of the solution which exits the needle during each injection is adjusted with a graticle in order to be about 420 pL of solution. The embryos are then injected through their posterior poles.

Analysis

Development of the treated embryos is followed for up to 4 h, and they are scored for developmental differences, cellularization differences and altered amounts of cell death compared to untreated embryos. The AcGFP signal in the embryos is traced for location and intensity.

Results

Embryos that are treated with compounds and that have altered GFP signal quantity and/or distribution compared to untreated embryos are those that identify the compounds with which they were injected as being cancer drug candidates.

Example 4

Cancer Drug Candidate Validation

Compounds that are identified as cancer drug candidates using processes of the invention are evaluated for efficacy in appropriate mammalian models. Compounds identified as cancer drug candidates using the process described in Example 1, 2, or 3 are administered to groups of mice, which each have a carcinoma. Mice are treated with the drug candidates until they are sacrificed for analysis or die from the carcinoma. A proportion of the cancer drug candidates which are tested in vivo are found to effectively inhibit tumor growth in the mice. Furthermore, a proportion of the cancer drug candidates are found to effectively inhibit cancer cell survival in the Additionally, a proportion of the cancer drug candidates are found to effectively inhibit cancer metastasis in the mice.

When cancer drug candidates identified using the process described in Example 1, 2, or 3 are compared to cancer drug candidates identified using in vitro processes, the proportion of the cancer drug candidates which are effective at inhibiting tumor growth while being well tolerated in mice is greater for those identified using the process described in Example 1, 2, or 3 than those identified using an analogous in vitro screening process. Additionally, the proportion of the cancer drug candidates which are effective at killing cancer cells while being well tolerated in mice is greater for those identified using the process in Example 1, 2, or 3 than those identified using an analogous in vitro screening process. Furthermore, the proportion of the cancer drug candidates which are effective at reducing the metastasis cancer cells while being well tolerated in mice is greater for those identified using the process in Example 1, 2, or 3, than those identified using an analogous in vitro screening process.

When cancer drug candidates identified using the process described in Example 1, 2, and 3 are compared to cancer drug candidates identified using an analogous in vivo process which uses a *D. melanogaster* which was genetically modified to have the reduced or increased function of a protein ("traditional *Drosophila* screening process"), the proportion of the cancer drug candidates which are effective at inhibiting tumor growth while being well tolerated in mice is greater for those identified using the process described in Example 1, 2, and 3 than those identified using an analogous traditional *Drosophila* screening process. Additionally, the proportion of the cancer drug candidates which are effective at killing cancer cells while being well tolerated in mice is greater for those identified using the process in Example 1, 2, or 3 than those identified using an analogous traditional *Drosophila* screening process. Furthermore, the proportion of the cancer drug candidates which are effective at reducing the metastasis cancer cells while being well tolerated in mice is greater for those identified using the process in Example 1, 2, or 3, than those identified using an analogous traditional *Drosophila* screening process.

Discussion

The invention provides screening processes that identify cancer drug candidates with lower background effects and higher reliability than other *D. melanogaster*-based screening processes. One advantageous aspect of the subject invention is that the *D. melanogaster* embryos and egg chambers of the invention are minimally genetically modified. The *D. melanogaster* embryos and egg chambers of the invention are wild-type with the exception that they may express a reporter polypeptide fused to an endogenous protein. Aspects of the invention do not rely on mutants or flies that are modified to have the significant gain or loss of function of any gene, and therefore their cells behave normally. The approaches disclosed herein allow for cleaner, more reliable cancer drug candidate identification than other *D. melanogaster*-based screens.

The *D. melanogaster* Egg Chamber

Oogenesis requires many cellular processes, including cell cycle control, cell fate specification, cell polarization, and epithelial morphogenesis (Bastock and St Johnston, 2008). The *Drosophila* egg chamber comprises both germ and somatic cells which signal to each other and undergo profound cellular changes throughout oogenesis. Many of the morphological changes observed during oogenesis occur in the follicular epithelium, the portion of the egg chamber which produces yolk and eggshell components of the egg, and which also signals to the germ cells to help determine future embryonic axes (Horne-Badovinac and Bilder, 2005). Surprisingly, as disclosed herein, a compound's effects on cellular processes observed within the *D. melanogaster* egg chamber are a reliable predictor of the compound's ability to perturb cancer cell proliferation, metastasis, and survival in mammals.

Par6

Par6 regulates cell polarity and fate determination during egg chamber and embryonic development in *D. melanogaster* (Petronczki and Knoblich, 2000). As a PB1 domain protein that links aPKCs to Rac1, Par6 has been suggested to play a role in oncogenic PKCι signaling (Fields et al. 2007; Brumby and Richardson, 2005). Fields et al. 2007 purported to describe in vitro screens for compounds which disrupt the interaction of the PB1-PB1 domain interaction between PKCι and Par6, however, Fields et al. did not teach or suggest conducting in vivo drug screens which employed Par6 in any capacity, in *D. melanogaster* or otherwise. Furthermore, aspects of the subject invention relate to the identification of cancer drug candidates that alter Par6 function or expression in cells that behave normally within an in vivo context. Surprisingly, the ability of a compound to directly or indirectly alter the normal expression and/or function of Par6, or the behavior of cells that express Par6 within the epithelium of an almost completely wild-type *D. melanogaster* embryo or egg chamber identifies that compound as a cancer drug candidate.

REFERENCES

1. Bastock and St. Johnston, *Drosophila* oogenesis. Current Biology, 2008, 18(23):1082-1087.
2. Bier E., *Drosophila*, the golden bug, emerges as a tool for human genetics, Nature Reviews Genetics (1 Jan. 2005) 6, 9-23.
3. Brumby and Richardson, Using *Drosophila melanogaster* to Map Human Cancer Pathways. Nature Reviews, 2005, 5:326-639.
4. Fields et al., Targeting the oncogenic protein kinase Cι signaling pathway for the treatment of cancer. Biochemical Society Transactions, 2007, 35:996-1000.
5. Horne-Badovinac and Bilder, Mass Transit: Epithelial Morphogenesis in the *Drosophila* Egg Chamber. Developmental Dynamics, 2005, 232:559-574.
6. Keserü and Makara, Hit discovery and hit-to-lead approaches. Drug Discovery Today, 2006, 11: 741-748.
7. Petronczki and Knoblich, DmPar-6 directs epithelial polarity and asymmetric cell division of neuroblasts in *Drosophila*. Nature Cell Biology, 2001, 3:43-49.
8. Wirtz-Peitz et al., Linking Cell cycle to Asymmetric Division: Aurora-A Phosphorylates the Par complex to Regulate Numb Localization. Cell, 2008, 135:161-173.

What is claimed is:

1. A process for identifying whether a compound is an epithelial cancer drug candidate comprising:
   i) obtaining, by dissection from at least one *D. melanogaster* adult female fly, at least one *D. melanogaster* egg chamber which is genetically unmodified except that the at least one *D. melanogaster* egg chamber comprises at least one nucleotide sequence encoding a Par6 fusion protein under control of the Par6 endogenous promoter, wherein the Par6 fusion protein comprises a reporter polypeptide fused to Par6, and wherein the nucleic acid sequence that encodes the Par6 fusion protein and the Par6 endogenous promoter is SEQ ID NO: 10;
   ii) contacting the at least one dissected egg chamber with the compound by soaking it in an incubation medium containing the compound; and
   iii) comparing the level of expression of the Par6 fusion protein in the apical part of the follicular epithelium of the at least one dissected egg chamber contacted with the compound, to the level in the apical part of the follicular epithelium of a corresponding at least one dissected egg chamber not contacted with the compound,
   wherein the presence of a difference in the expression of the Par6 fusion protein in the apical part of the follicular epithelium of the at least one dissected egg chamber contacted with the compound compared to the apical part of the follicular epithelium of a corresponding at least one dissected egg chamber not contacted with the compound identifies the compound as an epithelial cancer drug candidate.

2. The process of claim 1, wherein the difference in the expression of the Par6 fusion protein in the apical part of the follicular epithelium of the at least one dissected egg chamber contacted with the compound compared to the apical part of the follicular epithelium of the corresponding at least one dissected egg chamber not contacted with the compound comprises increased or decreased expression.

3. The process of claim 1, wherein the difference in the expression of the Par6 fusion protein in the apical part the follicular epithelium of the at least one dissected egg chamber contacted with the compound compared to the apical part of the follicular epithelium of the corresponding at least one dissected egg chamber not contacted with the compound comprises a different localization of the Par6 fusion protein within follicle epithelial cells.

4. The process of claim 3, wherein there is proportionally less localization of the Par6 fusion protein at the apical side of the follicle epithelial cells of the at least one dissected egg chamber contacted with the compound compared to the follicle epithelial cells of the corresponding at least one dissected egg chamber not contacted with the compound.

5. The process of claim 1, wherein difference in the expression of the Par6 fusion protein in the apical part of the follicular epithelium of the at least one dissected egg chamber contacted with the compound compared to the apical part of the follicular epithelium of the corresponding at least one dissected egg chamber not contacted with the compound comprises a different location of protein production or post-transcriptional modification of the Par6 fusion protein.

6. A process for identifying whether a compound is an epithelial cancer drug candidate comprising:
   (a) i) obtaining, by dissection from at least one *D. melanogaster* adult female fly, at least one *D. melanogaster* egg chamber which is genetically unmodified except that the at least one *D. melanogaster* egg chamber comprises at least one nucleotide sequence encoding a Par6 fusion protein under control of the Par6 endogenous promoter, wherein the Par6 fusion protein comprises a reporter polypeptide fused to Par6, wherein the nucleic acid sequence that encodes the Par6 fusion protein and the Par6 endogenous promoter is SEQ ID NO: 10;
   ii) contacting the at least one dissected egg chamber with the compound, and up to four additional compounds by soaking it in an incubation medium containing the compounds;
   iii) comparing the level of expression of the reporter polypeptide in the apical part of the follicular epithelium of the at least one dissected egg chamber contacted with the compound and up to four additional compounds, to the level in the apical part of the follicular epithelium of a corresponding at least one dissected egg chamber not contacted with the compound and up to four additional compounds;
   iv) if there is a difference in the expression of the reporter polypeptide in the apical part of the follicular epithelium of the at least one dissected egg chamber contacted with the compound and up to four additional compounds compared to the apical part of the follicular epithelium of the corresponding at least one dissected egg chamber not contacted with the compound, contacting at least one additional dissected egg chamber according to step i) with the compound but not the additional compound or compounds of step ii) and step iii); and v) determining whether there is a difference in the expression of the reporter polypeptide in the apical part of the follicular epithelium of the at least one additional dissected egg chamber of step iv) and the apical part of the follicular epithelium of a corresponding at least one additional dissected egg chamber not contacted with the compound, wherein the presence of a difference in the expression of the reporter polypeptide in the apical part of the follicular epithelium of the at least one additional dissected egg chamber of iv) compared to the apical part of the follicular epithelium of the corresponding at least one additional dissected egg chamber not contacted with the compound identifies the compound as an epithelial cancer drug candidate; or (b) i) obtaining, by dissection from at least one *D. melanogaster* adult female fly, at least one *D. melanogaster* egg chamber which is genetically unmodified except that the at least one *D. melanogaster* egg chamber optionally comprises at least one nucleotide sequence encoding a Par6 fusion protein under control of the Par6 endo endogenous promoter, wherein the Par6 fusion protein comprises a reporter polypeptide fused to Par6, wherein the nucleic acid sequence that encodes the Par6 fusion protein and the Par6 endogenous promoter is SEQ ID NO: 10;

ii) contacting the at least one dissected egg chamber with the compound by soaking it in an incubation medium containing the compound;

iii) comparing the level of expression of the reporter polypeptide in the apical part of the follicular epithelium of the at least one dissected egg chamber contacted with the compound, to the level in the apical part of the follicular epithelium of a corresponding at least one dissected egg chamber not contacted with the compound; and iv) observing whether there is substantially more toxicity among cells other than follicle cells of the at least one dissected egg chamber contacted with the compound than in the corresponding at least one dissected egg chamber not contacted with the compound, wherein the presence of a difference in expression of the reporter polypeptide in the apical part of the follicular epithelium of the at least one dissected egg chamber contacted with the compound compared to the follicular epithelium of the corresponding at least one dissected egg chamber not contacted with the compound, without the presence of substantially more toxicity among cells other than follicle cells of the at least one dissected egg chamber contacted with the compound compared to the corresponding at least one dissected egg chamber not contacted with the compound, identifies the compound as an epithelial cancer drug candidate.

7. The process of claim 1, wherein at least 10, 15, 20, 25, or 50 dissected *D. melanogaster* egg chambers are obtained and contacted with the compound.

8. A process for producing an epithelial cancer drug comprising:

(a) i) preparing or obtaining a group of compounds to be screened;
  ii) performing the process of claim 1 for each compound from the group of compounds to identify an epithelial cancer drug candidate; and
  iii) producing the compound identified in step ii), thereby producing the epithelial cancer drug, or (b) i) obtaining, by dissection from at least one *D. melanogaster* adult female fly, at least one *D. melanogaster* egg chamber which is genetically unmodified except that the at least one *D. melanogaster* egg chamber comprises at least one nucleotide sequence encoding a Par6 fusion protein under control of the Par6 endogenous promoter, wherein the Par6 fusion protein comprises a reporter polypeptide fused to Par6, and wherein the nucleic acid sequence that encodes the Par6 fusion protein and the Par6 endogenous promoter is SEQ ID NO: 10;
  ii) contacting the at least one dissected egg chamber with the compound by soaking it in an incubation medium containing the compound;
  iii) comparing the level of expression of the Par6 fusion protein in the apical part of the follicular epithelium of the at least one dissected egg chamber contacted with the compound, to the apical part of the follicular epithelium of a corresponding at least one dissected egg chamber not contacted with the compound, wherein the presence of a difference in the expression of the Par6 fusion protein in the apical part of the follicular epithelium of the at least one dissected egg chamber contacted with the compound compared to the follicular epithelium of the corresponding at least one dissected egg chamber not contacted with the compound identifies the compound as an epithelial cancer drug; and
  iv) producing the compound identified in step iii), thereby producing the epithelial cancer drug, or (c) i) obtaining, by dissection from at least one *D. melanogaster* adult female fly, at least one *D. melanogaster* egg chamber which is genetically unmodified except that the at least one *D. melanogaster* egg chamber optionally comprises at least one nucleotide sequence encoding a Par6 fusion protein under control of the Par6 endogenous promoter, wherein the Par6 fusion protein comprises a reporter polypeptide fused to Par6, and wherein the nucleic acid sequence that encodes the Par6 fusion protein and the Par6 endogenous promoter is SEQ ID NO: 10;
  ii) contacting the at least one dissected egg chamber with the compound, and up to four additional compounds by soaking it in an incubation medium containing the compounds;
  iii) comparing the level of expression of the Par6 fusion protein in the apical part of the follicular epithelium of the at least one dissected egg chamber contacted with the compound and up to four additional compounds, to the level in the apical part of the follicular epithelium of a corresponding at least one dissected egg chamber not contacted with the compound and up to four additional compounds;
  iv) if there is a difference in the expression of the Par6 fusion protein in the apical part of the follicular epithelium of the at least one dissected egg chamber contacted with the compound and up to four additional compounds compared to the follicular epithelium of the corresponding at least one dissected egg chamber not contacted with the compound, contacting at least one additional dissected egg chamber according to step i) with the compound but not the additional compound or compounds of step ii) and step iii); and v) comparing the level of expression or the Par6 fusion protein in the apical part of the follicular epithelium of the at least one additional dissected egg chamber of step iv), to the level in the apical part of the follicular epithelium of the corresponding at least one additional dissected egg chamber not contacted with the compound, wherein the presence of a difference in the expression of the Par6 fusion protein in the apical part of the follicular epithelium of the at least one additional dissected egg chamber of step iv) compared to the apical part of the follicular epithelium of the corresponding at least one additional dissected egg chamber not contacted with the compound identifies the compound as an epithelial cancer drug; and vi) producing the compound identified in step v), thereby producing the epithelial cancer drug.

9. The process of claim 1, wherein the at least one dissected egg chamber is soaked in the incubation medium containing the compound when the at least one dissected egg chamber is at a stage other than stage 1, 2, 3, or 4.

10. The process of claim 9, wherein the at least one dissected egg chamber is soaked in the incubation medium containing the compound when the at least one dissected egg chamber is at stage 7.

11. The process of claim 1, wherein the difference in the expression of the Par6 fusion protein in the apical part of the follicular epithelium of the at least one dissected egg chamber contacted with the compound compared to the expression of the Par6 fusion protein in the apical part of the follicular epithelium of a corresponding at least one dissected egg chamber not contacted with the compound is observed in a border cell, a stretch cell, a polar cell, or a centripetal cell using a microscope.

12. The process of claim 1, wherein the epithelial cancer comprises cells with disrupted Par6 function or disrupted epithelial cell polarity.

* * * * *